US005643933A

United States Patent [19]
Talley et al.

[11] Patent Number: 5,643,933
[45] Date of Patent: Jul. 1, 1997

[54] SUBSTITUTED SULFONYLPHENYLHETEROCYCLES AS CYCLOOXYGENASE-2 AND 5-LIPOXYGENASE INHIBITORS

[75] Inventors: John J. Talley, Brentwood; James A. Sikorski, Des Peres, both of Mo.; Bryan H. Norman, Indianapolis, Ind.; Roland S. Rogers, deceased, late of Richmond Heights, Mo., by Kathy L. Rogers, legal representative; Balekudru Devadas, Chesterfield, Mo.; Matthew J. Graneto, St. Louis, Mo.; Jeffery S. Carter, Chesterfield, Mo.

[73] Assignee: G. D. Searle & Co., Skokie, Ill.

[21] Appl. No.: 460,324

[22] Filed: Jun. 2, 1995

[51] Int. Cl.$^6$ .................. A61K 31/44; A61K 31/425; A61K 31/42; C09D 263/32; C07D 413/12; C07D 413/06; C07D 413/10; C07D 417/02

[52] U.S. Cl. .................. 514/372; 514/340; 514/369; 514/370; 514/365; 514/376; 514/377; 514/374; 514/378; 514/380; 546/271.4; 546/272.1; 548/225; 548/228; 548/229; 548/234; 548/235; 548/236; 548/243; 548/245; 548/246; 548/247; 548/248

[58] Field of Search ............. 548/235, 225, 548/228, 229, 234, 236, 243, 245, 246, 247, 248; 514/376, 377, 374, 378, 380

[56] References Cited

U.S. PATENT DOCUMENTS

| 5,098,932 | 3/1992 | Hamon | 514/462 |
|---|---|---|---|
| 5,234,939 | 8/1993 | Capiris et al. | 514/400 |
| 5,234,950 | 8/1993 | Edwards et al. | 514/473 |
| 5,240,941 | 8/1993 | Bruneau | 514/312 |
| 5,242,940 | 9/1993 | Wachter et al. | 514/406 |
| 5,298,521 | 3/1994 | Ferro | 514/406 |
| 5,302,603 | 4/1994 | Crawley et al. | 514/336 |
| 5,308,852 | 5/1994 | Girard et al. | 514/336 |
| 5,344,991 | 9/1994 | Reitz et al. | 568/34 |
| 5,354,865 | 10/1994 | Dellaria et al. | 546/158 |
| 5,356,898 | 10/1994 | Belliotti et al. | 514/269 |
| 5,364,877 | 11/1994 | Bruneau et al. | 514/414 |
| 5,373,007 | 12/1994 | Bruneau et al. | 514/224.2 |
| 5,380,738 | 1/1995 | Norman et al. | 514/374 |
| 5,393,790 | 2/1995 | Reitz et al. | 514/709 |
| 5,401,765 | 3/1995 | Lee | 548/406 |

FOREIGN PATENT DOCUMENTS

| 485111 | 5/1992 | European Pat. Off. |
| 94/13635 | 6/1994 | WIPO |
| 94/15932 | 7/1994 | WIPO |
| 94/20480 | 9/1994 | WIPO |
| 94/26731 | 11/1994 | WIPO |
| 94/27980 | 12/1994 | WIPO |
| 95/00501 | 1/1995 | WIPO |
| 95/30669 | 11/1995 | WIPO |

OTHER PUBLICATIONS

Crawley et al., J. Med. Chem, 35,2600–09 (1992).

*Primary Examiner*—Johann Richter
*Assistant Examiner*—Laura R. Cross
*Attorney, Agent, or Firm*—Joseph W. Bulock

[57] ABSTRACT

This invention is in the field of antiinflammatory pharmaceutical agents and specifically relates to compounds, compositions and methods for treating disorders mediated by cyclooxygenase-2 or 5-lipoxygenase, such as inflammation.

29 Claims, No Drawings

SUBSTITUTED SULFONYLPHENYLHETEROCYCLES AS CYCLOOXYGENASE-2 AND 5-LIPOXYGENASE INHIBITORS

FIELD OF THE INVENTION

This invention is in the field of antiinflammatory pharmaceutical agents and specifically relates to compounds, compositions and methods for treating disorders mediated by cyclooxygenase-2 or 5-lipoxygenase, such as inflammation and allergic conditions such as asthma.

BACKGROUND OF THE INVENTION

Prostaglandins play a major role in the inflammation process, and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway including the enzyme cyclooxygenase (COX). The recent discovery of an inducible enzyme associated with inflammation (named "cyclooxygenase-2 (COX-2)" or "prostaglandin G/H synthase II") provides a viable target of inhibition which more effectively reduces inflammation and produces fewer and less drastic side effects.

In another portion of the arachidonic acid pathway, physiologically active leukotrienes, such as leukotriene $B_4$ ($LTB_4$), leukotriene $C_4$ ($LTC_4$) and leukotriene $D_4$ ($LTD_4$) and other metabolites, are produced by the 5-lipoxygenase-mediated (5-LO) oxidation of arachidonic acid. These leukotrienes have been implicated in various inflammation-related disorders and allergic diseases, and thus compounds which inhibit 5-lipoxygenase are useful in the treatment of disease states in which leukotrienes play an important role.

It is believed that selective dual inhibitors of both cyclooxygenase-2 and 5-lipoxygenase, which affect the two enzymes at low concentrations, will more completely and permanently affect the damage caused by the various diseases and disorders mediated by cyclooxygenase-2 and 5-lipoxygenase but without the gastrointestinal side effects associated with traditional NSAIDs.

The references below that disclose antiinflammatory activity, show continuing efforts to find a safe and effective antiinflammatory agent. The novel compounds disclosed herein are such safe and also effective antiinflammatory agents furthering such efforts. The invention's compounds are found to show usefulness in vivo as antiinflammatory agents with minimal side effects. The compounds disclosed herein preferably selectively inhibit cyclooxygenase-2 over cyclooxygenase-1.

Compounds which selectively inhibit cyclooxygenase-2 have been described in U.S. Pat. Nos. 5,380,738, 5,344,991, 5,393,790 and WO documents WO94/15932, WO94/27980, WO95/00501, WO94/13635, WO94/20480, and WO94/26731.

Compounds which inhibit 5-lipoxygenase have been described in U.S. Pat. Nos. 5,364,877, 5,302,603, 5,234,950, 5,098,932 and 5,354,865, among others.

Compounds which inhibit cyclooxygenase and 5-lipoxygenase have been described in U.S. Pat. Nos. 5,298,521, 5,242,940, 5,234,939, and 5,356,898, among others. However, these previous mixed inhibitors do not selectively inhibit cyclooxygenase-2 and therefore still cause the gastrointestinal side effects which substantially reduce their usage and effectiveness.

The invention's compounds are found to show usefulness in vivo as dual inhibitors of cyclooxygenase-2 and 5-lipoxygenase with minimal side effects.

DESCRIPTION OF THE INVENTION

A class of compounds useful in treating cyclooxygenase-2 and 5-lipoxygenase-mediated disorders is defined by Formula I:

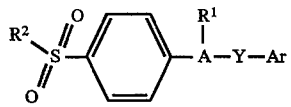

wherein A is a 5- or 6-member ring substituent selected from partially unsaturated or unsaturated heterocyclo and carbocyclic rings, wherein A is optionally substituted with a radical selected from acyl, halo, alkyl, haloalkyl, cyano, nitro, carboxyl, alkoxy, oxo, aminocarbonyl, alkoxycarbonyl, carboxyalkyl, cyanoalkyl, and hydroxyalkyl;

wherein Y is a radical selected from oxy, thio, sulfinyl, sulfonyl, alkyl, alkenyl, alkynyl, alkyloxy, alkylthio, alkylcarbonyl, cycloalkyl, aryl, haloalkyl, hydroxyalkyl, hydroxyalkyloxy, hydroxyalkyloxyalkyl, hydroxyalkylthio, hydroxyalkylthioalkyl, oximinoalkoxy, oximinoalkoxyalkyl, (alkyl)oximinoalkoxy, (alkyl)oximinoalkoxyalkyl, oximinoalkylthio, oximinoalkylthioalkyl, (alkyl)oximinoalkylthio, (alkyl)oximinoalkylthioalkyl, carbonylalkyloxy, carbonylalkyloxyalkyl, carbonylalkylthio, carbonylalkylthioalkyl, heterocyclo, cycloalkenyl, aralkyl, heterocycloalkyl, acyl, alkylthioalkyl, alkyloxyalkyl, alkenylthio, alkynylthio, alkenyloxy, alkynyloxy, alkenylthioalkyl, alkynylthioalkyl, alkenyloxyalkyl, alkynyloxyalkyl, arylcarbonyl, aralkylcarbonyl, aralkenyl, haloalkylcarbonyl, alkoxyalkyl, alkylaminocarbonylalkyl, heteroaralkoxyalkyl, heteroaryloxyalkyl, heteroarylthioalkyl, heteroaralkylthioalkyl, heteroaralkoxy, heteroaralkylthio, heteroaryloxy, heteroarylthio, arylthioalkyl, aryloxyalkyl, haloaryloxyalkyl, aralkylthioalkyl, aralkoxyalkyl, alkoxyaralkoxyalkyl, alkoxycarbonylalkyl, alkoxycarbonylcyanoalkenyl, aminocarbonylalkyl, N-alkylaminocarbonyl, N-arylaminocarbonyl, N,N-dialkylaminocarbonyl, N-alkyl-N-arylaminocarbonyl, cycloalkylaminocarbonyl, heterocycloaminocarbonyl, carboxyalkylaminocarbonyl, alkylcarbonylalkyl, aralkoxycarbonylalkylaminocarbonyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyl-N-aralkylamino, N-alkyl-N-arylamino, aminoalkyl, N-alkylaminoalkyl, N,N-dialkylaminoalkyl, N-arylaminoalkyl, N-aralkylaminoalkyl, N-alkyl-N-aralkylaminoalkyl, N-alkyl-N-arylaminoalkyl, aminoalkoxy, aminoalkoxyalkyl, aminoalkylthio, aminoalkylthioalkyl, cycloalkyloxy, cycloalkylthio, cycloalkylalkylthio, cycloalkylalkyloxy, aryloxy, aralkoxy, arylthio, aralkylthio, alkylsulfinyl, alkylsulfonyl, aminosulfonyl, N-alkylaminosulfonyl, N-arylaminosulfonyl, arylsulfonyl, N,N-dialkylaminosulfonyl, N-alkyl-N-arylaminosulfonyl,

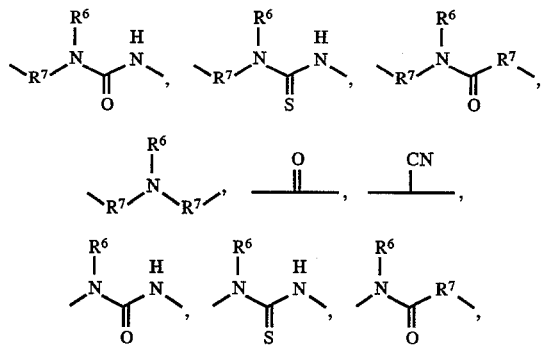

wherein Ar is selected from aryl and heteroaryl, wherein Ar is optionally substituted with one or two substituents selected from halo, hydroxyl, amino, nitro, cyano, carbamoyl, alkyl, alkenyloxy, alkoxy, alkylthio, alkylsulfinyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, alkoxycarbonylalkoxy and

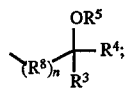

wherein $R^1$ is at least one substituent selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl and amino;

wherein $R^3$ and $R^4$ together form a group of the formula —B—X—$B^1$ which together with the carbon atom to which B and $B^1$ are attached, defines a ring having 6 ring atoms, wherein B and $B^1$, which may be the same or different, each is alkylene and X is oxy, and which ring may bear one, two or three substituents, which may be the same or different, selected from hydroxyl, alkyl, alkoxy, alkenyloxy and alkynyloxy;

wherein $R^5$ is selected from hydrido, alkyl, alkanoyl, and aroyl optionally substituted with a substituent selected from halo, alkyl and alkoxy;

wherein $R^6$ is selected from hydrido, alkyl, aryl and aralkyl;

wherein $R^7$ is selected from alkyl, alkenyl and alkynyl;

wherein $R^8$ is oximino optionally substituted with alkyl; and wherein n is 0 or 1;

or a pharmaceutically-acceptable salt thereof.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursiris, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as anti-inflammatory agents, such as for the treatment of arthritis, with the additional benefit of having significantly less harmful side effects. As inhibitors of 5-lipoxygenase, these compounds would also be useful in the treatment of allergic rhinitis, respiratory distress syndrome, endotoxin shock syndrome, atherosclerosis and central nervous system damage resulting from stroke. Besides being useful for human treatment, these compounds are also useful for treatment of mammals, including horses, dogs, cats, rats, mice, sheep, pigs, etc.

The present compounds may also be used in co-therapies, partially or completely, in place of other conventional antiinflammatories, such as together with steroids, NSAIDs, $LTB_4$ antagonists and $LTA_4$ hydrolase inhibitors.

The present invention preferably includes compounds which selectively inhibit cyclooxygenase-2 over cyclooxygenase-1 as well as inhibit the 5-lipoxygenase enzyme. Preferably, the compounds have a cyclooxygenase-2 $IC_{50}$ of less than about 0.5 μM, and also have a selectivity ratio of cyclooxygenase-2 inhibition over cyclooxygenase-1 inhibition of at least 50, and more preferably of at least 100, and inhibit 5-lipoxygenase at less that about 10 μM. Even more preferably, the compounds have a cyclooxygenase-1 $IC_{50}$ of greater than about 1 μM, and more preferably of greater than 20 μM and have a 5-lipoxygenase $IC_{50}$ of less than about 1 μM. Such preferred selectivity may indicate an ability to reduce the incidence of common NSAID-induced side effects.

A preferred class of compounds consists of those compounds of Formula I wherein A is a radical selected from thienyl, oxazolyl, furyl, pyrrolyl, thiazolyl, imidazolyl, isothiazolyl, isoxazolyl, pyrazolyl, cyclopentenyl, phenyl, and pyridyl, wherein A is optionally substituted with a radical selected from acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, lower carbonylalkyloxyalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylthio, lower alkylcarbonyl, lower cycloalkyl, phenyl, lower haloalkyl, 5- or 6-membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower heteroaralkoxyalkyl, lower heteroaryloxyalkyl, lower heteroarylthioalkyl, lower heteroaralkylthioalkyl, lower heteroaralkoxy, lower heteroaralkylthio, lower heteroaryloxy, lower heteroarylthio, lower arylthioalkyl, lower aryloxyalkyl, lower aralkylthioalkyl, lower aralkoxyalkyl, lower alkoxyaralkoxyalkyl, lower alkoxycarbonylalkyl, lower alkoxycarbonylcyanoalkenyl, lower aminocarbonylalkyl, lower N-alkylaminocarbonyl, N-phenylaminocarbonyl, lower N,N-dialkylaminocarbonyl, lower N-alkyl-N-arylaminocarbonyl, lower cycloalkylaminocarbonyl, lower heterocycloaminocarbonyl, lower carboxyalkylaminocarbonyl, lower alkylcarbonylalkyl, lower aralkoxycarbonylalkylaminocarbonyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-phenylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arylaminoalkyl, lower N-aralkylaminoalkyl, lower N-alkyl-N-aralkylaminoalkyl, lower N-alkyl-N-arylaminoalkyl, lower aminoalkoxy, lower aminoalkoxyalkyl, lower aminoalkylthio, lower aminoalkylthioalkyl, lower cycloalkyloxy, lower cycloalkylalkyloxy, phenyloxy, lower aralkoxy, phenylthio, lower aralkylthio, lower alkylsulfinyl, lower alkylsulfonyl, aminosulfonyl, lower N-alkylaminosulfonyl, lower N-arylaminosulfonyl, lower arylsulfonyl, lower N,N-dialkylaminosulfonyl, lower N-alkyl-N-arylaminosulfonyl,

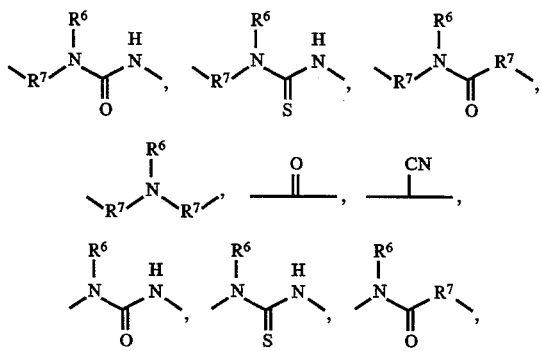

wherein Ar is selected from aryl selected from phenyl, biphenyl and naphthyl, and 5- and 6-membered heteroaryl, wherein Ar is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower alkoxycarbonylalkoxy and

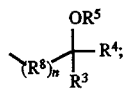

wherein $R^1$ is at least one substituent selected from 5- and 6-membered heterocyclo, lower cycloalkyl, lower cycloalkenyl and aryl selected from phenyl, biphenyl and naphthyl, where $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; wherein $R^3$ and $R^4$ together form a group of the formula —B—X—$B^1$ which together with the carbon atom to which B and $B^1$ are attached, defines a ring having 6 ring atoms, wherein B and $B^1$, which may be the same or different, each is alkylene and X is oxy, and which ring may bear one, two or three substituents, which may be the same or different, selected from hydroxyl, lower alkyl, lower alkoxy, lower alkenyloxy and lower alkynyloxy; wherein $R^5$ is selected from hydrido, lower alkyl, lower alkenyl, lower alkynyl, lower cyanoalkyl, lower alkanoyl, and benzoyl optionally substituted with a substituent selected from halo, lower alkyl and lower alkoxy; wherein $R^6$ is selected from hydrido, lower alkyl, phenyl and lower aralkyl; wherein $R^7$ is selected from lower alkyl, lower alkenyl and lower alkynyl; wherein $R^8$ is oximino optionally substituted with alkyl; and wherein n is 0 or 1; or a pharmaceutically-acceptable salt thereof.

A more preferred class of compounds consists of those compounds of Formula I wherein A is a radical selected from thienyl, oxazolyl, furyl, pyrrolyl, thiazolyl, imidazolyl, isothiazolyl, isoxazolyl, pyrazolyl, cyclopentenyl, phenyl, and pyridyl, wherein A is optionally substituted with a radical selected from acyl, halo, lower alkyl, lower haloalkyl, oxo, cyano, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, lower carbonylalkyloxyalkyl, lower hydroxyalkylthio, lower hydroxyalkylthioalkyl, lower oximinoalkalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylthio, lower alkylcarbonyl, lower cycloalkyl, phenyl, lower haloalkyl, 5- or 6-membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower arylthioalkyl, lower aryloxyalkyl, aralkylthioalkyl, lower aralkoxyalkyl, lower alkoxycarbonylalkyl, lower aminocarbonylalkyl, lower N-alkylaminocarbonyl, N-phenylaminocarbonyl, lower alkylcarbonylalkyl, lower N-alkylamino, N-phenylamino, lower N-aralkylamino, lower aminoalkyl, lower N-alkylaminoalkyl, lower N-arylaminoalkyl, lower N-aralkylaminoalkyl, lower aminoalkoxy, lower aminoalkoxyalkyl, lower aminoalkylthio, lower aminoalkylthioalkyl, lower cycloalkyloxy, lower cycloalkylalkyloxy, phenyloxy, lower aralkoxy, phenylthio, lower aralkylthio, lower alkylsulfinyl, lower alkylsulfonyl, aminosulfonyl, lower N-alkylaminosulfonyl, N-phenylaminosulfonyl, phenylsulfonyl, oximino,

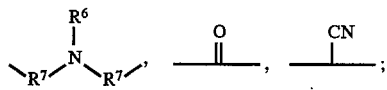

wherein Ar is selected from aryl selected from phenyl, biphenyl, naphthyl, and 5- and 6-membered heteroaryl, wherein Ar is optionally substituted with one or two substituents selected from halo, hydroxyl, amino, nitro, cyano, lower alkyl, lower alkoxy and

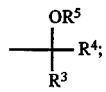

wherein $R^1$ is at least one substituent selected from 5- and 6-membered heteroaryl, and aryl selected from phenyl, biphenyl and naphthyl, where $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, nitro, lower alkoxyalkyl, lower alkylsulfinyl, halo, lower alkoxy and lower alkylthio; wherein $R^2$ is selected from lower alkyl and amino; wherein $R^3$ and $R^4$ together form a tetrahydropyran ring and which ring may bear one, two or three substituents, which may be the same or different, selected from hydroxyl, lower alkyl, and lower alkoxy; wherein $R^5$ is selected from hydrido and lower alkyl; wherein $R^6$ is selected from hydrido, lower alkyl, phenyl and lower aralkyl; and wherein $R^7$ is selected from lower alkyl, lower alkenyl and lower alkynyl; or a pharmaceutically-acceptable salt thereof.

An even more preferred class of compounds consists of those compounds of Formula I wherein A is a radical selected from thienyl, oxazolyl, furyl, pyrrolyl, thiazolyl, imidazolyl, isothiazolyl, isoxazolyl, pyrazolyl, cyclopentenyl, phenyl, and pyridyl, wherein A is optionally substituted with a radical selected from acyl, halo, lower alkyl, lower haloalkyl, oxo, cyano, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkynyl, lower alkenyl, aryl, lower cycloalkyl, 5- or 6-membered heterocyclo, aralkyl, lower alkyloxy, aryloxy, arylthio, 5- or 6-membered heterocyclooxy, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkyloxyalkyl, lower alkylthioalkyl, lower hydroxyalkyloxy, lower hydroxyalkyloxyalkyl, lower oximinoalkoxy, lower oximinoalkoxyalkyl, lower (alkyl) oximinoalkoxy, lower (alkyl)oximinoalkoxyalkyl, lower carbonylalkyloxy, and lower carbonylalkyloxyalkyl; wherein Ar is selected from phenyl, thienyl, oxazolyl, furyl, pyrrolyl, thiazolyl, imidazolyl, isothiazolyl, isoxazolyl, pyrazolyl, cyclopentenyl, and pyridyl, wherein Ar is optionally substituted with one or two substituents selected from halo, hydroxyl, lower alkyl, lower alkoxy, and

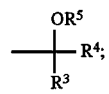

wherein $R^1$ is selected from thienyl, oxazolyl, furyl, pyrrolyl, thiazolyl, imidazolyl, isothiazolyl, isoxazolyl, pyrazolyl, cyclopentenyl, pyridyl, and phenyl, where $R^1$ is optionally substituted at a substitutable position with one or more radicals selected from lower alkyl, lower haloalkyl, hydroxyl, lower hydroxyalkyl, lower haloalkoxy, nitro, lower alkoxyalkyl, halo, lower alkoxy and lower alkylthio; wherein $R^2$ is selected from lower alkyl and amino; wherein $R^3$ and $R^4$ together form a tetrahydropyran ring, and which ring may bear one, two or three substituents, which may be the same or different, selected from hydroxyl, lower alkyl, and lower alkoxy; and wherein $R^5$ is selected from hydrido and lower alkyl; or a pharmaceutically-acceptable salt thereof.

A class of compounds of particular interest consists of those compounds of Formula I wherein A is a radical selected from thienyl, oxazolyl, furyl, pyrrolyl, thiazolyl, imidazolyl, isothiazolyl, isoxazolyl, pyrazolyl, cyclopentenyl, phenyl, and pyridyl, wherein A is optionally substituted with a radical selected from acyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl; wherein Y is a radical selected from oxy, ethyl, isopropyl, butyl, 1-propynyl, 2-propynyl, methyloxy, ethyloxy, propyloxy, methylthio, (Z)-1-propenyloxy, (E)-2-propenyloxy, (Z)-2-propenyloxy, (E)-1-propenyloxy, Z)-1-propenyloxymethyl, (E)-2-propenyloxymethyl, (Z)-2-propenyloxymethyl, (E)-1-propenyloxymethyl, 1-propynyloxy, 2-propynyloxy, 1-propynylthio, 2-propynylthio, hydroxymethyloxy, 1-hydroxyethyloxy, 2-hydroxypropyloxy, hydroxymethyloxymethyl, 1-hydroxyethyloxymethyl, 2-hydroxypropyloxymethyl, methyloxymethyl, ethyloxymethyl, propyloxymethyl, 1-propynyloxymethyl, oximinomethyloxy, oximinomethyloxymethyl, (methyl)oximinomethyloxy, (methyl)oximinomethyloxymethyl, triazolylmethyloxy, triazolylmethyloxymethyl, carbonylmethyloxy, carbonylbutyloxy, and carbonylmethyloxymethyl; wherein Ar is selected from phenyl, thienyl, oxazolyl, furyl, pyrrolyl, thiazolyl, imidazolyl, isothiazolyl, isoxazolyl, pyrazolyl, cyclopentenyl, and pyridyl, wherein Ar is optionally substituted with one or two substituents selected from fluoro, chloro, bromo, hydroxyl, methyl, methoxy, and

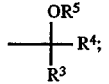

wherein $R^1$ is selected from thienyl, oxazolyl, furyl, pyrrolyl, thiazolyl, imidazolyl, isothiazolyl, isoxazolyl, pyrazolyl, cyclopentenyl, pyridyl, and phenyl, where $R^1$ is optionally substituted at a substitutable position with one or more radicals selected from methyl, trifluoromethyl, hydroxyl, hydroxymethyl, trifluoromethoxy, nitro, methoxymethyl, fluoro, chloro, bromo, methoxy and methylthio; wherein $R^2$ is methyl or amino; wherein $R^3$ and $R^4$ together form a tetrahydropyran ring, and which ring may bear one, two or three substituents, which may be the same or different, selected from hydroxyl, methyl, and methoxy; and wherein $R^5$ is selected from hydrido and methyl; or a pharmaceutically-acceptable salt thereof.

Within Formula I there is a subclass of compounds of high interest represented by Formula II:

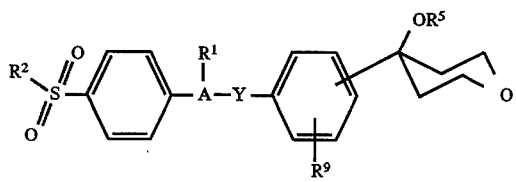

wherein A is a ring substituent selected from thienyl, oxazolyl, furyl, pyrrolyl, thiazolyl, imidazolyl, isothiazolyl, isoxazolyl, pyrazolyl, cyclopentenyl, phenyl, and pyridyl; wherein A is optionally substituted with a radical selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

wherein Y is a radical selected from oxy, thio, sulfinyl, sulfonyl, lower alkyl, lower alkynyl, lower alkenyl, lower hydroxyalkyl, aryl, lower cycloalkyl, 5- or 6-membered heterocyclo, aralkyl, lower alkyloxy, aryloxy, arythio, lower cycloalkyloxy, 5- or 6-membered heterocyclooxy, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkyloxyalkyl, lower alkylthioalkyl, lower hydroxyalkylthio, lower hydroxyalkylthioalkyl, lower oximinoalkylthio, lower oximinoalkylthioalkyl, lower (alkyl)oximinoalkylthio, lower (alkyl) oximinoalkylthioalkyl, lower carbonylalkylthio, lower carbonylalkylthioalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, and lower carbonylalkyloxyalkyl;

wherein $R^1$ is a substituent selected from 5- and 6-membered heterocyclo, lower cycloalkyl, lower cycloalkenyl and aryl selected from phenyl, biphenyl and naphthyl, wherein $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio;

wherein $R^2$ is selected from lower alkyl and amino;

wherein $R^5$ is selected from hydrido, alkyl, alkenyl, alkynyl, cyanoalkyl, alkanoyl, and aroyl optionally substituted with a substituent selected from halo, alkyl and alkoxy; and wherein $R^9$ is one or two substituents selected from halo, hydroxyl, amino, nitro, cyano, carbamoyl, alkyl, alkenyloxy, alkoxy, alkylthio, alkylsulfinyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, and alkoxycarbonylalkoxy; or a pharmaceutically-acceptable salt thereof.

A preferred class of compounds consists of those compounds of Formula II wherein A is a radical selected from thienyl, oxazolyl, furyl, pyrrolyl, thiazolyl, imidazolyl, isothiazolyl, isoxazolyl, pyrazolyl, cyclopentenyl, phenyl, and pyridyl; wherein A is optionally substituted with a radical selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, lower alkyl, lower alkynyl, 5- or 6-membered heterocyclo, lower hydroxyalkyl, lower alkyloxy, lower alkylthio, lower alkyloxyalkyl, lower alkenyloxy, lower alkenyloxyalkyl, lower alkynyloxy, lower alkynylthio, lower alkynyloxyalkyl, lower hydroxyalkylthio, lower hydroxyalkylthioalkyl, lower oximinoalkylthio, lower oximinoalkylthioalkyl, lower (alkyl)oximinoalkylthio, lower (alkyl) oximinoalkylthioalkyl, lower carbonylalkylthio, lower carbonylalkylthioalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, and lower carbonylalkyloxyalkyl; wherein $R^1$ is phenyl optionally substituted at a substitutable position with one or more radicals selected from lower alkyl, lower haloalkyl, hydroxyl, lower hydroxyalkyl, nitro, halo, and lower alkoxy; wherein $R^2$ is selected from lower alkyl and amino; wherein $R^5$ is selected from hydrido, and lower alkyl; and wherein $R^9$ is one or two substituents selected from halo, hydroxyl, amino, lower alkyl, lower alkoxy; or a pharmaceutically-acceptable salt thereof.

A class of compounds of particular interest consists of those compounds of Formula II wherein A is a radical selected from thienyl, oxazolyl, furyl, pyrrolyl, thiazolyl, imidazolyl, isothiazolyl, isoxazolyl, pyrazolyl, cyclotpentenyl, phenyl, and pyridyl; wherein A is optionally substituted with a radical selected from formyl, fluoro, chloro, bromo, hydroxyl, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluorotpropyl, dichloroethyl, dichloropropyl, oxo, cyano, nitro, carboxyl, methoxy, ethoxy, propoxy, n-butoxy, pentoxy, hexyloxy, methylenedioxy, aminocarbonyl, methoxycarbonyl, carborypropyl, carboxymethyl, carboxyethyl, cyanomethyl, and hydroxymethyl; wherein Y is a radical selected from oxy, ethyl, isoprotDyl, butyl, 1-propynyl, 2-propynyl, methyloxy, ethyloxy, propyloxy, methylthio, (Z)-1-propenyloxy, (E)-2-propenyloxy, (Z)-2-propenyloxy, (E)-1-propenyloxy, Z)-1-propenyloxymethyl, (E)-2-propenyloxymethyl, (Z)-2-propenyloxymethyl, (E)-1-propenyloxymethyl, 1-propynyloxy, 2-propynyloxy, 1-propynylthio, 2-propynylthio, hydroxymethyl, hydroxyethyl, hydroxypropyl, hydroxymethyloxy, 1-hydroxyethyloxy, 2-hydroxypropyloxy, hydroxymethyloxymethyl, 1-hydroxyethyloxymethyl, 2-hydroxypropyloxymethyl, methyloxymethyl, ethyloxymethyl, propyloxymethyl, 1-propynyloxymethyl, hydroxymethylthio, 1-hydroxyethylthio, 2-hydroxypropylthio, hydroxymethylthiomethyl, 1-hydroxyethylthiomethyl, 2-hydroxypropylthiomethyl, oximinomethylthio, oximinomethylthiomethyl, (methyl) oximinomethylthio, (methyl)oximinomethylthiomethyl, triazolylmethyloxy, triazolylmethyloxymethyl, carbonylmethylthio, carbonylbutylthio, carbonylmethylthiomethyl, oximinomethyloxy, oximinomethyloxymethyl, (methyl)oximinomethyloxy, (methyl)oximinomethyloxymethyl, triazolyl, carbonylmethyloxy, carbonylbutyloxy, and carbonylmethyloxymethyl; wherein $R^1$ is phenyl optionally substituted at a substitutable position with one or more radicals selected from methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, nitro, fluoro, chloro, bromo, methoxy, ethoxy, propoxy, n-butoxy, pentoxy, and hexyloxy;

wherein R² is selected from methyl, ethyl, isopropyl, butyl, tert-butyl, isobutyl, pentyl, hexyl, and amino; wherein R⁵ is selected from hydrido, and methyl, ethyl, isopropyl, butyl, tert-butyl, isobutyl, pentyl, hexyl; and wherein R⁹ is one or two substituents selected from fluoro, chloro, bromo, hydroxyl, amino, methyl, ethyl, isopropyl, butyl, tert-butyl, isobutyl, pentyl, hexyl, methoxy, ethoxy, propoxy, n-butoxy, pentoxy, and hexyloxy; or a pharmaceutically-acceptable salt thereof.

A class of compounds of particular interest consists of those compounds of Formula I 4-[5-(4-chlorophenyl)-3-(3-methoxyphenyl)oxymethyl-1H pyrazol-1-yl]benzenesulfonamide;

4-[5-(4-chlorophenyl)-3-(3-methoxyphenyl)thiomethyl-1H pyrazol-1-yl]benzenesulfonamide;

4-[5-(phenyl)-3-[[3-(3,4,5,6-tetrahydro-4-methoxy-2H-pyran-4-yl)phenoxy]acetyl]-1H-pyrazol-1-yl] benzenesulfonamide;

4-[5-(phenyl)-1-[4-(methylsulfonyl)phenyl]-2-[[3-(3,4,5,6-tetrahydro-4-methoxy-2H-pyran-4-yl)phenoxy]acetyl] pyrazole;

4-[5-(phenyl)-3-[[3-fluoro-5-(3,4,5,6-tetrahydro-4-methoxy-2H-pyran-4-yl)phenoxy]acetyl]-1H-pyrazol-1-yl]benzenesulfonamide;

4-[5-(phenyl)-3-[[3-(3,4,5,6-tetrahydro-4-methoxy-2H-pyran-4-yl)benzyloxy]acetyl]-1H-pyrazol-1-yl] benzenesulfonamide;

4-[5-(4-chlorophenyl)-3-[[3-fluoro-5-(3,4,5,6-tetrahydro-4-methoxy-2H-pyran-4-yl)phenoxy]methyl]-1H-pyrazol-1-yl]benenesulfonamide;

4-[1-(phenyl)-3-[[3-(3,4,5,6-tetrahydro-4-methoxy-2H-pyran-4-yl)phenoxy]acetyl]-1H-pyrazol-5-yl] benzenesulfonamide;

4-[1-(phenyl)-3-[[3-fluoro-5-(3,4,5,6-tetrahydro-4-methoxy-2H-pyran-4-yl)phenoxy]acetyl]-1H-pyrazol-5-yl]benzenesulfonamide;

4-[1-(phenyl)-3-[[3-(3,4,5,6-tetrahydro-4-methoxy-2H-pyran-4-yl)benzyloxy]acetyl]-1H-pyrazol-5-yl] benzenesulfonamide;

4-[4-(phenyl)-2-[[3-(3,4,5,6-tetrahydro-4-methoxy-2H-pyran-4-yl)phenoxy]acetyl]-5-thiazolyl] benzenesulfonamide;

4-[5-(phenyl)-4-[4-(methylsulfonyl)phenyl]-2-[[3-(3,4,5,6-tetrahydro-4-methoxy-2H-pyran-4-yl)phenoxy]acetyl] thiazole;

4-[5-(phenyl)-2-[[3-fluoro-5-(3,4,5,6-tetrahydro-4-methoxy-2H-pyran-4-yl)phenoxy]acetyl]-4-thiazolyl] benzenesulfonamide;

4-[4-(phenyl)-2-[[3-(3,4,5,6-tetrahydro-4-methoxy-2H-pyran-4-yl)benzyloxy]acetyl]-5-thiazolyl] benzenesulfonamide;

4-[3-(phenyl)-5-[[3-(3,4,5,6-tetrahydro-4-methoxy-2H-pyran-4-yl)phenoxy]acetyl]-4-isoxazolyl] benzenesulfonamide;

4-[3-(phenyl)-4-[4-(methylsulfonyl)phenyl]-5-[[3-(3,4,5,6-tetrahydro-4-methoxy-2H-pyran-4-yl)phenoxy]acetyl] isoxazole;

4-[3-(phenyl)-5-[[3-fluoro-5-(3,4,5,6-tetrahydro-4-methoxy-2H-pyran-4-yl)phenoxy]acetyl]-4-isoxazolyl] benzenesulfonamide;

4-[3-(phenyl)-5-[[3-(3,4,5,6-tetrahydro-4-methoxy-2H-pyran-4-yl)benzyloxy]acetyl]-4-isoxazolyl] benzenesulfonamide;

4-[4-(phenyl)-2-[[3-(3,4,5,6-tetrahydro-4-methoxy-2H-pyran-4-yl)phenoxy]acetyl]-1-imidazolyl]benzenesulfonamide;

4-[5-(phenyl)-4-[4-(methylsulfonyl)phenyl]-2-[[3-(3,4,5,6-tetrahydro-4-methoxy-2H-pyran-4-yl)phenoxy]acetyl] imidazole;

4-[5-(phenyl)-2-[[3-fluoro-5-(3,4,5,6-tetrahydro-4-methoxy-2H-pyran-4-yl)phenoxy]acetyl]-4-imidazolyl] benzenesulfonamide;

4-[2-(phenyl)-4-[[3-(3,4,5,6-tetrahydro-4-methoxy-2H-pyran-4-yl)benzyloxy]acetyl]-1-imidazolyl] benzenesulfonamide;

4-[3-(phenyl)-4-[[3-(3,4,5,6-tetrahydro-4-methoxy-2H-pyran-4-yl)phenoxy]acetyl]-2-pyridyl] benzenesulfonamide;

4-[3-(phenyl)-2-[4-(methylsulfonyl)phenyl]-4-[[3-(3,4,5,6-tetrahydro-4-methoxy-2H-pyran-4-yl)phenoxy]acetyl] pyridine;

4-[2-(phenyl)-4-[[3-fluoro-5-(3,4,5,6-tetrahydro-4-methoxy-2H-pyran-4-yl)phenoxy]acetyl]-3-pyridyl] benzenesulfonamide;

4-[2-(phenyl)-4-[[3-(3,4,5,6-tetrahydro-4-methoxy-2H-pyran-4-yl)benzyloxy]acetyl]-3-pyridyl] benzenesulfonamide;

4-[2-[3-(4-methoxy-3,4,5,6-tetrahydro-2H-pyran-4yl) phenoxy]-4-phenyl-5-oxazolyl]benzenesulfonamide;

4-[2-[3-fluoro-5-(4-methoxy-3,4,5,6-tetrahydro-2H-pyran-4-yl)phenoxy]-4-phenyl-5-oxazolyl] benzenesulfonamide;

4-(4-fluorophenyl)-2-[[3-fluoro-5-(3,4,5,6-tetrahydro-4-methoxy-2H-pyran-4-yl)phenoxy)methyl]-5-(4-(methylsulfonyl)phenyl)oxazole;

4-(4-fluorophenyl)-5-(4-(methylsulfonyl)phenyl)-2-[[3-(3,4,5,6-tetrahydro-4-methoxy-2H-pyran-4-yl)phenoxy) methyl]oxazole;

4-[4-(phenyl)-2-[[3-(3,4,5,6-tetrahydro-4-methoxy-2H-pyran-4-yl)phenoxy]acetyl]-5-oxazolyl] benzenesulfonamide;

4-[4-(phenyl)-5-[4-(methylsulfonyl)phenyl]-2-[[3-(3,4,5,6-tetrahydro-4-methoxy-2H-pyran-4-yl)phenoxy]acetyl] oxazole;

4-[4-(phenyl)-2-[[3-fluoro-5-(3,4,5,6-tetrahydro-4-methoxy-2H-pyran-4-yl)phenoxy]acetyl]-5-oxazolyl] benzenesulfonamide;

4-[4-(phenyl)-[[3-(3,4,5,6-tetrahydro-4-methoxy-2H-pyran-4-yl)benzyloxy]acetyl]-5-oxazolyl]benzenesulfonamide;

4-[4-(phenyl)-2-[[3-fluoro-5-(3,4,5,6-tetrahydro-4-methoxy-2H -pyran-4-yl)benzyloxy]acetyl]-5-oxazolyl] benzenesulfonamide;

4-[4-(phenyl)-2-[[3-(3,4,5,6-tetrahydro-4-methoxy-2H-pyran-4-yl)2-thienyloxy]acetyl]-5-oxazolyl] benzenesulfonamide;

4-[4-(phenyl)-2-[[5-(3,4,5,6-tetrahydro-4-methoxy-2H-pyran-4-yl)-3-pyridinyloxy]acetyl]-5-oxazolyl] benzenesulfonamide;

4-[4-(phenyl)-2-[[5-(3,4,5,6-tetrahydro-4-methoxy-2H-pyran-4-yl)-3-pyridylmethoxy]acetyl]-5-oxazolyl] benzenesulfonamide;

4-(phenyl)-2-[[6-(3,4,5,6-tetrahydro-4-methoxy-2H-pyran-4-yl)pyridin-2-yl-methoxy]acetyl]-5-oxazolyl] benzenesulfonamide;

4-(phenyl)-2-[[3-(2,6-dimethyl-3,4,5,6-tetrahydro-4-methoxy-2H-pyran-4-yl)benzyloxy]acetyl]-5-oxazolyl] benzenesulfonamide;

4-(phenyl)-2-[[2-(3,4,5,6-tetrahydro-4-methoxy-2H-pyran-4-yl)thiazol-4-yl-methoxy]acetyl]-5-oxazolyl] benzenesulfonamide;

4-(phenyl)-2-[[3-fluoro-5-(1S, 5R 3α-methoxy-6,8-dioxabicyclo[3.2.1]octanyl)phenoxy]acetyl]-5-oxazolyl] benzenesulfonamide;

4-(phenyl)-2-[[3-(3,4,5,6-tetrahydro-4-hydroxy-2H-pyran-4-yl)phenoxy]acetyl]-5-oxazolyl]benzenesulfonamide;

4-(phenyl)-5-[4-(methylsulfonyl)phenyl]-2-[[3-(3,4,5,6-tetrahydro-4-hydroxy-2H-pyran-4-yl)phenoxy]acetyl] oxazole;

4-(phenyl)-2-[[3-fluoro-5-(3,4,5,6-tetrahydro-4-hydroxy-2H-pyran-4-yl)phenoxy]acetyl]-5-oxazolyl]benzenesulfonamide;

4-(phenyl)-2-[[3-(3,4,5,6-tetrahydro-4-hydroxy-2H-pyran-4-yl)benzyloxy]acetyl]-5-oxazolyl]benzenesulfonamide;

4-(phenyl)-2-[[3-fluoro-5-(3,4,5,6-tetrahydro-4-hydroxy-2H-pyran-4-yl)benzyloxy]acetyl]-5-oxazolyl]benzenesulfonamide;

4-(phenyl)-2-[[3-(3,4,5,6-tetrahydro-4-hydroxy-2H-pyran-4-yl)thienyloxy]acetyl]-5-oxazolyl]benzenesulfonamide;

4-[4-(phenyl)-2-[[5-(3,4,5,6-tetrahydro-4-hydroxy-2H-pyran-4-yl)pyridin-3-yloxy]acetyl]-5-oxazolyl]benzenesulfonamide;

4-[4-(phenyl)-2-[[5-(3,4,5,6-tetrahydro-4-hydroxy-2H-pyran-4-yl)pyridin-3-ylmethoxy]acetyl]-5-oxazolyl]benzenesulfonamide;

4-[4-(phenyl)-2-[[6-(3,4,5,6-tetrahydro-4-hydroxy-2H-pyran-4-yl)pyridin-2-ylmethoxy]acetyl]-5-oxazolyl]benzenesulfonamide;

4-[4-(phenyl)-2-[[3-(2,6-dimethyl-3,4,5,6-tetrahydro-4-hydroxy-2H-pyran-4-yl)benzyloxy]acetyl]-5-oxazolyl]benzenesulfonamide;

4-[4-(phenyl)-2-[[2-(3,4,5,6-tetrahydro-4-hydroxy-2H-pyran-4-yl)thiazol-4-ylmethoxy]acetyl]-5-oxazolyl]benzenesulfonamide;

4-[4-(phenyl)-2-[[3-fluoro-5-(1S, 5R 3α-hydroxy-6,8-dioxabicyclo[3.2.1]octanyl)phenoxy]acetyl]-5-oxazolyl]benzenesulfonamide;

4-[4-(phenyl)-2-[2-[3-(3,4,5,6-tetrahydro-4-methoxy-2H-pyran-4-yl)phenoxy](E-oximinomethyl)ethyl]-5-oxazolyl]benzenesulfonamide;

4-[4-(phenyl)-2-[2-[3-(3,4,5,6-tetrahydro-4-methoxy-2H-pyran-4-yl)phenoxy](Z-oximinomethyl)ethyl]-5-oxazolyl]benzenesulfonamide;

4-[4-(phenyl)-2-[2-[3-(3,4,5,6-tetrahydro-4-methoxy-2H-pyran-4-yl)phenoxy](E-oximino)ethyl]-5-oxazolyl]benzenesulfonamide;

4-[4-(phenyl)-2-[2-[3-(3,4,5,6-tetrahydro-4-methoxy-2H-pyran-4-yl)phenoxy](Z-oximino)ethyl]-5-oxazolyl]benzenesulfonamide;

4-[4-(phenyl)-5-[4-[4-(methylsulfonyl)phenyl]-2-[2-[3-(3,4,5,6-tetrahydro-4-methoxy-2H-pyran-4-yl)phenoxy](E-oximinomethyl)ethyl]oxazole;

4-[4-(phenyl)-5-[4-[4-(methylsulfonyl)phenyl]-2-[2-[3-(3,4,5,6-tetrahydro-4-methoxy-2H-pyran-4-yl)phenoxy](Z-oximinomethyl)ethyl]oxazole;

4-[4-(phenyl)-2-[2-[3-fluoro-5-(3,4,5,6-tetrahydro-4-methoxy-2H-pyran-4-yl)phenoxy](E-oximino)ethyl]-5-oxazolyl]benzenesulfonamide;

4-[4-(phenyl)-2-[2-[3-fluoro-5-(3,4,5,6-tetrahydro-4-methoxy-2H-pyran-4-yl)phenoxy](Z-oximino)ethyl]-5-oxazolyl]benzenesulfonamide;

4-[4-(phenyl)-2-[2-[3-(3,4,5,6-tetrahydro-4-methoxy-2H-pyran-4-yl)benzyloxy](E-oximino)ethyl]-5-oxazolyl]benzenesulfonamide;

4-[4-(phenyl)-2-[2-[3-(3,4,5,6-tetrahydro-4-methoxy-2H-pyran-4-yl)benzyloxy](Z-oximino)ethyl]-5-oxazolyl]benzenesulfonamide;

4-[4-(phenyl)-2-[2-[3-fluoro-5-(3,4,5,6-tetrahydro-4-methoxy-2H-pyran-4-yl)benzyloxy](E-oximino)ethyl]-5-oxazolyl]benzenesulfonamide;

4-[4-(phenyl)-2-[2-[3-fluoro-5-(3,4,5,6-tetrahydro-4-methoxy-2H-pyran-4-yl)benzyloxy](Z-oximino)ethyl]-5-oxazolyl]benzenesulfonamide;

4-[4-(phenyl)-2-[2-[3-(3,4,5,6-tetrahydro-4-methoxy-2H-pyran-4-yl)thienyloxy](E-oximino)ethyl]-5-oxazolyl]benzenesulfonamide;

4-[4-(phenyl)-2-[2-[3-(3 4,5,6-tetrahydro-4-methoxy-2H-pyran-4-yl)thienyloxy](Z-oximino)ethyl]-5-oxazolyl]benzenesulfonamide;

4-[4-(phenyl)-2-[2-[5-(3 4,5,6-tetrahydro-4-methoxy-2H-pyran-4-yl)pyridin-3-yloxy](E-oximino)ethyl]-5-oxazolyl]benzenesulfonamide;

4-[4-(phenyl)-2-[2-[5-(3 4,5,6-tetrahydro-4-methoxy-2H-pyran-4-yl)pyridin-3-yloxy](Z-oximino)ethyl]-5-oxazolyl]benzenesulfonamide;

4-[4-(phenyl)-2-[2-[5-(3 4,5,6-tetrahydro-4-methoxy-2H-pyran-4-yl)pyridin-3-ylmethoxy](E-oximino)ethyl]-5-oxazolyl]benzenesulfonamide;

4-[4-(phenyl)-2-[2-[5-(3 4,5,6-tetrahydro-4-methoxy-2H-pyran-4-yl)pyridin-3-ylmethoxy](Z-oximino)ethyl]-5-oxazolyl]benzenesulfonamide;

4-[4-(phenyl)-2-[2-[6-(3 4,5,6-tetrahydro-4-methoxy-2H-pyran-4-yl)pyridin-2-ylmethoxy](E-oximino)ethyl]-5-oxazolyl]benzenesulfonamide;

4-[4-(phenyl)-2-[2-[6-(3 4,5,6-tetrahydro-4-methoxy-2H-pyran-4-yl)pyridin-2-ylmethoxy](Z-oximino)ethyl]-5-oxazolyl]benzenesulfonamide;

4-[4-(phenyl)-2-[2-[3-(2,6-dimethyl-3,4,5,6-tetrahydro-4-methoxy-2H-pyran-4-yl)benzyloxy](E-oximino)ethyl]-5-oxazolyl]benzenesulfonamide;

4-[4-(phenyl)-2-[2-[3-(2,6-dimethyl-3,4,5,6-tetrahydro-4-methoxy-2H-pyran-4-yl)benzyloxy](Z-oximino)ethyl]-5-oxazolyl]benzenesulfonamide;

4-[4-(phenyl)-2-[2-[2-(3,4,5,6-tetrahydro-4-methoxy-2H-pyran-4-yl)thiazol-4-ylmethoxy](E-oximino)ethyl]-5-oxazolyl]benzenesulfonamide;

4-[4-(phenyl)-2-[2-[2-(3,4,5,6-tetrahydro-4-methoxy-2H-pyran-4-yl)thiazol-4-ylmethoxy](Z-oximino)ethyl]-5-oxazolyl]benzenesulfonamide;

4-[4-(phenyl)-2-[2-[3-fluoro-5-(1S, 5R 3α-methoxy-6,8-dioxabicyclo[3.2.1]octanyl)phenoxy](Z-oximino)ethyl]-5-oxazolyl]benzenesulfonamide;

4-[4-(phenyl)-2-[2-[3-fluoro-5-(1S,5R 3α-methoxy-6,8-dioxabicyclo[3.2.1]octanyl)phenoxy](E-oximino)ethyl]-5-oxazolyl]benzenesulfonamide;

4-[4-(phenyl)-2-[3-[3-(3,4,5,6-tetrahydro-4-methoxy-2H-pyran-4-yl)phenoxy]propyn-1-yl]-5-oxazolyl]benzenesulfonamide;

4-[4-(phenyl)-5-[4-[4-(methylsulfonyl)phenyl]-2-[3-[3-(3,4,5,6-tetrahydro-4-methoxy-2H-pyran-4-yl)phenoxy]propyn-1-yl]oxazole;

4-[4-(phenyl)-2-[3-[3-fluoro-5-(3,4,5,6-tetrahydro-4-methoxy-2H-pyran-4-yl)phenoxy]propyn-1-yl]-5-oxazolyl]benzenesulfonamide;

4-[4-(phenyl)-2-[3-[3-(3,4,5,6-tetrahydro-4-methoxy-2H-pyran-4-yl)benzyloxy]propyn-1-yl]-5-oxazolyl]benzenesulfonamide;

4-[4-(phenyl)-2-[3-[3-fluoro-5-(3,4,5,6-tetrahydro-4-methoxy-2H-pyran-4-yl)benzyloxy]propyn-1-yl]-5-oxazolyl]benzenesulfonamide;

4-[4-(phenyl)-2-[3-[3-(3,4,5,6-tetrahydro-4-methoxy-2H-pyran-4-yl)thienyloxy]propyn-1-yl]-5-oxazolyl]benzenesulfonamide;

4-[4-(phenyl)-2-[3-[5-(3,4,5,6-tetrahydro-4-methoxy-2H-pyran-4-yl)pyridin-3-yloxy]propyn-1-yl]-5-oxazolyl]benzenesulfonamide;

4-[4-(phenyl)-2-[3-[5-(3,4,5,6-tetrahydro-4-methoxy-2H-pyran-4-yl)pyridin-3-ylmethoxy]propyn-1-yl]-5-oxazolyl]benzenesulfonamide;

4-[4-(phenyl)-2-[3-[6-(3,4,5,6-tetrahydro-4-methoxy-2H-pyran-4-yl)pyridin-2-ylmethoxy]propyn-1-yl]-5-oxazolyl]benzenesulfonamide;

4-[4-(phenyl)-2-[3-[3-(2,6-dimethyl-3,4,5,6-tetrahydro-4-methoxy-2H-pyran-4-yl)benzyloxy]propyn-1-yl]-5-oxazolyl]benzenesulfonamide;

4-[4-(phenyl)-2-[3-[2-(3,4,5,6-tetrahydro-4-methoxy-2H-pyran-4-yl)thiazol-4-ylmethoxy]propyn-1-yl]-5-oxazolyl]benzenesulfonamide;

4-[4-(phenyl)-2-[3-[3-fluoro-5-(1S, 5R 3α-methoxy-6,8-dioxabicyclo[3.2.1]octanyl)phenoxy]propyn-1-yl]-5-oxazolyl]benzenesulfonamide;

4-[4-(phenyl)-2-[3-[3-(3,4,5,6-tetrahydro-4-hydroxy-2H-pyran-4-yl)phenoxy]propyn-1-yl]-5-oxazolyl]benzenesulfonamide;

4-[4-(phenyl)-5-[4-[4-(methylsulfonyl)phenyl]-2-[3-[3-(3,4,5,6-tetrahydro-4-hydroxy-2H-pyran-4-yl)phenoxy]propyn-1-yl]oxazole;

4-[4-(phenyl)-2-[3-[3-fluoro-5-(3,4,5,6-tetrahydro-4-hydroxy-2H-pyran-4-yl)phenoxy]propyn-1-yl]-5-oxazolyl]benzenesulfonamide;

4-[4-(phenyl)-2-[3-[3-(3,4,5,6-tetrahydro-4-hydroxy-2H-pyran-4-yl)benzyloxy]propyn-1-yl]-5-oxazolyl]benzenesulfonamide;

4-[4-(phenyl)-2-[3-[3-fluoro-5-(3,4,5,6-tetrahydro-4-hydroxy-2H-pyran -4-yl)benzyloxy]propyn-1-yl]-5-oxazolyl]benzenesulfonamide;

4-[4-(phenyl)-2-[3-[3-(3,4,5,6-tetrahydro-4-hydroxy-2H-pyran-4-yl)thienyloxy]propyn-1-yl]-5-oxazolyl]benzenesulfonamide;

4-[4-(phenyl)-2-[3-[5-(3,4,5,6-tetrahydro-4-hydroxy-2H-pyran-4-yl)pyridin-3-yloxy]propyn-1-yl]-5-oxazolyl]benzenesulfonamide;

4-[4-(phenyl)-2-[3-[5-(3,4,5,6-tetrahydro-4-hydroxy-2H-pyran-4-yl)pyridin-3-ylmethoxy]propyn-1-yl]-5-oxazolyl]benzenesulfonamide;

4-[4-(phenyl)-2-[3-[6-(3,4,5,6-tetrahydro-4-hydroxy-2H-pyran-4-yl)pyridin-2-ylmethoxy]propyn-1-yl]-5-oxazolyl]benzenesulfonamide;

4-[4-(phenyl)-2-[3-[3-(2,6-dimethyl-3,4,5,6-tetrahydro-4-hydroxy-2H-pyran-4-yl)benzyloxy]propyn-1-yl]-5-oxazolyl]benzenesulfonamide;

4-[4-(phenyl)-2-[3-[2-(3,4,5,6-tetrahydro-4-hydroxy-2H-pyran-4-yl)thiazol-4-ylmethoxy]propyn-1-yl]-5-oxazolyl]benzenesulfonamide;

4-[4-(phenyl)-2-[3-[3-fluoro-5-(1S, 5R 3α-hydroxy-6,8-dioxabicyclo [3.2.1]octanyl)phenoxy]propyn-1-yl]-5-oxazolyl]benzenesulfonamide;

4-[4-(phenyl)-2-[3-[3-(3,4,5,6-tetrahydro-4-methoxy-2H-pyran-4-yl)phenoxy]propyl]-5-oxazolyl]benzenesulfonamide;

4-[4-(phenyl)-5-[4-[4-(methylsulfonyl)phenyl]-2-[3-[3-(3,4,5,6-tetrahydro-4-methoxy-2H-pyran-4-yl)phenoxy]propyl]oxazole;

4-[4-(phenyl)-2-[3-[3-fluoro-5-(3,4,5,6-tetrahydro-4-methoxy-2H-pyran-4-yl)phenoxy]propyl]-5-oxazolyl]benzenesulfonamide;

4-[4-(phenyl)-2-[3-[3-(3,4,5,6-tetrahydro-4-methoxy-2H-pyran-4-yl)benzyloxy]propyl]-5-oxazolyl]benzenesulfonamide;

4-[4-(phenyl)-2-[3-[3-fluoro-5-(3,4,5,6-tetrahydro-4-methoxy-2H-pyran-4-yl)benzyloxy]propyl]-5-oxazolyl]benzenesulfonamide;

4-[4-(phenyl)-2-[3-[3-(3,4,5,6-tetrahydro-4-methoxy-2H-pyran-4-yl)-2-thienyloxy]propyl]-5-oxazolyl]benzenesulfonamide;

4-[4-(phenyl)-2-[3-[5-(3,4,5,6-tetrahydro-4-methoxy-2H-pyran-4-yl)pyridin-3-yloxy]propyl]-5-oxazolyl]benzenesulfonamide;

4-[4-(phenyl)-2-[3-[5-(3,4,5,6-tetrahydro-4-methoxy-2H-pyran-4-yl)pyridin-3-ylmethoxy]propyl]-5-oxazolyl]benzenesulfonamide;

4-[4-(phenyl)-2-[3-[6-(3,4,5,6-tetrahydro-4-methoxy-2H-pyran-4-yl)pyridin-2-ylmethoxy]propyl]-5-oxazolyl]benzenesulfonamide;

4-[4-(phenyl)-2-[3-[3-(2,6-dimethyl-3,4,5,6-tetrahydro-4-methoxy-2H-pyran-4-yl)benzyloxy]propyl]-5-oxazolyl]benzenesulfonamide;

4-[4-(phenyl)-2-[3-[2-(3,4,5,6-tetrahydro-4-methoxy-2H-pyran-4-yl)thiazol -4-ylmethoxy]propyl]-5-oxazolyl]benzenesulfonamide;

4-[4-(phenyl)-2-[3-[3-fluoro-5-(1S, 5R 3α-methoxy-6,8-dioxabicyclo[3.2.1]octanyl)phenoxy]propyl]-5-oxazolyl]benzenesulfonamide;

4-[4-(phenyl)-2-[3-[3-(3,4,5,6-tetrahydro-4-hydroxy-2H-pyran-4-yl)phenoxy]propyl]-5-oxazolyl]benzenesulfonamide;

4-[4-(phenyl)-5-[4-[4-(methylsulfonyl)phenyl]-2-[3-[3-(3,4,5,6-tetrahydro-4-hydroxy-2H-pyran-4-yl)phenoxy]propyl]oxazole;

4-[4-(phenyl)-2-[3-[3-fluoro-5-(3,4,5,6-tetrahydro-4-hydroxy-2H-pyran-4-yl)phenoxy]propyl]-5-oxazolyl]benzenesulfonamide;

4-[4-(phenyl)-2-[3-[3-(3,4,5,6-tetrahydro-4-hydroxy-2H-pyran-4-yl)benzyloxy]propyl]-5-oxazolyl]benzenesulfonamide;

4-[4-(phenyl)-2-[3-[3-fluoro-5-(3,4,5,6-tetrahydro-4-hydroxy-2H-pyran-4-yl)benzyloxy]propyl]-5-oxazolyl]benzenesulfonamide;

4-[4-(phenyl)-2-[3-[3-(3,4,5,6-tetrahydro-4-hydroxy-2H-pyran-4-yl)-2-thienyloxy]propyl]-5-oxazolyl]benzenesulfonamide;

4-[4-(phenyl)-2-[3-[5-(3,4,5,6-tetrahydro-4-hydroxy-2H-pyran-4-yl)pyridin-3-yloxy]propyl]-5-oxazolyl]benzenesulfonamide;

4-[4-(phenyl)-2-[3-[5-(3,4,5,6-tetrahydro-4-hydroxy-2H-pyran-4-yl)pyridin-3-ylmethoxy]propyl]-5-oxazolyl]benzenesulfonamide;

4-[4-(phenyl)-2-[3-[6-(3,4,5,6-tetrahydro-4-hydroxy-2H-pyran-4-yl)pyridin-2-ylmethoxy]propyl]-5-oxazolyl]benzenesulfonamide;

4-[4-(phenyl)-2-[3-[3-(2,6-dimethyl-3,4,5,6-tetrahydro-4-hydroxy-2H-pyran-4-yl)benzyloxy]propyl]-5-oxazolyl]benzenesulfonamide;

4-[4-(phenyl)-2-[3-[2-(3,4,5,6-tetrahydro-4-hydroxy-2H-pyran-4-yl)thiazol-4-ylmethoxy]propyl]-5-oxazolyl]benzenesulfonamide;

4-[4-(phenyl)-2-[3-[3-fluoro-5-(1S, 5R 3α-hydroxy-6,8-dioxabicyclo[3.2.1]octanyl)phenoxy]propyl]-5-oxazolyl]benzenesulfonamide;

4-[4-(phenyl)-2-[2-[3-(3,4,5,6-tetrahydro-4-methoxy-2H-pyran-4-yl)phenoxy]ethyl]-5-oxazolyl]benzenesulfonamide;

4-[4-(phenyl)-5-[4-[4-(methylsulfonyl)phenyl]-2-[2-[3-(3,4,5,6-tetrahydro-4-methoxy-2H-pyran-4-yl)phenoxy]ethyl]oxazole;

4-[4-(phenyl)-2-[2-[3-fluoro-5-(3,4,5,6-tetrahydro-4-methoxy-2H-pyran-4-yl)phenoxy]ethyl]-5-oxazolyl]benzenesulfonamide;

4-[4-(phenyl)-2-[2-[3-(3,4,5,6-tetrahydro-4-methoxy-2H-pyran-4-yl)benzyloxy]ethyl]-5-oxazolyl]benzenesulfonamide;

4-[4-(phenyl)-2-[2-[3-fluoro-5-(3,4,5,6-tetrahydro-4-methoxy-2H-pyran-4-yl)benzyloxy]ethyl]-5-oxazolyl]benzenesulfonamide;

4-[4-(phenyl)-2-[2-[3-(3,4,5,6-tetrahydro-4-methoxy-2H-pyran-4-yl)-5-thienyloxy]ethyl]-5-oxazolyl]benzenesulfonamide;

4-[4-(phenyl)-2-[2-[5-(3,4,5,6-tetrahydro-4-methoxy-2H-pyran-4-yl)pyridin-3-yloxy]ethyl]-5-oxazolyl]benzenesulfonamide;

4-[4-(phenyl)-2-[2-[5-(3,4,5,6-tetrahydro-4-methoxy-2H-pyran-4-yl)pyridin-3-ylmethoxy]ethyl]-5-oxazolyl]benzenesulfonamide;

4-[4-(phenyl)-2-[2-[6-(3,4,5,6-tetrahydro-4-methoxy-2H-pyran-4-yl)pyridin-2-ylmethoxy]ethyl]-5-oxazolyl] benzenesulfonamide;

4-[4-(phenyl)-2-[2-[3-(2,6-dimethyl-3,4,5,6-tetrahydro-4-methoxy-2H-pyran-4-yl)benzyloxy]ethyl]-5-oxazolyl] benzenesulfonamide;

4-[4-(phenyl)-2-[2-[2-(3,4,5,6-tetrahydro-4-methoxy-2H-pyran-4-yl)thiazol-4-ylmethoxy]ethyl]-5-oxazolyl] benzenesulfonamide;

4-[4-(phenyl)-2-[2-[3-fluoro-5-(1S, 5R 3α-methoxy-6,8-dioxabicyclo-[3.2.1]octanyl)phenoxy]ethyl]-5-oxazolyl] benzenesulfonamide;

4-[4-(phenyl)-2-[2-[3-(3,4,5,6-tetrahydro-4-hydroxy-2H-pyran-4-yl)phenoxy]ethyl]-5-oxazolyl] benzenesulfonamide;

4-[4-(phenyl)-5-[4-[4-(methylsulfonyl)phenyl]-2-[2-[3-(3,4,5,6-tetrahydro-4-hydroxy-2H-pyran-4-yl)phenoxy]ethyl] oxazole;

4-[4-(phenyl)-2-[2-[3-fluoro-5-(3,4,5,6-tetrahydro-4-hydroxy-2H-pyran-4-yl)phenoxy]ethyl]-5-oxazolyl] benzenesulfonamide;

4-[4-(phenyl)-2-[2-[3-(3,4,5,6-tetrahydro-4-hydroxy-2H-pyran-4-yl)benzyloxy]ethyl]-5-oxazolyl] benzenesulfonamide;

4-[4-(phenyl)-2-[2-[3-fluoro-5-(3,4,5,6-tetrahydro-4-hydroxy-2H-pyran-4-yl)benzyloxy]ethyl]-5-oxazolyl] benzenesulfonamide;

4-[4-(phenyl)-2-[2-[3-(3,4,5,6-tetrahydro-4-hydroxy-2H-pyran-4-yl)-5-thienyloxy]ethyl]-5-oxazolyl] benzenesulfonamide;

4-[4-(phenyl)-2-[2-[5-(3,4,5,6-tetrahydro-4-hydroxy-2H-pyran-4-yl)pyridin-3-yloxy]ethyl]-5-oxazolyl] benzenesulfonamide;

4-[4-(phenyl)-2-[2-[5-(3,4,5,6-tetrahydro-4-hydroxy-2H-pyran-4-yl)pyridin-3-ylmethoxy]ethyl]-5-oxazolyl] benzenesulfonamide;

4-[4-(phenyl)-2-[2-[6-(3,4,5,6-tetrahydro-4-hydroxy-2H-pyran-4-yl)pyridin-2-ylmethoxy]ethyl]-5-oxazolyl] benzenesulfonamide;

4-[4-(phenyl)-2-[2-[3-(2,6-dimethyl-3,4,5,6-tetrahydro-4-hydroxy-2H-pyran-4-yl)benzyloxy]ethyl]-5-oxazolyl] benzenesulfonamide;

4-[4-(phenyl)-2-[2-[2-(3,4,5,6-tetrahydro-4-hydroxy-2H-pyran-4-yl)thiazol-4-ylmethoxy]ethyl]-5-oxazolyl] benzenesulfonamide;

4-[4-(phenyl)-2-[2-[3-fluoro-5-(1S, 5R 3α-hydroxy-6,8-dioxabicyclo[3.2.1]octanyl)phenoxy]ethyl]-5-oxazolyl] benzenesulfonamide;

4-[4-(phenyl)-2-[1-hydroxy-2-[3-(3,4,5,6-tetrahydro-4-methoxy-2H-pyran-4-yl)phenoxy]ethyl]-5-oxazolyl] benzenesulfonamide;

4-[4-(phenyl)-5-[4-[4-(methylsulfonyl)phenyl]-2-[1-hydroxy-2-[3-(3,4,5,6-tetrahydro-4-methoxy-2H-pyran-4-yl)phenoxy]ethyl]oxazole;

4-[4-(phenyl)-2-[1-hydroxy-2-[3-fluoro-5-(3,4,5,6-tetrahydro-4-methoxy-2H-pyran-4-yl)phenoxy]ethyl-5-oxazolyl]benzenesulfonamide;

4-[4-(phenyl)-2-[1-hydroxy-2-[3-(3,4,5,6-tetrahydro-4-methoxy-2H-pyran-4-yl)benzyloxy]ethyl]-5-oxazolyl] benzenesulfonamide;

4-[4-(phenyl)-2-[1-hydroxy-2-[3-fluoro-5-(3,4,5,6-tetrahydro-4-methoxy-2H -pyran-4-yl)benzyloxy]ethyl]-5-oxazolyl]benzenesulfonamide 4-[4-(phenyl)-2-[1-hydroxy-2-[3-(3,4,5,6-tetrahydro-4-methoxy-2H-pyran-4-yl)thiophenyl]ethyl]-5-oxazolyl] benzenesulfonamide;

4-[4-(phenyl)-2-[1-hydroxy-2-[5-(3,4,5,6-tetrahydro-4-methoxy-2H-pyran-4-yl)pyridin-3-yloxy]ethyl]-5-oxazolyl]benzenesulfonamide;

4-[4-(phenyl)-2-[1-hydroxy-2-[5-(3,4,5,6-tetrahydro-4-methoxy-2H-pyran-4-yl)pyridin-3-ylmethoxy]ethyl]-5-oxazolyl]benzenesulfonamide;

4-[4-(phenyl)-2-[1-hydroxy-2-[6-(3,4,5,6-tetrahydro-4-methoxy-2H -pyran-4-yl)pyridin-2-ylmethoxy]ethyl]-5-oxazolyl]benzenesulfonamide;

4-[4-(phenyl)-2-[1-hydroxy-2-[3-(2,6-dimethyl-3,4,5,6-tetrahydro-4-methoxy-2H -pyran-4-yl)benzyloxy]ethyl]-5- oxazolyl]benzenesulfonamide;

4-[4-(phenyl)-2-[1-hydroxy-2-[2-(3,4,5,6-tetrahydro-4-methoxy-2H-pyran-4-yl)thiazol-4-ylmethoxy]ethyl]-5-oxazolyl]benzenesulfonamide;

4-[4-(phenyl)-2-[1-hydroxy-2-[3-fluoro-5-(1S, 5R 3α-methoxy-6,8-dioxabicyclo[3.2.1]octanyl)phenoxy] ethyl]-5-oxazolyl]benzenesulfonamide;

4-[4-(phenyl)-2-[1-hydroxy-2-[3-(3,4,5,6-tetrahydro-4-hydroxy-2H-pyran-4-yl)phenoxy]ethyl]-5-oxazolyl] benzenesulfonamide;

4-[4-(phenyl)-2-[1-hydroxy-2-[3-fluoro-5-(3,4,5,6-tetrahydro-4-hydroxy-2H-pyran-4-yl)phenoxy]ethyl]-5-oxazolyl]benzenesulfonamide;

4-[4-(phenyl)-2-[1-hydroxy-2-[3-(3,4,5,6-tetrahydro-4-hydroxy-2H-pyran-4-yl)benzyloxy]ethyl]-5-oxazolyl] benzenesulfonamide;

4-[4-(phenyl)-2-[1-hydroxy-2-[3-fluoro-5-(3,4,5,6-tetrahydro-4-hydroxy-2H -pyran-4-yl)benzylomy]ethyl]-5-oxazolyl]benzenesulfonamide;

4-[4-(phenyl)-2-[1-hydroxy-2-[3-(3,4,5,6-tetrahydro-4-hydroxy-2H-pyran-4-yl)thiophenyl]ethyl]-5-oxazolyl] benzenesulfonamide;

4-[4-(phenyl)-2-[1-hydroxy-2-[5-(3,4,5,6-tetrahydro-4-hydroxy-2H-pyran-4-yl)pyridin-3-yloxy]ethyl]-5-oxazolyl]benzenesulfonamide;

4-[4-(phenyl)-2-[1-hydroxy-2-[5-(3,4,5,6-tetrahydro-4-hydroxy-2H-pyran-4-yl)pyridin-3-ylmethoxy]ethyl]-5-oxazolyl]benzenesulfonamide;

4-[4-(phenyl)-2-[1-hydroxy-2-[6-(3,4,5,6-tetrahydro-4-hydroxy-2H-pyran-4-yl)pyridin-2-ylmethoxy]ethyl]-5-oxazolyl]benzenesulfonamide;

4-[4-(phenyl)-2-[1-hydroxy-2-[3-(2,6-dimethyl-3,4,5,6-tetrahydro-4-hydroxy-2H-pyran-4-yl)benzyloxy]ethyl] -5- oxazolyl]benzenesulfonamide;

4-[4-(phenyl)-2-[1-hydroxy-2-[2-(3,4,5,6-tetrahydro-4-hydroxy-2H-pyran-4-yl)thiazol-4-ylmethoxy]ethyl]-5-oxazolyl]benzenesulfonamide;

4-[4-(phenyl)-2-[1-hydroxy-2-[3-fluoro-5-(1S, 5R 3α-hydroxy-6,8-dioxabicyclo[3.2.1]octanyl)phenoxy] ethyl]-5-oxazolyl]benzenesulfonamide;

4-[4-(phenyl)-2-[[3-(3,4,5,6-tetrahydro-4-methoxy-2H-pyran-4-yl)phenoxy]methyl]-5-oxazolyl] benzenesulfonamide;

4-[4-(phenyl)-5-[4-[4-(methylsulfonyl)phenyl]-2-[[3-(3,4,5,6-tetrahydro-4-methoxy-2H-pyran-4-yl)phenoxy]methyl] oxazole;

4-[4-(phenyl)-2-[[3-fluoro-5-(3,4,5,6-tetrahydro-4-methoxy-2H-pyran-4-yl)phenoxy]methyl]-5-oxazolyl] benzenesulfonamide;

4-[4-(phenyl)-2-[[3-(3,4,5,6-tetrahydro-4-methoxy-2H-pyran-4-yl)benzyloxy]methyl]-5-oxazolyl] benzenesulfonamide;

4-[4-(phenyl)-2-[[3-fluoro-5-(3,4,5,6-tetrahydro-4-methoxy-2H-pyran-4-yl)benzyloxy]methyl]-5-oxazolyl] benzenesulfonamide;

4-[4-(phenyl)-2-[[3-(3,4,5,6-tetrahydro-4-methoxy-2H-pyran-4-yl)thiophenyl]methyl]-5-oxazolyl] benzenesulfonamide;

4-[4-(phenyl)-2-[[5-(3,4,5,6-tetrahydro-4-methoxy-2H-pyran-4-yl)pyridin-3-yloxy]methyl]-5-oxazolyl]benzenesulfonamide;

4-[4-(phenyl)-2-[[5-(3,4,5,6-tetrahydro-4-methoxy-2H-pyran-4-yl)pyridin-3-ylmethoxy]methyl]-5-oxazolyl]benzenesulfonamide;

4-[4-(phenyl)-2-[[6 -(3,4,5,6-tetrahydro-4-methoxy-2H-pyran-4-yl)pyridin-2-ylmethoxy]methyl]-5-oxazolyl]benzenesulfonamide;

4-[4-(phenyl)-2-[[3-(2,6-dimethyl-3,4,5,6-tetrahydro-4-methoxy-2H-pyran-4-yl)benzyloxy]methyl]-5-oxazolyl]benzenesulfonamide;

4-[4-(phenyl)-2-[[2-(3,4,5,6-tetrahydro-4-methoxy-2H-pyran-4-yl)thiazol-4-ylmethoxy]methyl]-5-oxazolyl]benzenesulfonamide;

4-[4-(phenyl)-2-[[3-fluoro-5-(1S, 5R 3α-methoxy-6,8-dioxabicyclo[3.2.1]octanyl)phenoxy]methyl]-5-oxazolyl]benzenesulfonamide;

4-[4-(phenyl)-2-[[3-(3,4,5,6-tetrahydro-4-hydroxy-2H-pyran-4-yl)phenoxy]methyl]-5-oxazolyl]benzenesulfonamide;

4-[4-(phenyl)-5-[4-[4-(methylsulfonyl)phenyl]-2-[[3-(3,4,5,6-tetrahydro-4-hydroxy-2H-pyran-4-yl)phenoxy]methyl]oxazole;

4-[4-(phenyl)-2-[[3-fluoro-5-(3,4,5,6-tetrahydro-4-hydroxy-2H-pyran-4-yl)phenoxy]methyl]-5-oxazolyl]benzenesulfonamide;

4-[4-(phenyl)-2-[[3-(3,4,5,6-tetrahydro-4-hydroxy-2H-pyran-4-yl)benzyloxy]methyl]-5-oxazolyl]benzenesulfonamide;

4-[4-(phenyl)-2-[[3-fluoro-5-(3,4,5,6-tetrahydro-4-hydroxy-2H-pyran-4-yl)benzyloxy]methyl]-5-oxazolyl]benzenesulfonamide;

4-[4-(phenyl)-2-[[3-(3,4,5,6-tetrahydro-4-hydroxy-2H-pyran-4-yl)thiophenyl]methyl]-5-oxazolyl]benzenesulfonamide;

4-[4-(phenyl)-2-[[5-(3,4,5,6-tetrahydro-4-hydroxy-2H-pyran-4-yl)pyridin-3-yloxy]methyl]-5-oxazolyl]benzenesulfonamide;

4-[4-(phenyl)-2-[[5-(3,4,5,6-tetrahydro-4-hydroxy-2H-pyran-4-yl)pyridin-3-ylmethoxy]methyl]-5-oxazolyl]benzenesulfonamide;

4-[4-(phenyl)-2-[[6-(3,4,5,6-tetrahydro-4-hydroxy-2H-pyran-4-yl)pyridin-2-ylmethoxy]methyl]-5-oxazolyl]benzenesulfonamide;

4-[4-(phenyl)-2-[[3-(2,6-dimethyl-3,4,5,6-tetrahydro-4-hydroxy-2H-pyran-4-yl)benzyloxy]methyl]-5-oxazolyl]benzenesulfonamide;

4-[4-(phenyl)-2-[[2-(3,4,5,6-tetrahydro-4-hydroxy-2H-pyran-4-yl)thiazol-4-ylmethoxy]methyl]-5-oxazolyl]benzenesulfonamide;

4-[4-(phenyl)-2-[[3-fluoro-5-(1S, 5R 3α-hydroxy-6,8-dioxabicyclo[3.2.1]octanyl)phenoxy]methyl]-5-oxazolyl]benzenesulfonamide;

4-[4-(phenyl)-2-[3-[3-(3,4,5,6-tetrahydro-4-methoxy-2H-pyran-4-yl)phenoxy](E-propen)-1-yl]-5-oxazolyl]benzenesulfonamide;

4-[4-(phenyl)-5-[4-[4-(methylsulfonyl)phenyl]-2-[3-[3-(3,4,5,6-tetrahydro-4-methoxy-2H-pyran-4-yl)phenoxy](E & Z-propen)-1-yl]oxazole;

4-[4-(phenyl)-2-[3-[3-fluoro-5-(3,4,5,6-tetrahydro-4-methoxy-2H -pyran-4-yl)phenoxy](Z-propen)-1-yl]-5-oxazolyl]benzenesulfonamide;

4-[4-(phenyl)-2-[3-[3-(3,4,5,6-tetrahydro-4-methoxy-2H-pyran-4-yl)benzyloxy](Z-propen)-1-yl]-5-oxazolyl]benzenesulfonamide;

4-[4-(phenyl)-2-[3-[3-fluoro-5-(3,4,5,6-tetrahydro-4-methoxy-2H-pyran-4-yl)benzyloxy](Z-propen)-1-yl]-5-oxazolyl]benzenesulfonamide;

4-[4-(phenyl)-2-[3-[3-(3,4,5,6-tetrahydro-4-methoxy-2H-pyran-4-yl)thiophenyl](E-propen)-1-yl]-5-oxazolyl]benzenesulfonamide;

4-[4-(phenyl)-2-[3-[5-(3,4,5,6-tetrahydro-4-methoxy-2H-pyran-4-yl)pyridin-3-yloxy](Z-propen)-1-yl]-5-oxazolyl]benzenesulfonamide;

4-[4-(phenyl)-2-[3-[5-(3,4,5,6-tetrahydro-4-methoxy-2H-pyran-4-yl)pyridin-3-ylmethoxy](E-propen)-1-yl]-5-oxazolyl]benzenesulfonamide;

4-[4-(phenyl)-2-[3-[6-(3,4,5,6-tetrahydro-4-methoxy-2H-pyran-4-yl)pyridin-2-ylmethoxy](Z-propen)-1-yl]-5-oxazolyl]benzenesulfonamide;

4-[4-(phenyl)-2-[3-[3-(2,6-dimethyl-3,4,5,6-tetrahydro-4-methoxy-2H-pyran-4-yl)benzyloxy](Z-propen)-1-yl]-5-oxazolyl]benzenesulfonamide;

4-[4-(phenyl)-2-[3-[2-(3,4,5,6-tetrahydro-4-methoxy-2H-pyran-4-yl)thiazol-4-ylmethoxy](Z-propen)-1-yl]-5-oxazolyl]benzenesulfonamide;

4-[4-(phenyl)-2-[3-[3-fluoro-5-(1S, 5R 3α-methoxy-6,8-dioxabicyclo[3.2.1]octanyl)phenoxy](Z-propen)-1-yl]-5-oxazolyl]benzenesulfonamide;

4-[4-(phenyl)-2-[3-[3-(3,4,5,6-tetrahydro-4-hydroxy-2H-pyran-4-yl)phenoxy](E-propen)-1-yl]-5-oxazolyl]benzenesulfonamide;

4-[4-(phenyl)-5-[4-[4-(methylsulfonyl)phenyl]-2-[3-[3-(3,4,5,6-tetrahydro-4-hydroxy-2H-pyran-4-yl)phenoxy](E-propen)-1-yl]oxazole;

4-[4-(phenyl)-2-[3-[3-fluoro-5-(3,4,5,6-tetrahydro-4-hydroxy-2H-pyran-4-yl)phenoxy](Z-propen)-1-yl]-5-oxazolyl]benzenesulfonamide;

4-[4-(phenyl)-2-[3-[3-(3,4,5,6-tetrahydro-4-hydroxy-2H-pyran-4-yl)benzyloxy](E-propen)-1-yl]-5-oxazolyl]benzenesulfonamide;

4-[4-(phenyl)-2-[3-[3-fluoro-5-(3,4,5,6-tetrahydro-4-hydroxy-2H-pyran-4-yl)benzyloxy](Z-propen)-1-yl]-5-oxazolyl]benzenesulfonamide;

4-[4-(phenyl)-2-[3-[3-(3,4,5,6-tetrahydro-4-hydroxy-2H-pyran-4-yl)thiophenyl](Z-propen)-1-yl]-5-oxazolyl]benzenesulfonamide;

4-[4-(phenyl)-2-[3-[5-(3,4,5,6-tetrahydro-4-hydroxy-2H-pyran-4-yl)pyridin-3-yloxy](Z-propen)-1-yl]-5-oxazolyl]benzenesulfonamide;

4-[4-(phenyl)-2-[3-[5-(3,4,5,6-tetrahydro-4-hydroxy-2H-pyran-4-yl)pyridin-3-ylmethoxy](Z-propen)-1-yl]-5-oxazolyl]benzenesulfonamide;

4-[4-(phenyl)-2-[3-[6-(3,4,5,6-tetrahydro-4-hydroxy-2H-pyran-4-yl)pyridin-2-ylmethoxy](E-propen)-1-yl]-5-oxazolyl]benzenesulfonamide;

4-[4-(phenyl)-2-[3-[3-(2,6-dimethyl-3,4,5,6-tetrahydro-4-hydroxy-2H-pyran-4-yl)benzyloxy](E-propen)-1-yl]-5-oxazolyl]benzenesulfonamide;

4-[4-(phenyl)-2-[3-[2-(3,4,5,6-tetrahydro-4-hydroxy-2H-pyran-4-yl)thiazol-4-ylmethoxy](Z-propen)-1-yl]-5-oxazolyl]benzenesulfonamide;

4-[4-(phenyl)-2-[3-[3-fluoro-5-(1S, 5R 3α-hydroxy-6,8-dioxabicyclo[3.2.1]octanyl)phenoxy](E-propen)-1-yl]-5-oxazolyl]benzenesulfonamide;

4-[4-(phenyl)-2-[[3-(3,4,5,6-tetrahydro-4-methoxy-2H-pyran-4-yl)phenoxy]-1,2,3-triazol-4-ylmethyl-5-]-5-oxazolyl]benzenesulfonamide;

4-[4-(phenyl)-5-[4-[4-(methylsulfonyl)phenyl]-2-[[3-(3,4,5,6-tetrahydro-4-methoxy-2H-pyran-4-yl)phenoxy]-1,2,3-triazol-4-ylmethyl-5-]-5-oxazolyl]benzenesulfonamide;

4-[4-(phenyl)-2-[[3-fluoro-5-(3,4,5,6-tetrahydro-4-methoxy-2H-pyran-4-yl)phenoxy]-1,2,3-triazol-4-ylmethyl -5-]-5-oxazolyl]benzenesulfonamide;

4-[4-(phenyl)-2-[[3-(3,4,5,6-tetrahydro-4-methoxy-2H-pyran-4-yl)benzyloxy]-1,2,3-triazol-4-ylmethyl-5-]-5-oxazolyl]benzenesulfonamide;

4-[4-(phenyl)-2-[[3-fluoro-5-(3,4,5,6-tetrahydro-4-methoxy-2H-pyran-4-yl)benzyloxy]-1,2,3-triazol-4-ylmethyl-5-]-5-oxazolyl]benzenesulfonamide;

4-[4-(phenyl)-2-[[3-(3,4,5,6-tetrahydro-4-methoxy-2H-pyran-4-yl)thiophenyl]-1,2,3-triazol-4-ylmethyl-5-5-oxazolyl]benzenesulfonamide;

4-[4-(phenyl)-2-[[5-(3,4,5,6-tetrahydro-4-methoxy-2H-pyran-4-yl)pyridin-3-yloxy]-1,2,3-triazol-4-ylmethyl-5-]-5-oxazolyl]benzenesulfonamide;

4-[4-(phenyl)-2-[[5-(3,4,5,6-tetrahydro-4-methoxy-2H-pyran-4-yl)pyridin-3-ylmethoxy]-1,2,3-triazol-4-ylmethyl-5-]-5-oxazolyl]benzenesulfonamide;

4-[4-(phenyl)-2-[[6-(3,4,5,6-tetrahydro-4-methoxy-2H-pyran-4-yl)pyridin-2-ylmethoxy]-1,2,3- triazol-4-ylmethyl-5-]-5-oxazolyl]benzenesulfonamide;

4-[4-(phenyl)-2-[[3-(2,6-dimethyl-3,4,5,6-tetrahydro-4-methoxy-2H-pyran-4-yl)benzyloxy]-1,2,3-triazol-4-ylmethyl -5-]-5-oxazolyl]benzenesulfonamide;

4-[4-(phenyl)-2-[[2-(3,4,5,6-tetrahydro-4-methoxy-2H-pyran-4-yl)thiazol-4-ylmethoxy]-1,2,3-triazol-4-ylmethyl-5-]-5-oxazolyl]benzenesulfonamide;

4-[4-(phenyl)-2-[[3-fluoro-5-(1S, 5R 3α-methoxy-6,8-dioxabicyclo[3.2.1]octanyl)phenoxy]-1,2,3-triazol-4-ylmethyl -5-]-5-oxazolyl]benzenesulfonamide;

4-[4-(phenyl)-2-[[3-(3,4,5,6-tetrahydro-4-hydroxy-2H-pyran-4-yl)phenoxy]-1,2,3-triazol-4-ylmethyl-5-]-5-oxazolyl]benzenesulfonamide;

4-[4-(phenyl)-5-[4-[4-(methylsulfonyl)phenyl]-2-[[3-(3,4,5,6-tetrahydro-4-hydroxy-2H-pyran-4-yl)phenoxy]-1,2,3-triazol-4-ylmethyl-5-]oxazole;

4-[4-(phenyl)-2-[[3-fluoro-5-(3,4,5,6-tetrahydro-4-hydroxy-2H-pyran-4-yl)phenoxy]-1,2,3-triazol-4-ylmethyl-5-]-5-oxazolyl]benzenesulfonamide;

4-[4-(phenyl)-2-[[3-(3,4,5,6-tetrahydro-4-hydroxy-2H-pyran-4-yl)benzyloxy]-1,2,3-triazol-4-ylmethyl-5-]-5-oxazolyl]benzenesulfonamide;

4-[4-(phenyl)-2-[[3-fluoro-5-(3,4,5,6-tetrahydro-4-hydroxy-2H-pyran-4-yl)benzyloxy]-1,2,3-triazol-4-ylmethyl-5-]-5-oxazolyl]benzenesulfonamide;

4-[4-(phenyl)-2-[[3-(3,4,5,6-tetrahydro-4-hydroxy-2H-pyran-4-yl)thiophenyl]-1,2,3-triazol-4-ylmethyl-5-5-oxazolyl]benzenesulfonamide;

4-[4-(phenyl)-2-[[5-(3,4,5,6-tetrahydro-4-hydroxy-2H-pyran-4-yl)pyridin-3-yloxy]-1,2,3-triazol-4-ylmethyl-5-]-5-oxazolyl]benzenesulfonamide;

4-[4-(phenyl)-2-[[5-(3,4,5,6-tetrahydro-4-hydroxy-2H-pyran-4-yl)pyridin-3-ylmethoxy]-1,2,3-triazol-4-ylmethyl-5-]-5-oxazolyl]benzenesulfonamide;

4-[4-(phenyl)-2-[[6-(3,4,5,6-tetrahydro-4-hydroxy-2H-pyran-4-yl)pyridin-2-ylmethoxy]-1,2,3-triazol-4-ylmethyl -5-]-5-oxazolyl]benzenesulfonamide;

4-[4-(phenyl)-2-[[3-(2,6-dimethyl-3,4,5,6-tetrahydro-4-hydroxy-2H-pyran-4-yl)benzyloxy]-1,2,3-triazol-4-ylmethyl-5-]-5-oxazolyl]benzenesulfonamide;

4-[4-(phenyl)-2-[[2-(3,4,5,6-tetrahydro-4-hydroxy-2H-pyran-4-yl)thiazol-4-ylmethoxy]-1,2,3-triazol-4-ylmethyl-5-]-5-oxazolyl]benzenesulfonamide;

4-[4-(phenyl)-2-[[3-fluoro-5-(1S, 5R 3α-hydroxy-6,8-dioxabicyclo[3.2.1]octanyl)phenoxy]-1,2,3-triazol-4-ylmethyl -5-]-5- oxazolyl]benzenesulfonamide;

4-[4-(phenyl)-2-[[[3-(3,4,5,6-tetrahydro-2H-pyran-4-yl)]E-oximinomethyl]phenoxy]acetyl]-5-oxazolyl]benzenesulfonamide;

4-[4-(phenyl)-2-[[[3-(3,4,5,6-tetrahydro-2H-pyran-4-yl)]Z-oximinomethyl]phenoxy]acetyl]-5-oxazolyl]benzenesulfonamide;

4-[4-(phenyl)-2-[[E-O-methyl-[3-(3,4,5,6-tetrahydro-2H-pyran-4-yl)]oximinomethyl]phenoxy]acetyl]-5-oxazolyl]benzenesulfonamide;

4-[4-(phenyl)-2-[[Z-O-methyl-[3-(3,4,5,6-tetrahydro-2H-pyran-4-yl)]oximinomethyl]phenoxy]acetyl]-5-oxazolyl]benzenesulfonamide;

4-[4-(phenyl)-2-[3-[[3-(3,4,5,6-tetrahydro-2H-pyran-4-yl)]Z-oximinomethyl]phenoxy]propyn-1-yl]-5-oxazolyl]benzenesulfonamide;

4-[4-(phenyl)-2-[3-[[3-(3,4,5,6-tetrahydro-2H-pyran-4-yl)]E-oximinomethyl]phenoxy]propyn-1-yl]-5-oxazolyl]benzenesulfonamide;

4-[4-(phenyl)-2-[3-[E-O-methyl-[3-(3,4,5,6-tetrahydro-2H-pyran-4-yl)]oximinomethyl]phenoxy]propyn-1-yl]-5-oxazolyl]benzenesulfonamide;

4-[4-(phenyl)-2-[3-[Z-O-methyl-[3-(3,4,5,6 -tetrahydro-2H-pyran-4-yl)]oximinomethyl]phenoxy]propyn-1-yl]-5-oxazolyl]benzenesulfonamide;

4-[4-(phenyl)-2-[3-[3-(3,4,5,6-tetrahydro-4-methoxy-2H-pyran-4-yl)phenyl]propyn-1-yl]-5-oxazolyl]benzenesulfonamide;

4-[4-(phenyl)-5-[4-[4-(methylsulfonyl)phenyl]-2-[3-[3-(3,4,5,6-tetrahydro-4-methoxy-2H-pyran-4-yl)phenyl]propyn-1-yl]oxazole;

4-[4-(phenyl)-2-[3-[3-fluoro-5-(3,4,5,6-tetrahydro-4-methoxy-2H-pyran-4-yl)phenyl]propyn-1-yl]-5-oxazolyl]benzenesulfonamide;

4-[4-(phenyl)-2-[3-[5-(3,4,5,6-tetrahydro-4-methoxy-2H-pyran-4-yl)pyridin-3-yl]propyn-1-yl]-5-oxazolyl]benzenesulfonamide;

4-[4-(phenyl)-2-[3-[3-(2,6-dimethyl-3,4,5,6-tetrahydro-4-methoxy-2H-pyran-4-yl)phenyl]propyn-1-yl]-5-oxazolyl]benzenesulfonamide;

4-[4-(phenyl)-2-[3-[2-(3,4,5,6-tetrahydro-4-methoxy-2H-pyran-4-yl)thiazol-4-yl]propyn-1-yl]-5-oxazolyl]benzenesulfonamide;

4-[4-(phenyl)-2-[3-[3-fluoro-5-(1S, 5R 3α-methoxy-6,8-dioxabicyclo[3.2.1]octanyl)phenyl]propyn-1-yl]-5-oxazolyl]benzenesulfonamide;

4-[4-(phenyl)-2-[3-[3-(3,4,5,6-tetrahydro-4-hydroxy-2H-pyran-4-yl)phenyl]propyn-1-yl]-5-oxazolyl]benzenesulfonamide;

4-[4-(phenyl)-5-[4-[4-(methylsulfonyl)phenyl]-2-[3-[3-(3,4,5,6-tetrahydro-4-hydroxy-2H-pyran-4-yl)phenyl]propyn-1-yl]oxazole;

4-[4-(phenyl)-2-[3-[3-fluoro-5-(3,4,5,6-tetrahydro-4-hydroxy-2H-pyran-4-yl)phenyl]propyn-1-yl]-5-oxazolyl]benzenesulfonamide;

4-[4-(phenyl)-2-[3-[5-(3,4,5,6-tetrahydro-4-hydroxy-2H-pyran-4-yl)pyridin-3-yl]propyn-1-yl]-5-oxazolyl]benzenesulfonamide;

4-[4-(phenyl)-2-[3-[3-(2,6-dimethyl-3,4,5,6-tetrahydro-4-hydroxy-2H-pyran-4-yl)phenyl]propyn-1-yl]-5-oxazolyl]benzenesulfonamide;

4-[4-(phenyl)-2-[3-[2-(3,4,5,6-tetrahydro-4-hydroxy-2H-pyran-4-yl)thiazol-4-yl]propyn-1-yl]-5-oxazolyl]benzenesulfonamide;

4-[4-(phenyl)-2-[3-[3-fluoro-5-(1S, 5R 3α-hydroxy-6,8-dioxabicyclo[3.2.1]octanyl)phenyl]propyn-1-yl]-5-oxazolyl]benzenesulfonamide;

4-[4-(phenyl)-2-[3-[3-(3,4,5,6-tetrahydro-4-methoxy-2H-pyran-4-yl)phenyl]propyl]-5-oxazolyl]benzenesulfonamide;

4-[4-(phenyl)-5-[4-[4-(methylsulfonyl)phenyl]-2-[3-[3-(3,4,5,6-tetrahydro-4-methoxy-2H-pyran-4-yl)phenyl]propyl]oxazole;

4-[4-(phenyl)-2-[3-[3-fluoro-5-(3,4,5,6-tetrahydro-4-methoxy-2H-pyran-4-yl)phenyl]propyl]-5-oxazolyl]benzenesulfonamide;

4-[4-(phenyl)-2-[3-[5-(3,4,5,6-tetrahydro-4-methoxy-2H-pyran-4-yl)pyridin-3-yl]propyl]-5-oxazolyl]benzenesulfonamide;

4-[4-(phenyl)-2-[3-[3-(2,6-dimethyl-3,4,5,6-tetrahydro-4-methoxy-2H-pyran-4-yl)phenyl]propyl]-5-oxazolyl] benzenesulfonamide;

4-[4-(phenyl)-2-[3-[2-(3,4,5,6-tetrahydro-4-methoxy-2H-pyran-4-yl)thiazol-4-yl]propyl]-5-oxazolyl] benzenesulfonamide;

4-[4-(phenyl)-2-[3-[3-fluoro-5-(1S, 5R 3α-methoxy-6,8-dioxabicyclo[3.2.1]octanyl)phenyl]propyl]-5-oxazolyl] benzenesulfonamide;

4-[4-(phenyl)-2-[3-[3-(3,4,5,6-tetrahydro-4-hydroxy-2H-pyran-4-yl)phenyl]propyl]-5-oxazolyl] benzenesulfonamide;

4-[4-(phenyl)-5-[4-[4-(methylsulfonyl)phenyl]-2-[3-[3-(3,4,5,6-tetrahydro-4-hydroxy-2H-pyran-4-yl)phenyl]propyl] oxazole;

4-[4-(phenyl)-2-[3-[3-fluoro-5-(3,4,5,6-tetrahydro-4-hydroxy-2H-pyran-4-yl)phenyl]propyl]-5-oxazolyl] benzenesulfonamide;

4-[4-(phenyl)-2-[3-[5-(3,4,5,6-tetrahydro-4-hydroxy-2H-pyran-4-yl)pyridin-3-yl]propyl]-5-oxazolyl] benzenesulfonamide;

4-[4-(phenyl)-2-[3-[3-(2,6-dimethyl-3,4,5,6-tetrahydro-4-hydroxy-2H-pyran-4-yl)phenyl]propyl]-5-oxazolyl] benzenesulfonamide;

4-[4-(phenyl)-2-[3-[2-(3,4,5,6-tetrahydro-4-hydroxy-2H-pyran-4-yl)thiazol-4-yl]propyl]-5-oxazolyl] benzenesulfonamide; and 4-[4-(phenyl)-2-[3-[3-fluoro-5-(1S, 5R 3α-hydroxy-6,8-dioxabicyclo[3.2.1]octanyl)phenyl]propyn-1-yl]-5-oxazolyl]benzenesulfonamide.

The term "hydrido" denotes a single hydrogen atom (H). This hydrido radical may be attached, for example, to an oxygen atom to form a hydroxyl radical or two hydrido radicals may be attached to a carbon atom to form a methylene (—$CH_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "alkenyl" embraces linear or branched radicals having at least one carbon—carbon double bond of two to about twenty carbon atoms or, preferably, one to about twelve carbon atoms. More preferred alkyl radicals are "lower alkenyl" radicals having two to about six carbon atoms. Examples of alkenyl radicals include ethenyl, propenyl, allyl, propenyl, butenyl and 4-methylbutenyl. The term "alkynyl" denotes linear or branched radicals having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like. The terms "alkenyl", "lower alkenyl", embrace radicals having "cis" and "trans" orientations, or alternatively, "E" and "Z" orientations. The term "cycloalkyl" embraces saturated carbocyclic radicals having three to twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. The term "cycloalkenyl" embraces partially unsaturated carbocyclic radicals having three to twelve carbon atoms. More preferred cycloalkenyl radicals are "lower cycloalkenyl" radicals having four to about eight carbon atoms. Examples of such radicals include cyclobutenyl, cyclopentenyl and cyclohexenyl. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The term "cyanoalkyl" embraces linear or branched alkyl radicals having one to about ten carbon atoms any one of which may be substituted with one or more cyano radicals. More preferred cyanoalkyl radicals are "lower cyanoalkyl" radicals having one to six carbon atoms and one or more cyano radicals. Examples of such radicals include cyanomethyl, cyanoethyl, cyanopropyl, cyanobutyl and cyanohexyl. The terms "alkoxy" and "alkyloxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" embraces alkyl radicals having one or more alkoxy radicals attached to the alkyl radical, that is, to form monoalkoxyalkyl and dialkoxyalkyl radicals. The "alkoxy" radicals may be further substituted with one or more halo atoms, such as fluoro, chloro or bromo, to provide haloalkoxy radicals, or with hydroxyl radicals to from "hydroxyalkyloxy" radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. More preferred hydroxyalkyloxy radicals are "lower hydroxyalkyloxy" radicals having alkyl poriotns of 1 to 6 carbons. The term "alkenyloxy" embraces radicals having alkenyl portions of two to about ten carbon atoms attached to an oxygen atom. More preferred alkenyloxy radicals are "lower alkenyloxy" radicals having two to six carbon atoms. The term "alkynyloxy" embraces radicals having alkynyl portions of two to about ten carbon atoms attached to an oxygen atom. More preferred alkynyloxy radicals are "lower alkynyloxy" radicals having two to six carbon atoms. Examples of such lower alkynyloxy radicals include propynyloxy, and butynyloxy. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl. The term "heterocyclo" embraces saturated, partially unsaturated and unsaturated heteroatom-containing ring-shaped radicals, where the heteroatoms may be selected from nitrogen, sulfur and oxygen. Examples of saturated heterocyclo radicals include saturated 3 to 6-membered heteromonocylic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclo radicals include dihydrothiophene, dihydropyran, dihydrofuran and dihydrothiazole. The term "heteroaryl" embraces unsaturated heterocyclo radicals. Examples of unsaturated heterocyclo radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclo group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b] pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclo group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4- thiadiazolyl, 1,3,4-thiadiazolyl, 1,2,5-thiadiazolyl, etc.) etc.; unsaturated condensed heterocyclo group containing 1 to 2 sulfur atoms and 1 to 3 nitrogen atoms (e.g., benzothiazolyl, benzothiadiazolyl, etc.) and the like. The term also embraces radicals where heterocyclo radicals are fused with aryl radicals. Examples of such fused bicyclic radicals include benzofuran, benzothiophene, and the like. Said "heterocyclo group" may have 1 to 3 substituents such as alkyl, hydroxyl, halo, alkoxy, oxo, amino and alkylamino. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces radicals containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl. The term "oximinoalkoxy" embraces alkyloxy radicals having one to about ten carbon atoms any one of which may be substituted with one or more oximino radicals (—C=NOH). More preferred oximinoalkoxy radicals are "lower oximinoalkoxy" radicals having alkoxy radicals containing one to six carbon atoms. Examples of such radicals include oximinomethoxy, oximinopropoxy, and oximinobutoxy. The term "oximinoalkoxyalkyl" embraces alkyloxyalkyl radicals with alkyl and portions having one to about ten carbon atoms any one of which may be substituted with an oximino radical (—C=NOH). More preferred oximinoalkoxyalkyl radicals are "lower oximinoalkoxyalkyl" radicals having alkyl radicals containing one to six carbon atoms. The terms "(alkyl)oximinoalkoxyalkyl" and "(alkyl)oximinoalkoxy" embrace oximinoalkoxyalkyl and oximinoalkoxy radicals, as defined above, where the oximino portion is substituted on the oxygen atom with alkyl radicals having one to about ten carbon atoms. More preferred oximinoalkoxyalkyl radicals are "lower (alkyl) oximinoalkoxyalkyl" and "lower (alkyl)oximinoalkoxy" radicals having alkyl radicals containing one to six carbon atoms. The term "alkenylthio" embraces radicals containing a linear or branched alkenyl radical, of two to about ten carbon atoms attached to a divalent sulfur atom. More preferred alkenylthio radicals are "lower alkenylthio" radicals having alkenyl radicals of two to six carbon atoms. The term "alkynylthio" embraces radicals containing a linear or branched alkynyl radical, of two to about ten carbon atoms attached to a divalent sulfur atom. More preferred alkynylthio radicals are "lower alkynylthio" radicals having alkynyl radicals of two to six carbon atoms. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —$SO_2$—. "Alkylsulfonyl" embraces alkyl radicals attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals. The terms "sulfamyl", "aminosulfonyl" and "sulfonamidyl" denote $NH_2O_2S$—. The term "acyl" denotes a radical provided by the residue after removal of hydroxyl from an organic acid. Examples of such acyl radicals include alkanoyl and aroyl radicals. Examples of such lower alkanoyl radicals include formyl, acetyl, propionyl, butyryl, isobutyryl, valeryl, isovaleryl, pivaloyl, hexanoyl, trifluoroacetyl. The term "carbonyl", whether used alone or with other terms, such as "alkoxycarbonyl", denotes —(C=O) —. The term "aroyl" embraces aryl radicals with a carbonyl radical as defined above. Examples of aroyl include benzoyl, naphthoyl, and the like and the aryl in said aroyl may be additionally substituted. The terms "carboxy" or "carboxyl", whether used alone or with other terms, such as "carboxyalkyl", denotes —$CO_2H$. The term "carboxyalkyl" embraces alkyl radicals substituted with a carboxy radical.

More preferred are "lower carboxyalkyl" which embrace lower alkyl radicals as defined above, and may be additionally substituted on the alkyl radical with halo. Examples of such lower carboxyalkyl radicals include carboxymethyl, carboxyethyl and carboxypropyl. The term "alkoxycarbonyl" means a radical containing an alkoxy radical, as defined above, attached via an oxygen atom to a carbonyl radical. More preferred are "lower alkoxycarbonyl" radicals with alkyl porions having 1 to 6 carbons. Examples of such lower alkoxycarbonyl (ester) radicals include substituted or unsubstituted methoxycarbonyl, ethoxycarbonyl, propoxycarbonyl, butoxycarbonyl and hexyloxycarbonyl. The terms "alkylcarbonyl", "arylcarbonyl" and "aralkylcarbonyl" include radicals having alkyl, aryl and aralkyl radicals, as defined above, attached via an oxygen atom to a carbonyl radical. Examples of such radicals include substituted or unsubstituted methylcarbonyl, ethylcarbonyl, phenylcarbonyl and benzylcarbonyl. The term "aralkyl" embraces aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable. The term "heteroaralkyl" embraces heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy. The term "aralkoxy" embraces aralkyl radicals attached through an oxygen atom to other radicals. The term "aralkoxyalkyl" embraces aralkoxy radicals attached through an oxygen atom to an alkyl radical. The term "aralkylthio" embraces aralkyl radicals attached to a sulfur atom. The term "aralkylthioalkyl" embraces aralkylthio radicals attached through a sulfur atom to an alkyl radical. The term "heteroaralkoxy" embraces heteroaralkyl radicals attached through an oxygen atom to other radicals. The term "heteroaralkylthio" embraces heteroaralkyl radicals attached through a sulfur atom to other radicals. The term "aminoalkyl" embraces alkyl radicals substituted with amino radicals. More preferred are "lower aminoalkyl" radicals. Examples of such radicals include aminomethyl, aminoethyl, and the like. The term "alkylamino" denotes amino groups which have been substituted with one or two alkyl radicals. Preferred are "lower N-alkylamino" radicals having alkyl porions having 1 to 6 carbon atoms. Suitable lower alkylamino may be mono or dialkylamino such as N-methylamino, N-ethylamino, N,N-dimethylamino, N,N-diethylamino or the like. The term "cycloalkylamino" denotes amino groups which have been substituted with one or two cycloalkyl radicals, as defined above. The term "arylamino" denotes amino groups which have been substituted with one or two aryl radicals, such as N-phenylamino. The "arylamino" radicals may be further substituted on the aryl ring portion of the radical. The term "aralkylamino" embraces aralkyl radicals attached through an nitrogen atom to other radicals. The terms "N-arylaminoalkyl" and "N-aryl-N-alkyl-aminoalkyl" denote amino groups which have been substituted with one aryl radical or one aryl and one alkyl radical, respectively, and having the amino group attached to an alkyl radical. Examples of such radicals include N-phenylaminomethyl and N-phenyl-N-methylaminomethyl. The term "aminocarbonyl" denotes an amide group of the formula —C(=O)NH$_2$. The term "alkylaminocarbonyl" denotes an aminocarbonyl group which has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" "lower N,N-dialkylaminocarbonyl" radicals with lower alkyl portions as defined above. The term "alkylaminocarbonylhaloalkyl" denotes an aminocarbonyl group which has been substituted with one or two alkyl radicals on the amino nitrogen atom, attached to an haloalkyl radical. Preferred are "N-alkylaminocarbonylhaloalkyl" "N,N-alkylaminocarbonylhaloalkyl" radicals. More preferred are "lower N-alkylaminocarbonylhaloalkyl" "lower N,N-alkylaminocarbonylhaloalkyl" radicals with lower alkyl and lower haloalkyl portions as defined above. The term "alkylaminoalkyl" embraces radicals having one or more alkyl radicals attached to an aminoalkyl radical. The term "aryloxyalkyl" embraces radicals having an aryl radicals attached to an alkyl radical through a divalent oxygen atom. The term "arylthioalkyl" embraces radicals having an aryl radicals attached to an alkyl radical through a divalent sulfur atom.

When the above radicals are included as linker moiety "Y" in Formulas I–II, such radicals are divalent radicals. In addition, the orientation of the radicals between "A" and "Ar" are reversible. For example, the term "alkylthio" represents both —CH$_2$S— and —SCH$_2$—, and "carbonylmethyloxy" represents both —C(O)CH$_2$O— and —OCH$_2$C(O)—. For terms such as aralkyl, and heteroarylalkyl, the moiety may be linked to "A" and "Ar" through a divalent alkyl radical, or through the alkyl radical at one end and the aryl or heteroaryl portion at the other. The use of heterocyclo and aryl moieties includes divalent attachment at substitutable sites. The use of a substituted amine group, does not include attachment through a divalent nitrogen atom (i.e., —N(CH$_3$)—) but instead (—N(H)CH$_2$—).

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having or susceptible to such inflammation or disorder a therapeutically-effective amount of a compound of Formula I. The method includes prophylactic or chronic treatment, especially in the case of arthritis and other inflammatory conditions which can lead to deterioration in the joints.

Also included in the family of compounds of Formula I are the stereoisomers and tautomers thereof. Compounds of the present invention can possess one or more asymmetric carbon atoms and are thus capable of existing in the form of optical isomers as well as in the form of racemic or nonracemic mixtures thereof. Accordingly, some of the compounds of this invention may be present in racemic mixtures which are also included in this invention. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting an amine functionality of precursors to compounds of Formula I with an optically pure acid in an activated form or an optically pure isocyanate. Alternatively, diastereomeric derivatives can be prepared by reacting a carboxyl functionality of precursors to compounds of Formula I with an optically pure amine base. The synthesized diastereoisomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclo, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicylic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylgtucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–XXIII, wherein the $R^1$–$R^9$ substituents are as defined for Formula I–II, above, except where further noted.

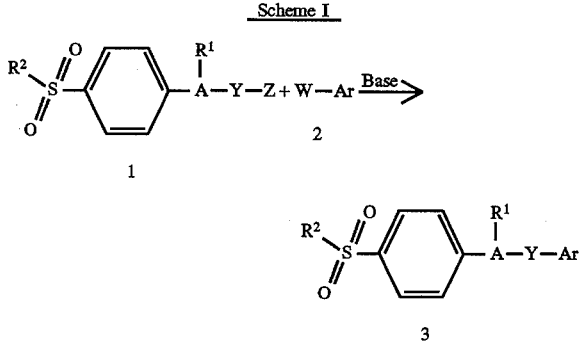

Synthetic Scheme I shows the preparation of sulfonylphenyl derivatives 3, where one of Z or W is a leaving group. A substituted aromatic or heteroaryl 2, such a tetrahydropyran substituted aryl, and a base such as anhydrous potassium carbonate are dissolved in anhydrous solvent such as DMF. A solution of sulfonylphenyl derivative 1 in anhydrous DMF is added and stirred at room temperature to provide the sulfonylphenyl derivatives 3.

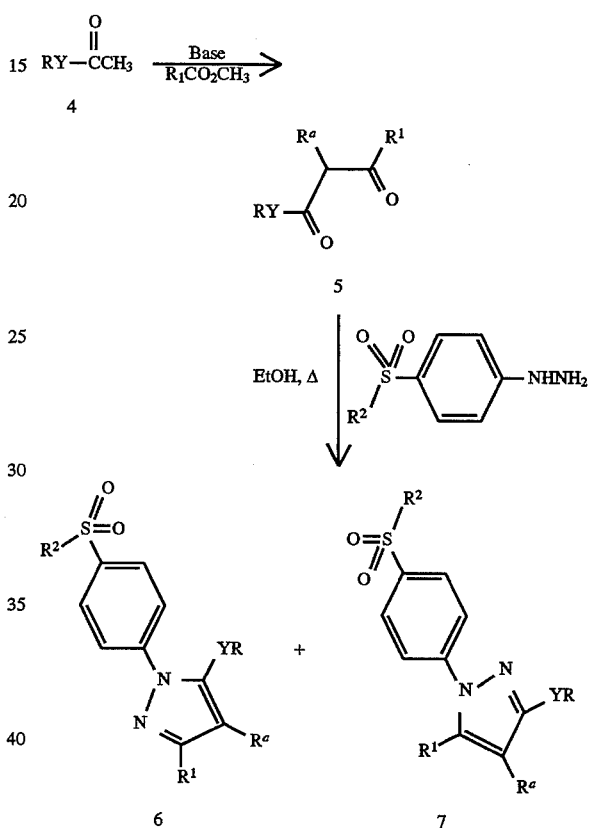

Synthetic Scheme II shows the preparation of pyrazole compounds embraced by Formula I where R is Ar or Z (as defined in Scheme I), and $R^a$ is a radical defined above for the substituents optionally substituted on A. In step 1, ketone 4 is treated with a base, preferably NaOMe or NaH, and an ester, or ester equivalent, to form the intermediate diketone 5 (in the enol form) which is used without further purification. In step 2, diketone 5 in an anhydrous protic solvent, such as absolute ethanol or acetic acid, is treated with the hydrochloride salt or the free base of a substituted hydrazine at reflux to afford a mixture of pyrazoles 6 and 7. Recrystallization from diethyl ether/hexane or chromatography affords 6 usually as a solid. Similar pyrazoles can be prepared by methods described in U.S. Pat. Nos. 4,146,721, 5,051,518, 5,134,142 and 4,914,121 which are incorporated by reference.

Scheme III

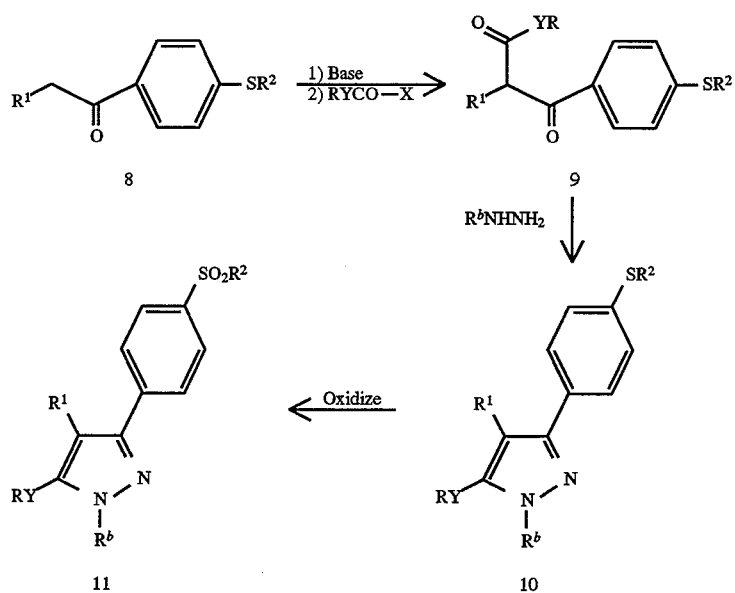

Scheme III shows the four step procedure for forming pyrazoles 11 of the present invention (where $R^b$ is alkyl) from ketones 8. In step 1, ketone 8 is reacted with a base, such as lithium bis(trimethylsilyl)amide or lithium diisopropylamide (LDA) to form the anion. In step 2, the anion is reacted with an acetylating reagent to provide diketone 9. In step 3, the reaction of diketone 9 with hydrazine or a substituted hydrazine, gives pyrazole 10. In step 4, the pyrazole 10 is oxidized with an oxidizing reagent, such as Oxone® (potassium peroxymonosulfate), 3-chloroperbenzoic acid (MCPBA) or hydrogen peroxide, to give a mixture of the desired 3-(alkylsulfonyl)phenyl-pyrazole 11 and the 5-(alkylsulfonyl)phenyl-pyrazole isomer. The desired pyrazole 11, usually a white or pale yellow solid, is obtained in pure form either by chromatography or recrystallization.

Alternatively, diketone 9 can be formed from ketone 8 by treatment with a base, such as sodium hydride, in a solvent, such as dimethylformamide, and further reacting with a nitrile to form an aminoketone. Treatment of the aminoketone with acid forms the diketone 9. Similar pyrazoles can be prepared by methods described in U.S. Pat. No. 3,984,431 which is incorporated by reference.

Scheme IV

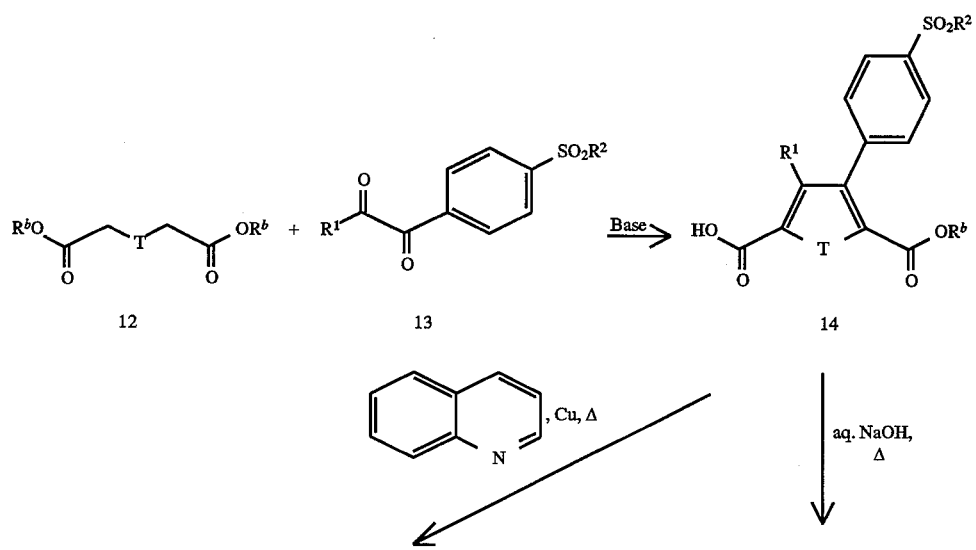

-continued
Scheme IV
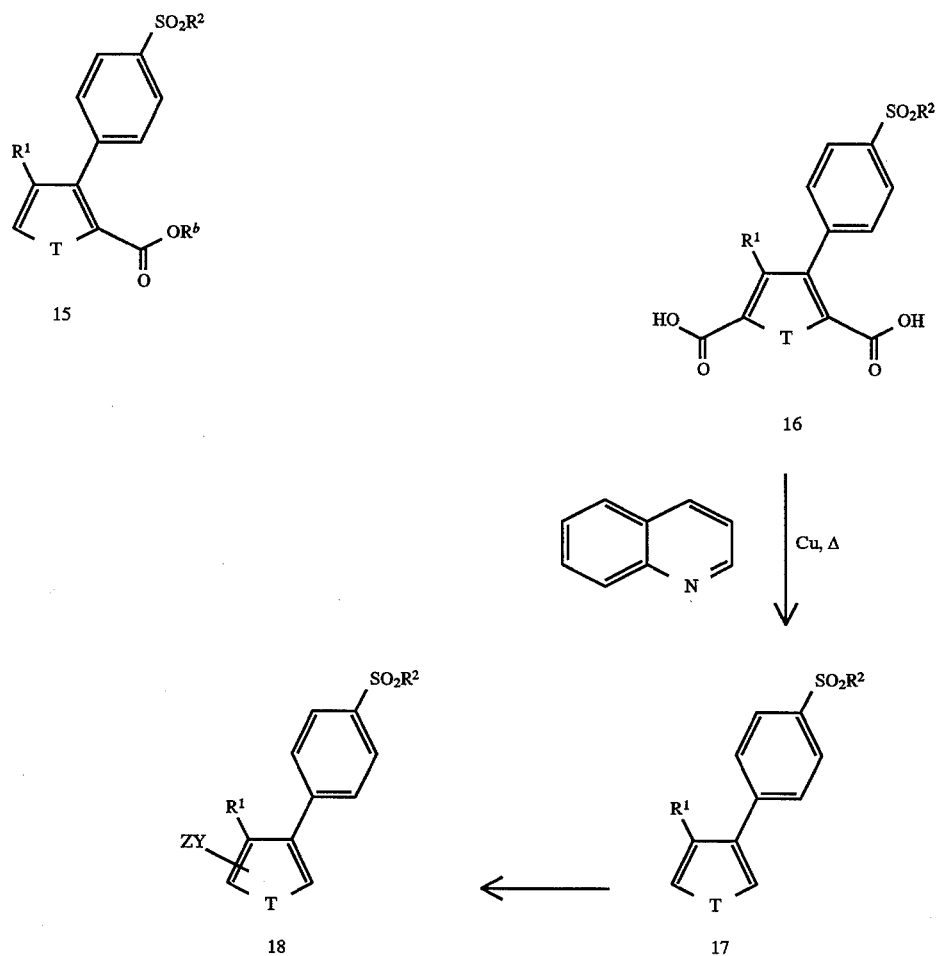
Diaryl/heteroaryl thiophenes (where T is S, and $R^b$ is alkyl) can be prepared by the methods described in U.S. Pat. Nos. 4,427,693, 4,302,461, 4,381,311, 4,590,205, and 4,820,827, and PCT documents WO 00501 and WO94/15932, which are incorporated by reference. Similar pyrroles (where T is N), furanones and furans (where T is O) can be prepared by methods described in PCT documents WO 95/00501 and WO94/15932.
Scheme V
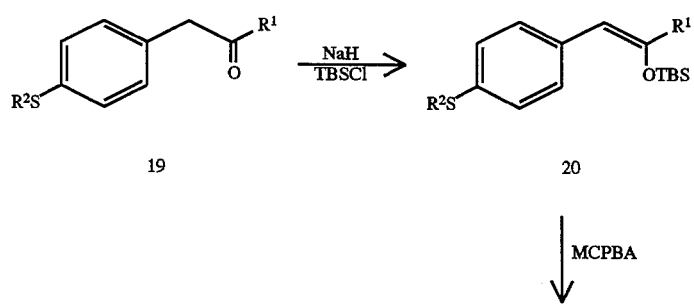

-continued
Scheme V

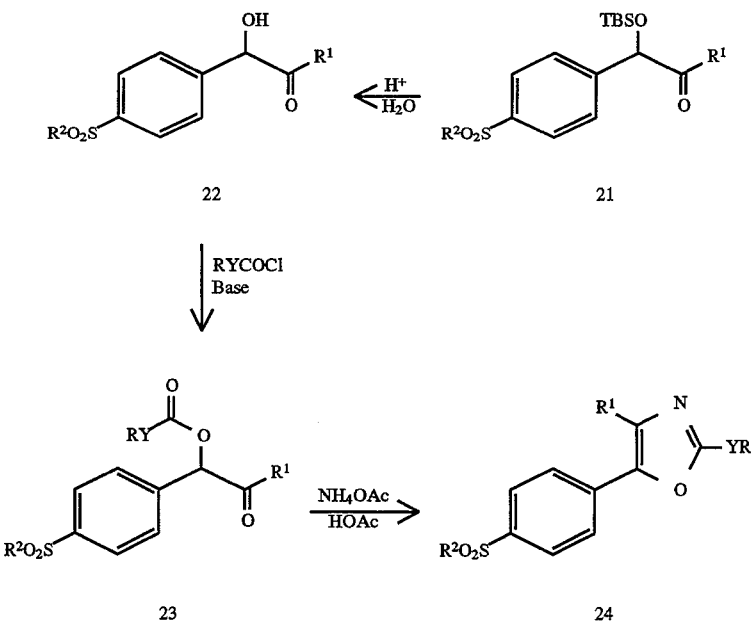

Diaryl/heteroaryl oxazoles can be prepared by the methods described in U.S. Pat. Nos. 3,743,656, 3,644,499 and 3,647,858, and PCT documents WO 95/00501 and WO94/15932, which are incorporated by reference.

Scheme VI

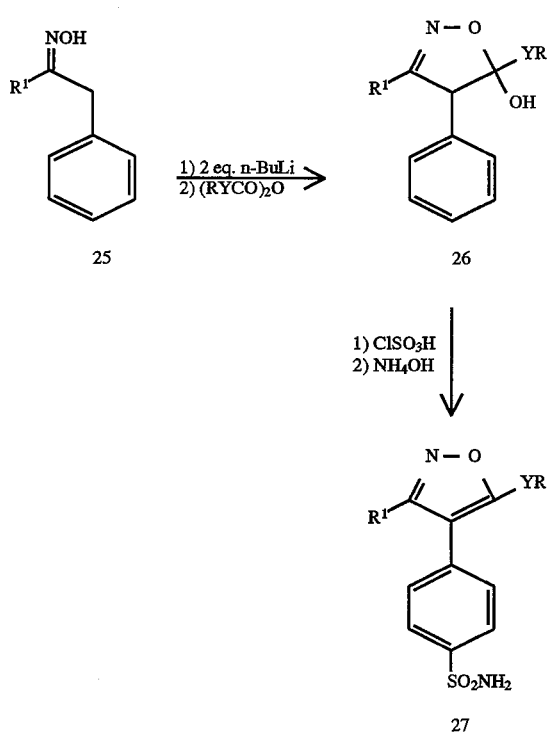

Diaryl/heteroaryl isoxazoles can be prepared by the methods described in PCT documents WO92/05162, and WO92/19604, and European Publication EP 26928 which are incorporated by reference. Sulfonamides 27 can be formed from the hydrated isoxazole 26 in a two step procedure. First, hydrated isoxazole 26 is treated at about 0° C. with two or three equivalents of chlorosulfonic acid to form the corresponding sulfonyl chloride. In step two, the sulfonyl chloride thus formed is treated with concentrated ammonia to provide the sulfonamide derivative 27.

Scheme VII

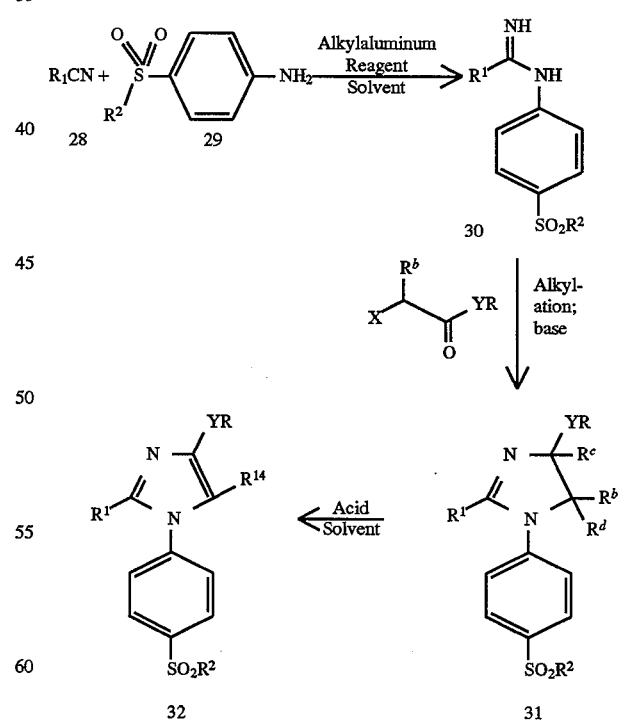

Scheme VII shows the three step preparation of the substituted imidazoles 32 of the present invention. In step 1, the reaction of substituted nitriles ($R^1CN$) 28 with primary phenylamines 29 in the presence of alkylaluminum reagents such as trimethylaluminum, triethylaluminum, dimethylaluminum chloride, diethylaluminum chloride in the presence of inert solvents such as toluene, benzene, and xylene, gives amidines 30. In step 2, the reaction of amidine with 2-haloketones (where X is Br or Cl) in the presence of bases, such as sodium bicarbonate, potassium carbonate, sodium carbonate, potassium bicarbonate or hindered tertiary amines such as N,N'-diisopropylethylamine, gives the 4,5-dihydroimidazoles 31 (where $R^b$ is alkyl, $R^c$ is hydroxyl and $R^d$ is hydrido). Some of the suitable solvents for this reaction are isopropanol, acetone and dimethylformamide. The reaction may be carried out at temperatures of about 20° C. to about 90° C. In step 3, the 4,5-dihydroimidazoles 31 may be dehydrated in the presence of an acid catalyst such as 4-toluenesulfonic acid or mineral acids to form the 1,2-disubstituted imidazoles 32 of the invention. Suitable solvents for this dehydration step are e.g., toluene, xylene and benzene. Trifluoroacetic acid can be used as solvent and catalyst for this dehydration step.

In some cases (e.g., where YR=methyl or phenyl) the intermediate 31 may not be readily isolable. The reaction, under the conditions described above, proceeds to give the targeted imidazoles directly.

Similarly, imidazoles can be prepared having the sulfonylphenyl moiety attached at position 2 and $R^1$ attached at the nitrogen atom at position 1. Diaryl/heteroaryl imidazotes can be prepared by the methods described in U.S. Pat. Nos. 4,822,805, and PCT document WO 93/14082, which are incorporated by reference.

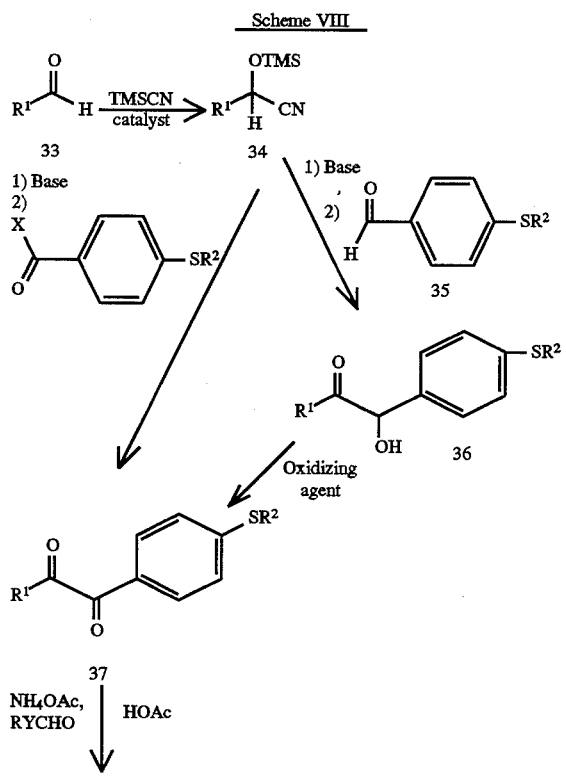

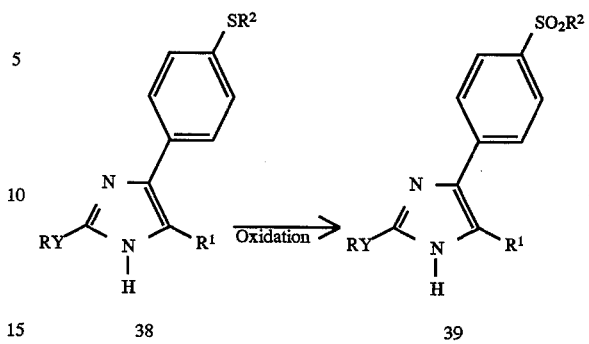

The subject imidazole compounds 39 of this invention may be synthesized according to the sequence outlined in Scheme VIII. Aldehyde 33 may be converted to the protected cyanohydrin 34 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 34 with a strong base followed by treatment with benzaldehyde 35 (where $R^2$ is alkyl) and using both acid and base treatments, in that order, on workup gives benzoin 36. Examples of strong bases suitable for this reaction are lithium diisopropylamide (LDA) and lithium hexamethyldisilazane. Benzoin 36 may be converted to benzil 37 by reaction with a suitable oxidizing agent, such as bismuth oxide or manganese dioxide, or by a Swern oxidation using dimethyl sulfoxide (DMSO) and trifluoroacetic anhydride. Benzil 37 may be obtained directly by reaction of the anion of cyanohydrin 34 with a substituted benzoic acid halide. Any of compounds 36 and 37 may be used as intermediates for conversion to imidazoles 38 (where $R^2$ is alkyl) according to chemical procedures known by those skilled in the art and described by M. R. Grimmett, "Advances in Imidazole Chemistry" in Advances in Heterocyclic Chemistry, 12, 104 (1970). The conversion of 37 to imidazoles 38 is carried out by reaction with ammonium acetate and an appropriate aldehyde (RYCHO) in acetic acid. Benzoin 36 may be converted to imidazoles 38 by reaction with formamide. In addition, benzoin 36 may be converted to imidazoles by first acylating with an appropriate acyl group (RYCO—) and then treating with ammonium hydroxide. Those skilled in the art will recognize that the oxidation of the sulfide (where $R^2$ is methyl) to the sulfone may be carried out at any point along the way beginning with compounds 35, and including oxidation of imidazoles 38, using, for examples, reagents such as hydrogen peroxide in acetic acid, m-chloroperoxybenzoic acid (MCPBA) and potassium peroxymonosulfate (OXONE®).

Diaryl/heteroaryl imidazoles can be prepared by the methods described in U.S. Pat. Nos. 3,707,475, 4,686,231, 4,503,065, 4,472,422, 4,372,964, 4,576,958, 3,901,908, European publication EP 372,445, and PCT document WO 95/00501, which are incorporated by reference.

Scheme IX

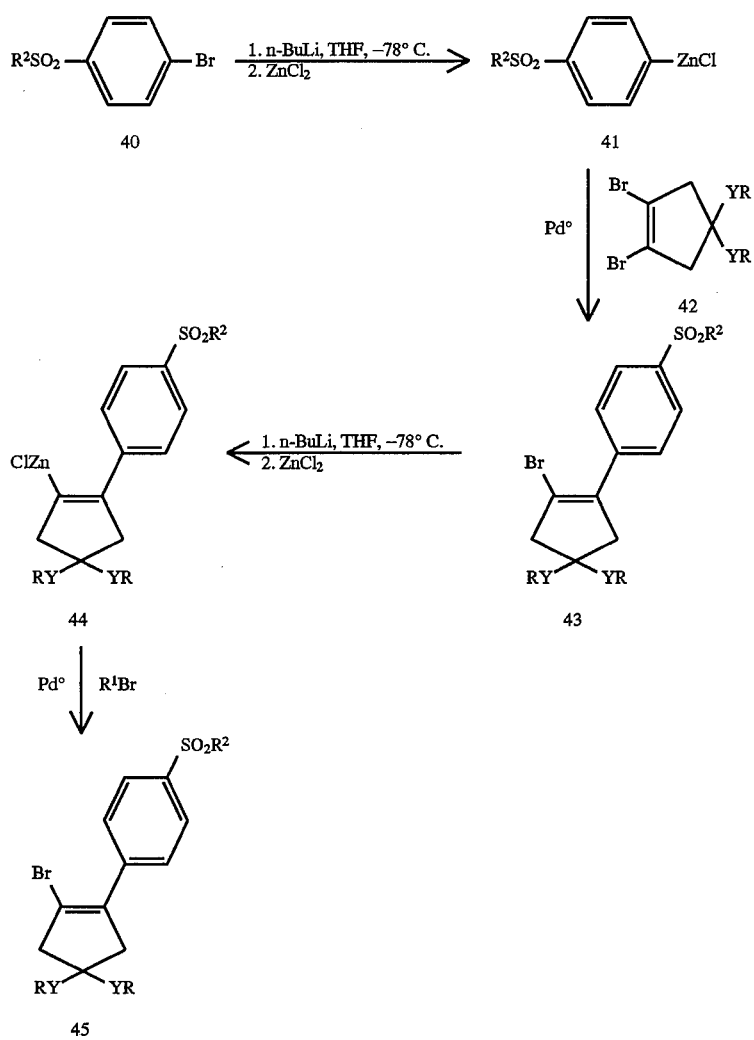

Diaryl/heteroaryl cyclopentenes can be prepared by the methods described in U.S. Pat. No. 5,344,991, and PCT document WO 95/00501, which are incorporated by reference.

Scheme X

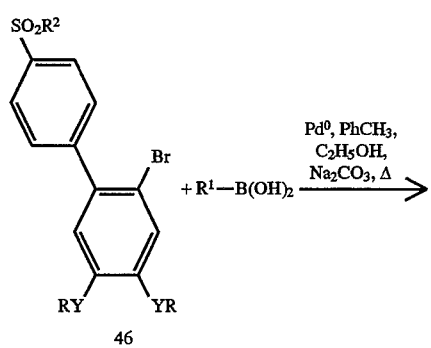

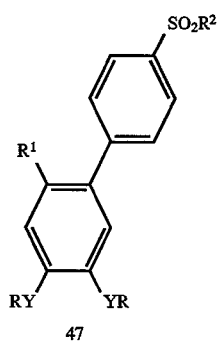

Similarly, Synthetic Scheme X shows the procedure for the preparation of 1,2-diarylbenzene antiinflammatory agents 47 from 2-bromo-biphenyl intermediates 46 (prepared similar to that described in Synthetic Scheme IX) and the appropriate substituted phenylboronic acids. Using a coupling procedure similar to the one developed by Suzuki et al. [*Synth. Commun.*, 11, 513 (1981)], intermediates 46 are reacted with the boronic acids in toluene/ethanol at reflux in the presence of a Pd° catalyst, e.g., tetrakis(triphenylphosphine)palladium(0), and 2M sodium carbonate to give the corresponding 1,2-diarylbenzene antiinflammatory agents 47 of this invention.

Diaryl/heteroaryl thiazoles can be prepared by the methods described in U.S. Pat. No. 4,051,250, 4,632,930, European Application EP 592,664, and PCT document WO 95/00501, which are incorporated by reference. Isothiazoles can be prepared as described in PCT document WO 95/00501.

Scheme XI

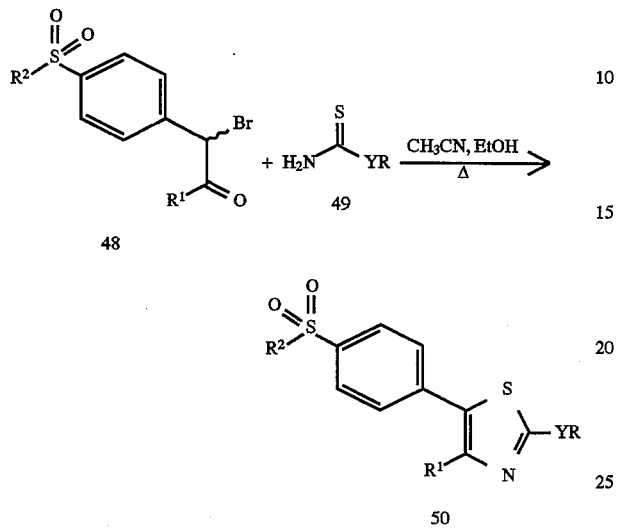

Scheme XII

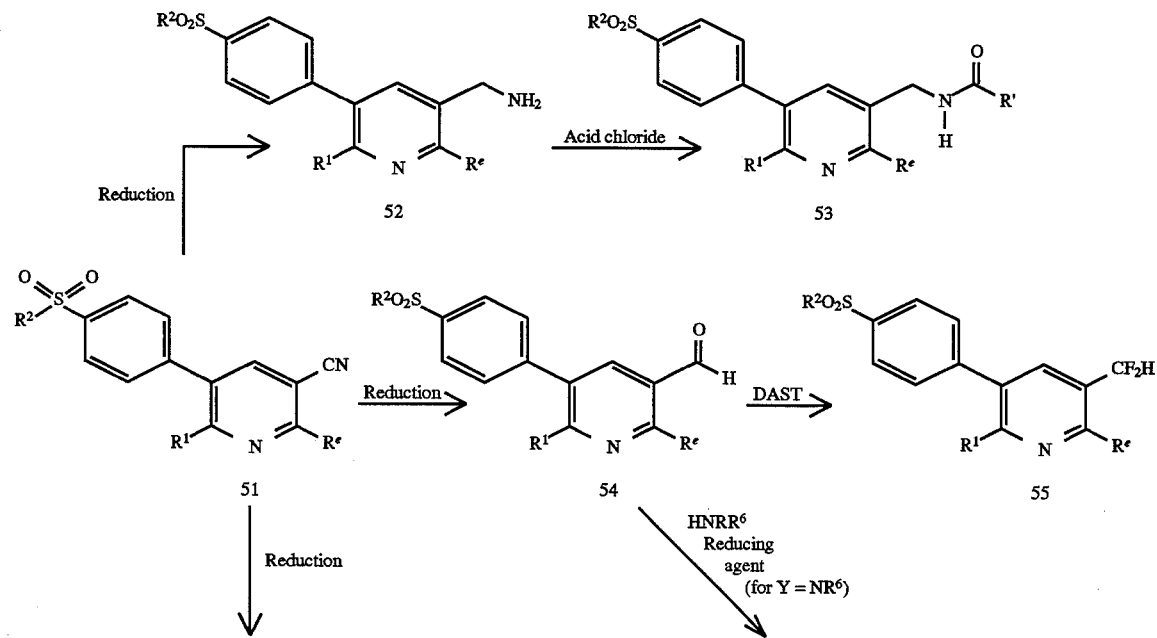

-continued
Scheme XII

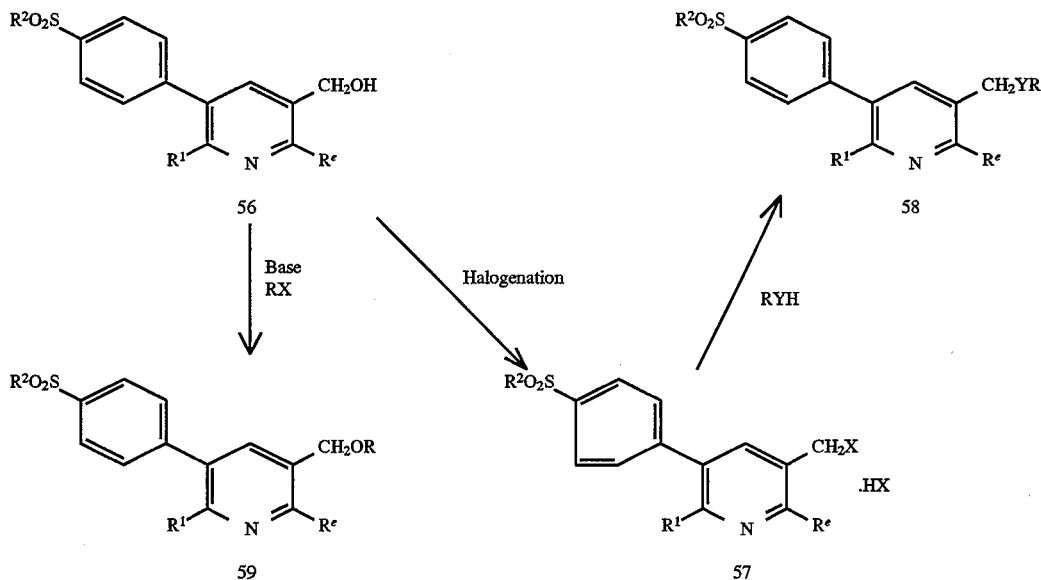

Diaryl/heteroaryl pyridines can be prepared by the methods described in U.S. Pat. Nos. 5,169,857, 4,011,328, and 4,533,666, which are incorporated by reference. For example, Synthetic Scheme XII shows the procedure used to prepare 3-alkylcarbonylaminoalkyl pyridine antiinflammatory agents 53, 3-haloalkyl pyridine antiinflammatory agents 55, 3-hydroxyalkyl pyridine antiinflammatory agents 56, heteroatom substituted 3-alkyl pyridine antiinflammatory agents 58 and 3-aryloxyalkyl pyridine antiinflammatory agents 59 from the corresponding carbonitriles 51. The 3-alkylcarbonylaminoalkyl pyridine antiinflammatory agents 53 (where R' is alkyl) are prepared in a two step procedure from the carbonitriles 51. In step one, the carbonitrile 51 is reduced using reducing agents, such as diisobutyl aluminum hydride (DIBAL) in a solvent such as toluene or boranes in a solvent such as tetrahydrofuran, at room temperature or reflux to form the aminoalkyl pyridine 52. Additional reducing reagent may be added to the solution. In step two, an acid chloride is added to the aminoalkyl pyridine 52 in a solvent such as ethyl ether or tetrahydrofuran and stirred to form the alkylcarbonylaminoalkyl pyridines 53. The 3-haloalkyl pyridine antiinflammatory agents 55 are prepared in a two step procedure from the carbonitriles 51. In step one, the carbonitriles 51 are reduced using agents, such as diisobutyl aluminum hydride (DIBAL) in a solvent such as toluene, at room temperature to form the aldehydes 54. The 3-hydroxyalkyl pyridines 56 also can be isolated from this reaction. In step two, a halogenating agent, such as diethylamino sulfur trifluoride (DAST) is added to the aldehyde 54 to form the haloalkyl pyridines 55. Reduction of aldehydes 54 with agents such as diisobutyl aluminum hydride (DIBAL) followed by methanol and water in methanol to yield the 3-hydroxyalkyl pyridines 56. Compound 56 is convertible to alkoxyalkyl and aralkoxyalkyl compounds 59 by sequential treatment first with a base and then with an alkyl or aralkyl halide. An example of a suitable base is sodium hydride. Examples of alkyl and aralkyl halides are methyl iodide and benzyl chloride. Alternatively, compound 56 may be converted to the haloalkyl compound 57 using a suitable halogenating agent, such as thionyl chloride. Under such circumstances, the hydrochloride salt may be isolated. This in turn may be converted to compounds 58 by reaction with the appropriate alcohol, thiol, or amine. It may be advantageous to carry out this reaction in the presence of a base. Examples of suitable alcohols are methanol, ethanol, benzyl alcohol and phenol. Examples of suitable thiols are n-butyl mercaptan, benzylthiol and thiophenol. Examples of suitable amines are dimethylamine, benzylamine, N-methylbenzylamine, aniline, N-methylaniline and diphenylamine. Examples of suitable bases are sodium hydride and potassium carbonate. Alternatively, amines are accessible by reaction of aldehyde 54 with a primary or secondary amine in the presence of a reducing agent. Examples of suitable primary amines are methyl amine and ethylamine. An example of a suitable secondary amine is dimethylamine. Suitable reducing agents include sodium cyanoborohydride and sodium borohydride.

Scheme XIII

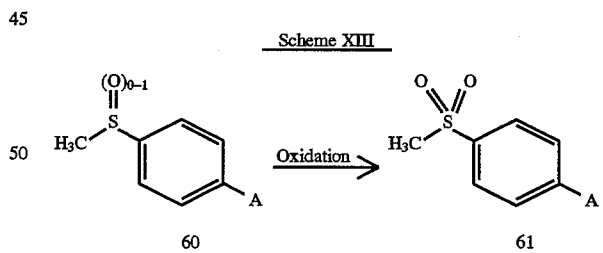

Scheme XIII shows a method to form the alkylsulfonylphenyl substituted heterocycles 61 of the current invention by oxidation of alkylthio or alkylsulfinyl derivatives 60. Aqueous hydrogen peroxide (30%) is added to a suspension of a (methylthio)phenyl substituted heterocycle 60 in acetic acid. The mixture is stirred while heating to about 100° C. for about 2 hours. Alternatively, m-chloroperoxybenzoic acid (MCPBA), and other oxidizing agents [potassium peroxymonosulfate (OXONE®)] can be used to form the sulfonyl radicals Scheme XIII

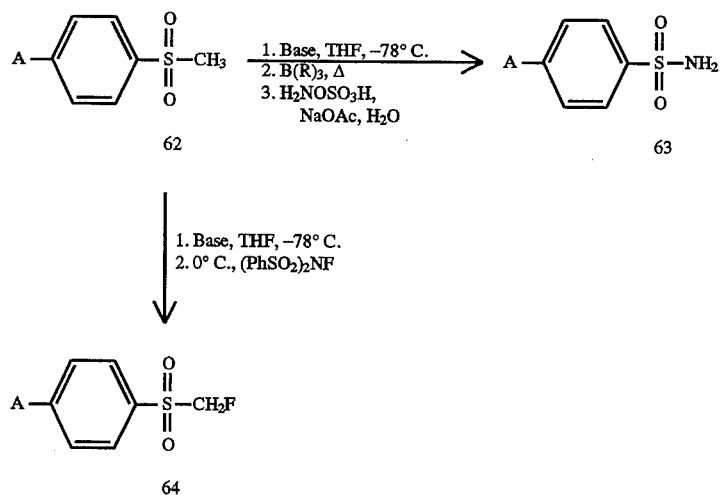

Synthetic Scheme XIV shows the three step procedure used to prepare sulfonamide antiinflammatory agents 63 and the two step procedure used to prepare fluoromethyl sulfone antiinflammatory agents 64 from their corresponding methyl sulfones 62. In step one, THF solutions of the methyl sulfones 62 at −78° C. are treated with an alkyllithium reagent, e.g., methyllithium, n-butyllithium, etc. In step two, the anions generated in step one are treated with an organoborane, e.g., triethylborane, tributylborane, etc., at −78° C. then allowed to warm to ambient temperature prior to stirring at reflux. In step three, an aqueous solution of sodium acetate and hydroxylamine-O-sulfonic acid is added to provide the corresponding sulfonamide antiinflammatory agents 63 of this invention. As an alternative to the borane chemistry found in step two above, the base treated sulfone is reacted with an alkylsilane, such as (iodomethyl) trimethylsilane or (chloromethyl)trimethylsilane, at room temperature to give a silylalkylsulfone. The silylalkylsulfone is converted to a sulfinic acid salt by heating to about 90° C. with tetrabutylammoniumfluoride. Treatment proceeds as in step three above to produce the sulfonamide.

Alternatively, the anion solutions generated in step one may be warmed to 0° C. and treated with N-fluorodibenzenesulfonamide to provide the corresponding fluoromethyl sulfone antiinflammatory agents 64 of this invention.

Scheme XV

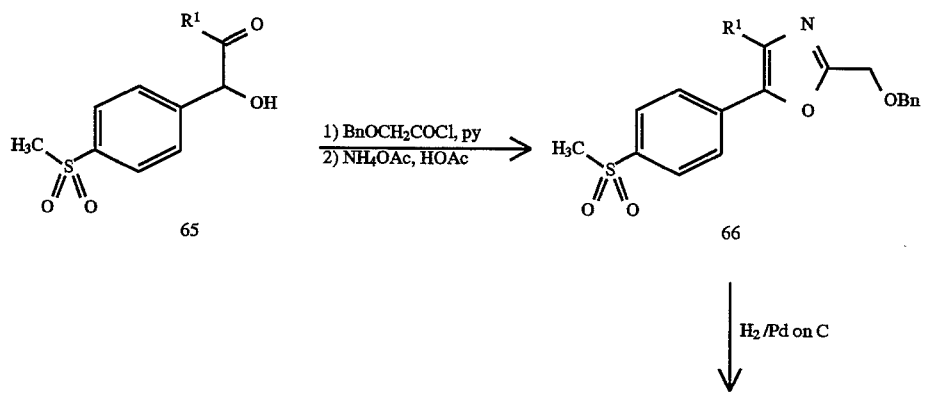

-continued
Scheme XV

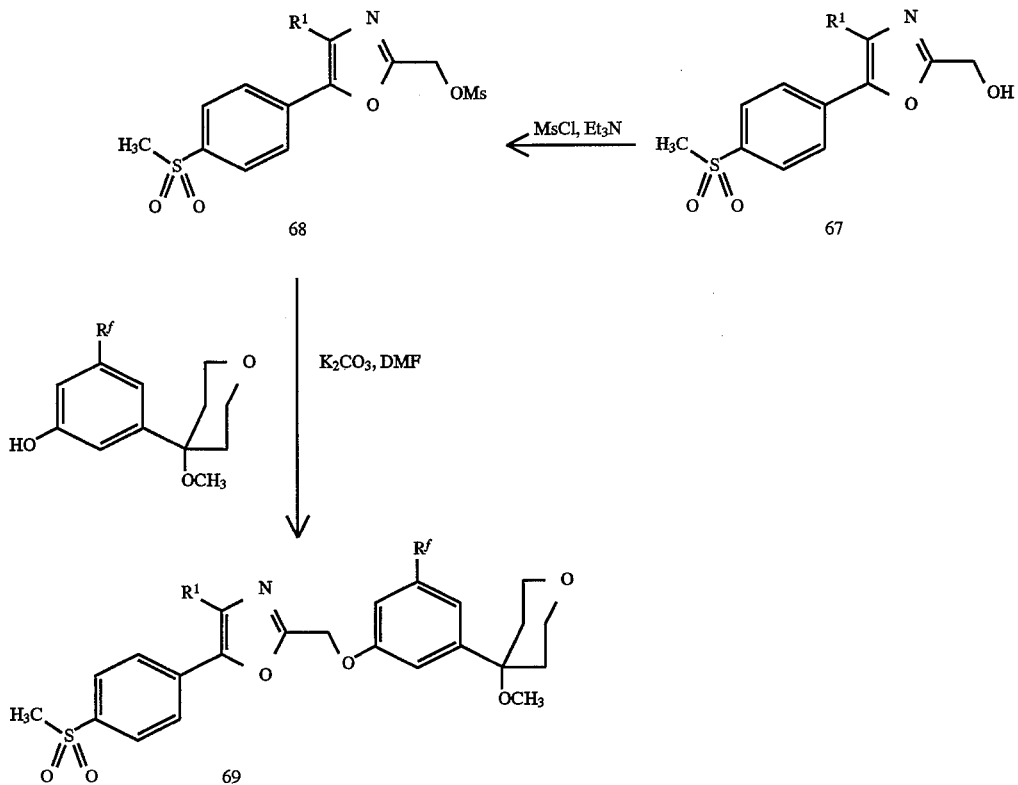

Synthetic Scheme XV shows the four step procedure used to prepare anti-inflammatory compound of Formula II. In step one, a dichloromethane solution of 1-(substitutedphenyl)-2-hydroxy-2-[4-(methylsulfonyl) phenyl]ethanone 65 (described in U.S. Pat. No. 5,380,738) is treated with benzyloxyacetyl chloride in the presence of pyridine base to provide 2-benxyloxymethyl-4-(substitutedphenyl)-5-[4-(methylsulfonyl)phenyl]oxazole 66 in good yield. In step two, the benzyloxy group is removed by hydrogenolysis in the presence of a catalytic amount of 10% palladium on charcoal to provide the hydroxymethyl compound 67. In step three, the hydroxymethyl compound 67 is treated with a solution of methanesulfonyl chloride in the presence of triethylamine base to produce the unstable mesylate 68 that is used directly in the next step. In step four, a mixture of the mesylate and a 3,4,5,6-tetrahydro-2H pyran in dimethylformamide (DMF) is treated with potassium carbonate to effect ether formation and provide the anti-inflammatory agents 69 (where $R^f$ is halo, alkoxy, or alkyl) of the present invention.

Scheme XVI

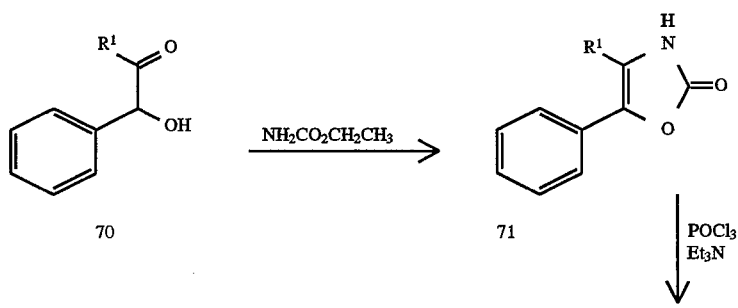

-continued
Scheme XVI

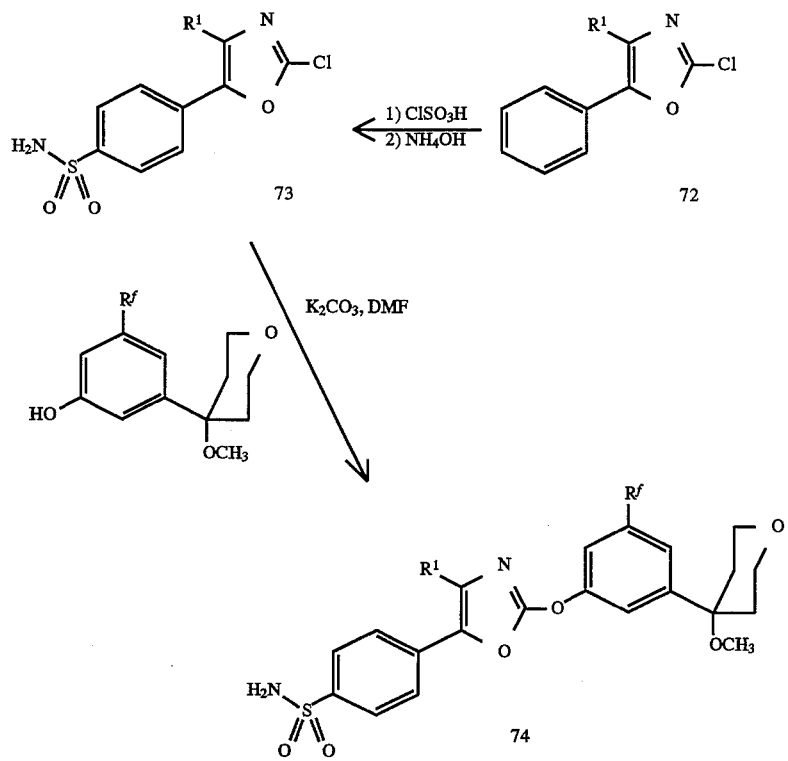

Synthetic Scheme XVI shows the four step procedure that is used to prepare anti-inflammatory compound of Formula II. In step one, benzoin 70 is mixed with ethyl carbamate (urethane) and heated to reflux to provide oxazolone 71 in high yield. In step two, oxazolone 71 is treated with a mixture of phosphorus oxychloride and triethylamine base to produce 2-chloro-5-phenyloxazole 72. In step three, 2-chloro-5-phenyloxazole 72 is treated first with chlorosulfonic acid to effect regioselective chlorosulfonation, followed by treatment with aqueous ammonia provides 2-chloro-5-(4-sulfonamido)phenyloxazole 73 in high yield. In step four, 2-chloro-5-(4-sulfonamido)phenyloxazole 73 and a tetrahydro-2H-pyran is treated with potassium carbonate to effect ether formation and provide the anti-inflammatory agents of the present invention 74.

Scheme XVII

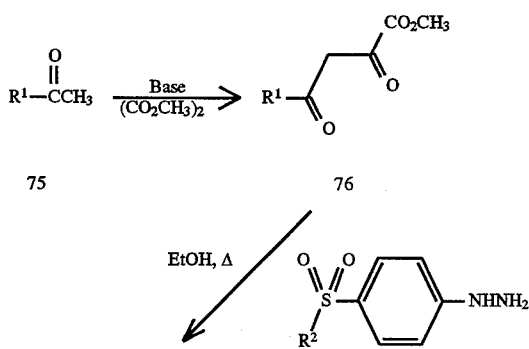

Scheme XVII
-continued

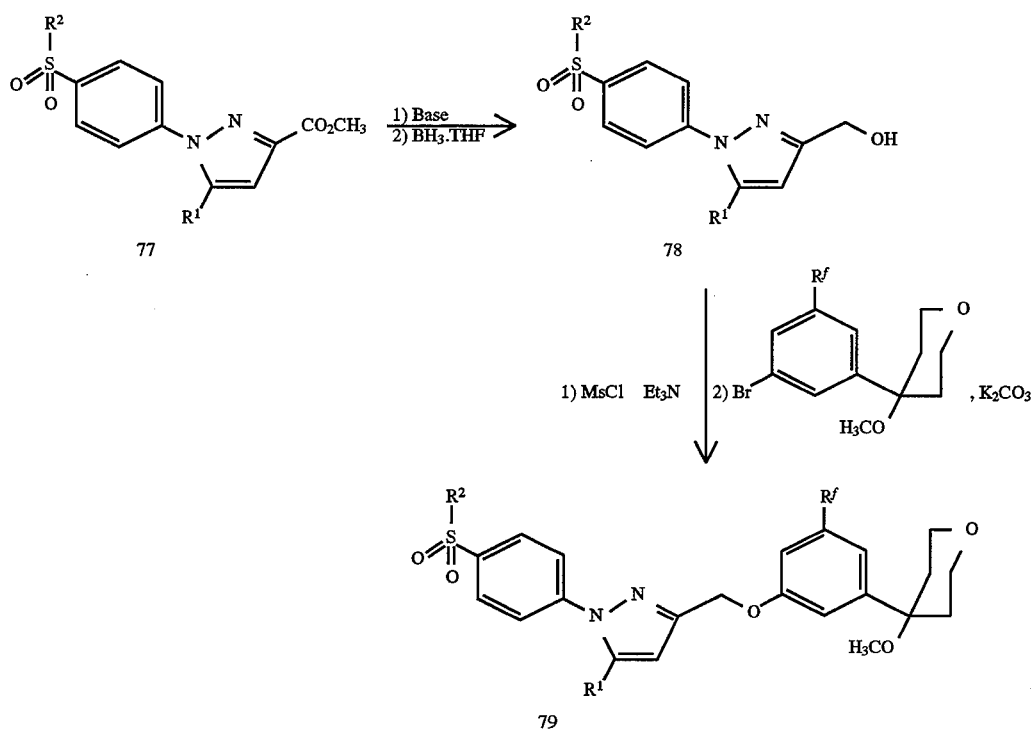

Synthetic Scheme XVII shows a four step method of making the pyrazole phenylethers 79 of the present invention. In step 1, the dione 76 is formed from ketone 75 through the addition of a base, such as lithium bis(trimethylsilyl)amide or lithium diisopropylamide (LDA), followed by reacting with an appropriate acetylating reagent, such as $(CO_2CH_3)_2$. Treatment of the dione 76 with a phenylhydrazine yields the pyrazole ester 77. The pyrazole ester 77 is first treated with base to hydrolyze the ester and is then reduced to the alcohol 78 by treatment with borane in THF. In step four, the alcohol 78 is treated with methanesulfonyl chloride in the presence of triethylamine base to produce the unstable mesylate that is directly reacted with a 3,4,5,6-tetrahydro-2H pyran in dimethylformamide and $K_2CO_3$ to effect ether formation and provide the anti-inflammatory agents 79 of the present invention.

Scheme XVIII

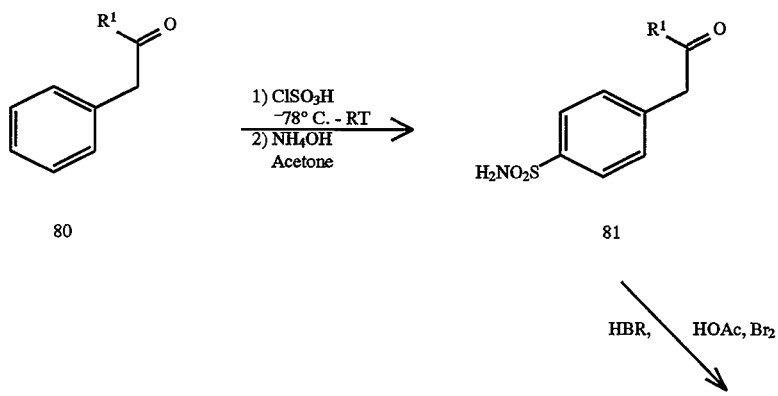

Scheme XVIII

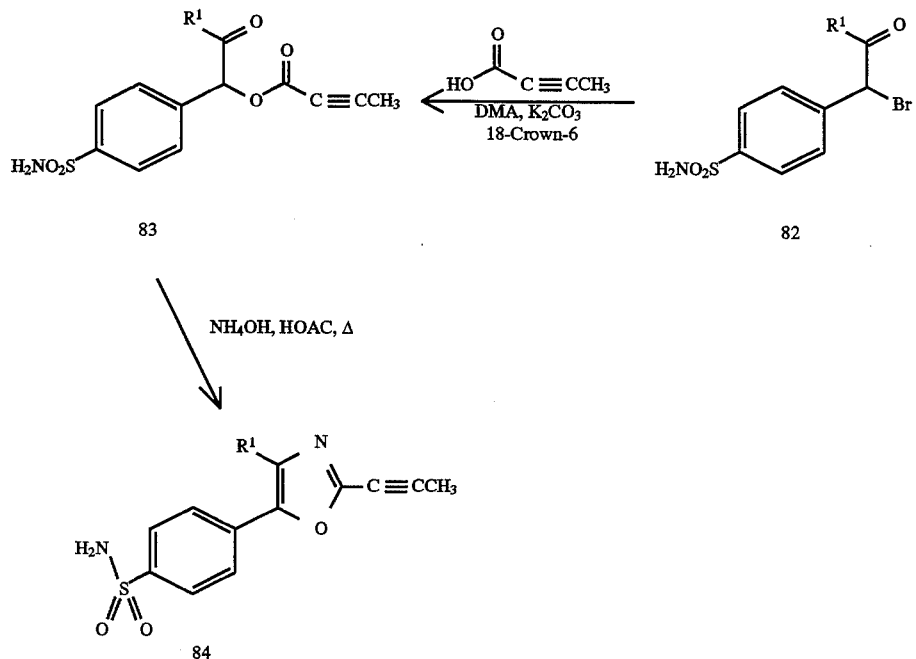

Scheme XVIII shows a procedure for forming an alkynyl oxazole 84 (where $R^2$ is amino), similar to that shown in Scheme V above. The ketone sulfonamide 81 is formed from ketone 80 through chlorosulfonation and ammonolysis with ammonium hydroxide in a solvent such as acetone. The ketone sulfonamide 81 is halogenated, such as with HBr in acetic acid and bromine, to form the haloketone sulfonamide 82. Substitution with butynoic acid in the presence of $K_2CO_3$, a crown ether, such as 18-crown-6, and dimethylacetamide (DMA) yields the alkynyl ketoester 83. Conversion of the alkynyl ester 83 to the alkynyl oxazole 84 proceeds as previously described in Scheme V.

Scheme XIX

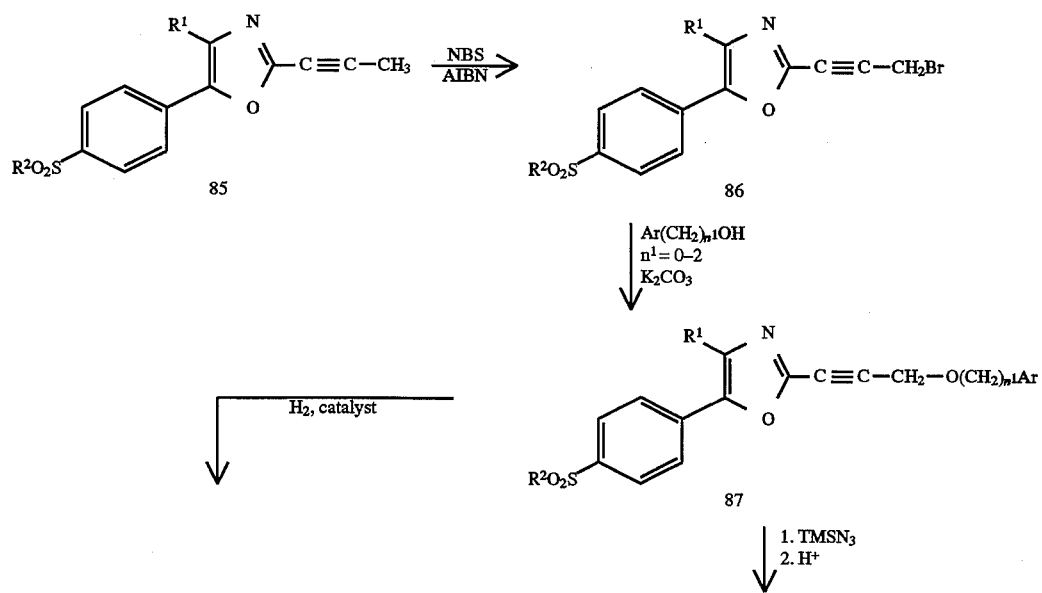

Scheme XIX

-continued

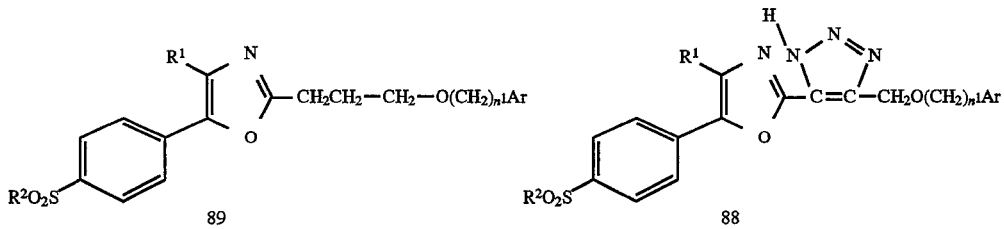

Synthetic Scheme XIX shows the procedures for forming heterocycloalkynylethers 87, heterocyclotriazole ethers 88 and heterocycloalkylethers 89, from the corresponding alkynes 85. The alkynes 85 are halogenated such as with N-bromosuccinimide (NBS) and 2,2'-azobis(2-methylpropionitrile) (AIBN) to form the haloalkynes 86. Substitution with the appropriate aryl or aralkyl alcohols in the presence of potassium carbonate yields the alkynyl ethers 87 of the present invention. The alkynylethers 87 can be converted to heterocyclo-containing spacers 88 by treatment with azidotrimethylsilane, followed by acid. Alternatively, the alkynylethers 87 can be reduced, such as with hydrogen in the presence of catalyst, such as palladium, to yield the heterocycloalkylethers 89.

Scheme XX

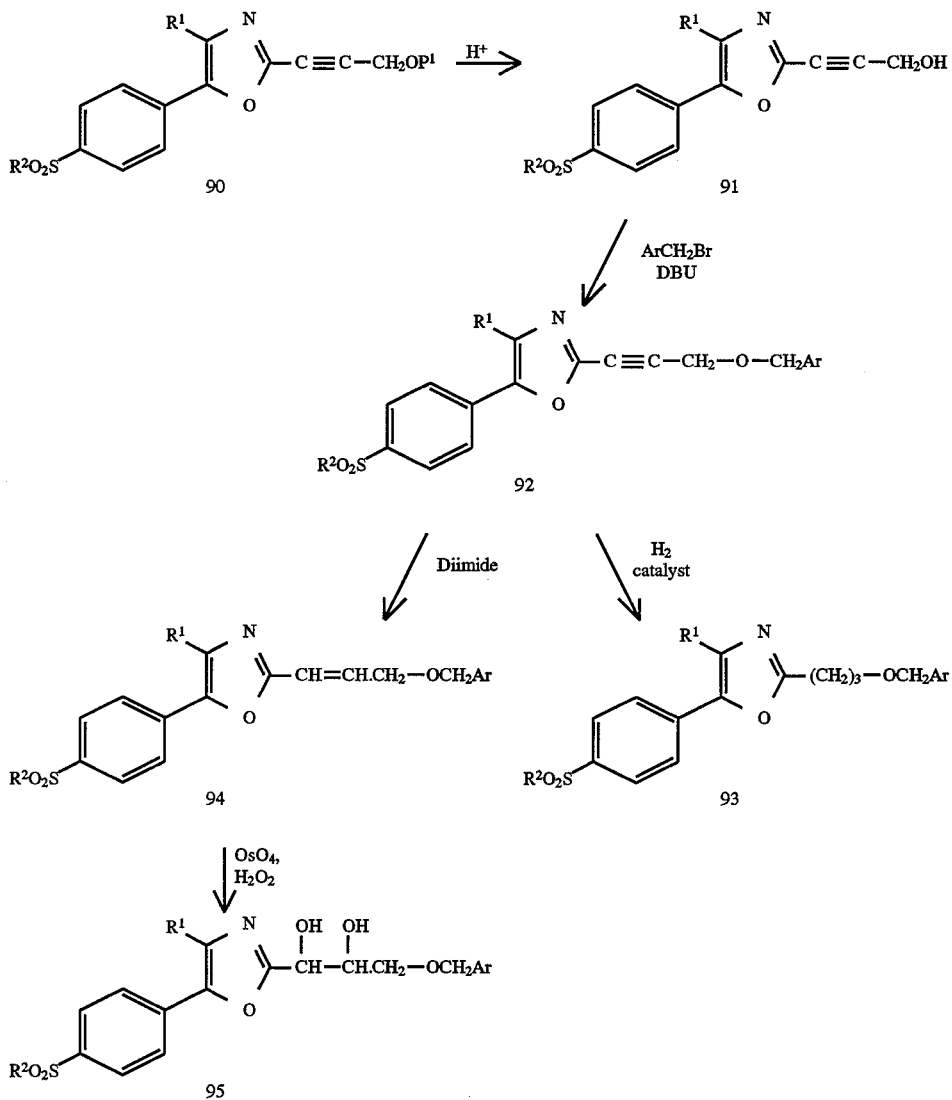

Scheme XX shows another method of forming the alkynylethers 92, alkylethers 93, alkenylethers 94 and the diols 95 of the present invention from the appropriate alkynes 90. In Step one, the alkynes 90 (where P is a protecting group such as tetrahydropyranyl, trialkylsilyl, tert-butyldimethylsilyl or diphenylalkylsilyl) are acid treated to form the alkynyl alcohols 91. Substitution of the alcohol 91 with aralkyl halides or heteroaryl halides in the presence of 1,8-diazabicyclo[5.4.0]undecane (DBU) yields the propynylethers 92 of the present invention. Reduction of the alkynylethers 92 with hydrogen in the presence of metal catalyst yields the alkylethers 93. Alternatively, treatment with diimide reduces the alkynylethers 92 to the alkenylethers 94. Oxidation of the alkenylether 94, such as with osmium tetraoxide and hydrogen peroxide, yields the diols 95 of the present invention.

Additional antiinflammatory agents containing various substituted alkylether spacer radicals including carbonylalkylethers 98, aminoalkylethers 100, hydroxyalkylethers 101, oxyiminoalkylethers 99, and amidoalkylethers 102, can be prepared from ketones 96, by the procedures shown in Scheme XXI. The ketones 96 are halogenated to form halomethylketone 97 such as by treatment with NBS in the presence of AIBN. Substitution of appropriate alcohols with the halides 97 in the presence of base, such as potassium carbonate, generates the ketoalkylethers 98. The ketoalkylethers 98 can be converted to the oxyimino-containing spacers 99 (where $R^g$ is alkyl) by treatment with substituted oxyamines, such as hydroxylamine. Hydroxyalkyl spacers 101 can be prepared by reducing the carbonyl in the ketoalkylethers 99 such as with sodium borohydride. Amination of the ketoalkylethers 99 by reaction with ammonium acetate and sodium cyanoborohydride in the presence of acetic acid generates the aminoalkylethers 100. Acetylation of the aminoethers 100 by acid chlorides or anhydrides in the presence of base, such as trialkylamines, produces the amidoalkylethers 102.

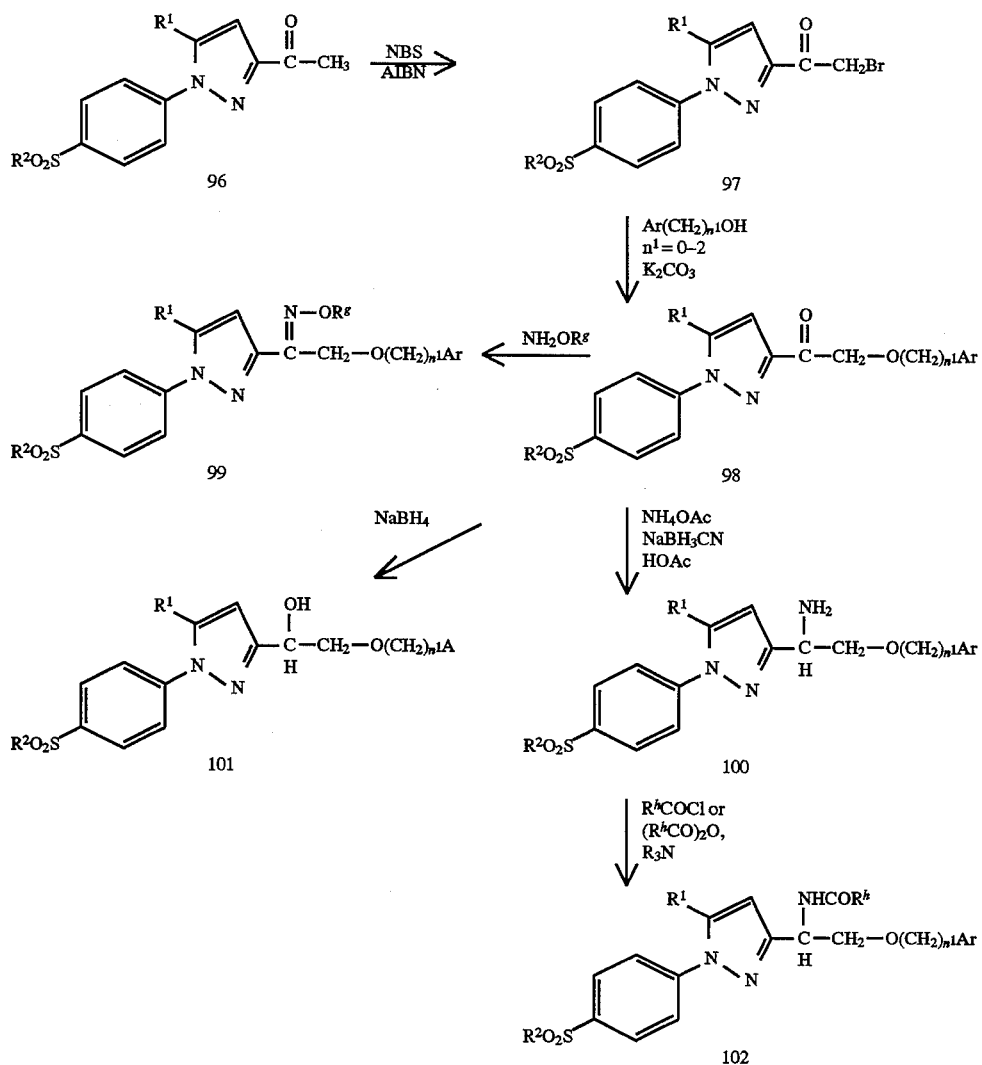

Scheme XXII

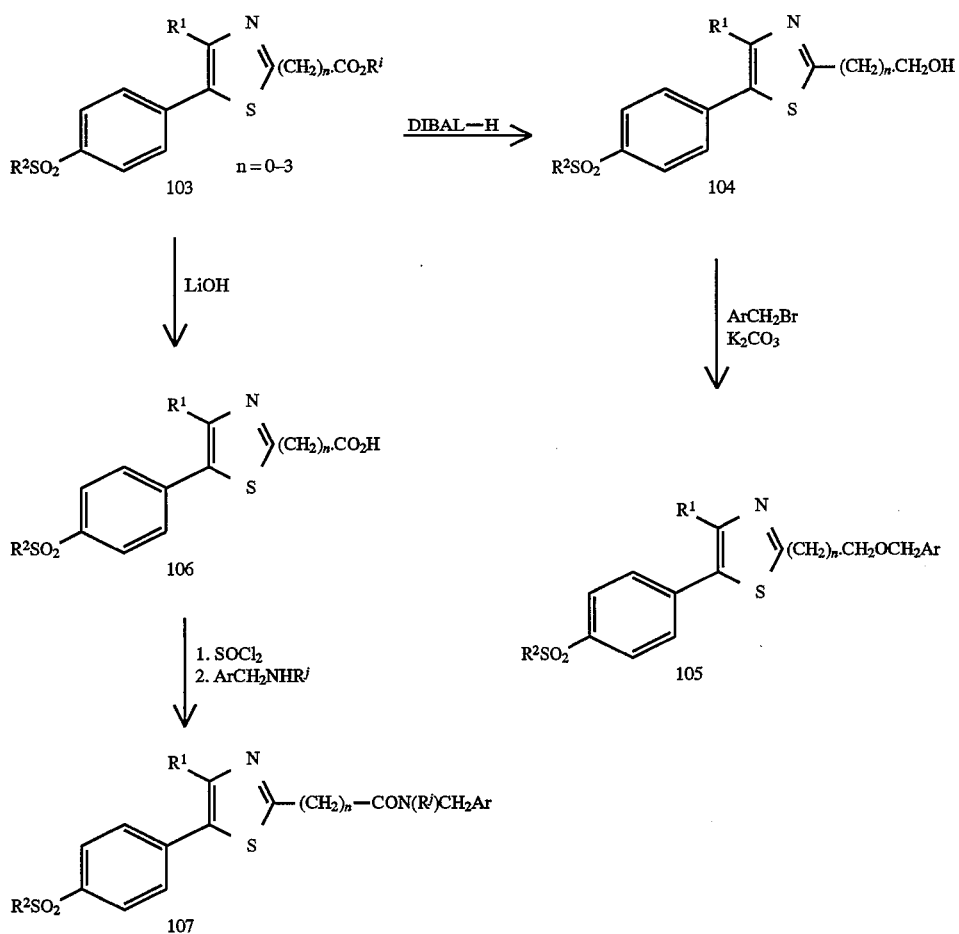

Scheme XXII shows the preparation of ethers 105 and amides 107 antiinflammatory agents of the present invention. Esters 103 where $R^i$ is alkyl, can be converted to the alcohols 104 by treatment with a reducing agent, such as DIBAL-H. The ethers 105 are formed by reacting with an aralkyl halide in the presence of base. Alternatively, the esters 103 can be hydrolyzed to the acids 106 with base such as LiOH. Amides 107 are formed from the acid 106 by treatment with thionyl chloride to form the acid chlorides, followed by substitution with aralkylamines.

Scheme XXIII

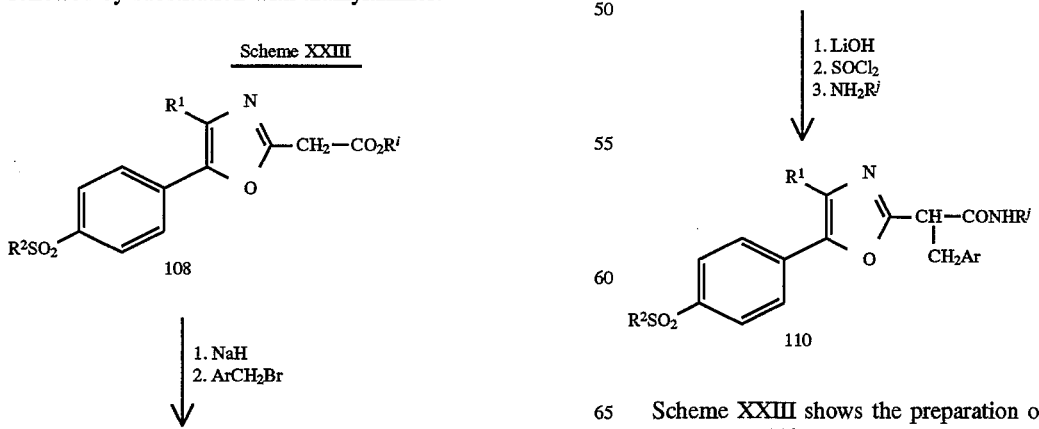

Scheme XXIII shows the preparation of the antiinflammatory esters 109 and amides 110 of the present invention. Base treatment of ester 108, such as with sodium hydride, followed by addition of an aralkyl halide or heteroaralkyl halide forms the ester 109. Formation of the amide 110 from the esters 109 occurs in a three step procedure. Treatment with base, such as lithium hydroxide, and thionyl chloride yields the acid chloride. Addition of an amine yields the amide 110.

The following examples contain detailed descriptions of the methods of preparation of compounds of Formulas I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

EXAMPLE 1

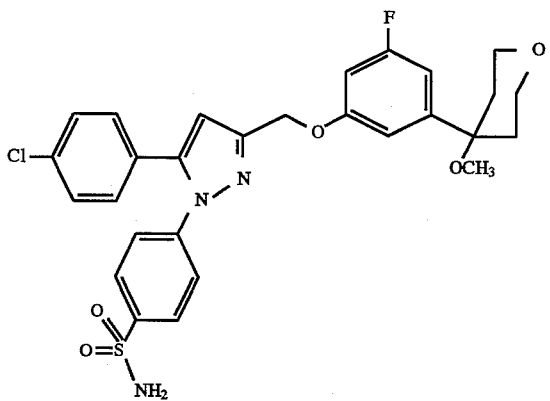

4-[5-(4-Chlorophenyl)-3-[[3-fluoro-5-(3,4,5,6-tetrahydro-4-methoxy-2H-pyran-4-yl)phenoxy]methyl]-1H-pyrazol-1-yl]benzenesulfonamide Step 1. Preparation of methyl -4-(4-chlorophenyl)-2,4-dioxobutanoate.

Dimethyl oxalate (15.27 g, 0.129 mol) and 4'-chloroacetophenone (20.0 g, 0.129 mol) were diluted with methanol (300 mL) and sodium methoxide (25 wt. % in methanol, 70 mL) was added in one portion. The reaction was stirred at room temperature for 16 hours (the reaction became an insoluble mass during this time). The solid was mechanically broken up, hydrochloric acid (conc. 70 mL) was added, and the white suspension was stirred vigorously at room temperature for 1 hour. The suspension was cooled to 0 ° C. and held for 0.5 hour. The solid was filtered, and the filter cake was washed with cold water (100 mL). Upon drying, methyl-4-[4-(chloro)phenyl]-2,4-dioxobutanoate was obtained (16.94 g, 54.4%) as the enol: mp 108.5°–110.5 ° C. $^1$H NMR (CDCl$_3$/300 MHz) δ 7.94 (d, J=8.66 Hz, 2H), 7.48 (d, J=8.66 Hz, 2H), 7.04 (s, 1H), 3.95 (s, 3H), 3.48 (s, 1H).

Step 2. Preparation of methyl 1-4-aminosulfonylphenyl)-5-(4-chlorophenyl)-1H-pyrazole-3-carboxylate Methyl-4-[4-(chloro)phenyl]-2,4-dioxobutanoate(5.0 g, 20.78 mmol) was added to 4-sulfonamidylphenyl hydrazine hydrochloride (5.11 g, 22.86 mmol) and methanol (50 mL). The reaction vessel was heated to reflux and held for 16 hours. A precipitate formed overnight. The suspension was cooled to 0° C., held for 0.5 hour, filtered and washed with cold water to provide, after air drying, 7.91 g, 91% of crude pyrazole. Recrystallized 3.50 g from boiling ethanol to yield 3.14 g (90%) of pure methyl 1-(4-aminosulfonylphenyl)-5-(4-chlorophenyl)-1H-pyrazole-3-carboxylate: mp 227° C.; $^1$H NMR (CDCl$_3$/300 MHz) δ 7.91 (d, J=8.86 Hz, 2H), 7.44 (d, J=8.86 Hz, 2H), 7.33 (d, J=8.66 Hz, 2H), 7.14 (d, J=8.66 Hz, 2H), 7.03 (s, 1H), 3.96 (s, 3H). Mass Spectrum, MH+= 392. Anal. Calc'd for C$_{17}$H$_{14}$N$_3$O$_4$ClS: C, 52.11; H, 3.60; N, 10.72; Cl, 9.05; S, 8.18. Found: C, 52.07; H, 3.57; N, 10.76; Cl, 9.11; S, 8.27.

Step 3. Preparation of 1-(4-aminosulfonylphenyl)-5-(4-chlorophenyl)-1H-pyrazole-3-carboxylic acid Methyl 1-(4-aminosulfonylphenyl)-5-(4-chlorophenyl)-1H-pyrazole-3-carboxylate (1.0 g, 2.66 mmol) was added to tetrahydrofuran (20 mL). Aqueous sodium hydroxide (2.5 N, 2.7 mL) and water (2.5 mL) were added, and the suspension was heated to reflux and held for 16 hours. The solids all dissolved during this time. The reaction was cooled to room temperature, and hydrochloric acid solution (1 N, 11 mL) was added. The aqueous suspension was extracted with methylene chloride (2×20 mL). The combined organic solution was dried over anhydrous magnesium sulfate, filtered, and concentrated in vacuo to an oil. Trituration with 30 mL of dichloromethane yielded, upon filtration and drying, 0.90 g (94%) of 1-(4-aminosulfonylphenyl)-5-(4-chlorophenyl)-1H-pyrazole-3-carboxylic acid as a white solid: mp 126°–128° C.

Step 4. Preparation of 4-[5-(4-chlorophenyl)-3-hydroxymethyl-1H-pyrazol-1-yl]benzenesulfonamide.

4-[4-(Aminosulfonyl)phenyl-5-(4-chlorophenyl)-1H-pyrazole-3-carboxylic acid (3.8 g, 10 mmol) and tetrahydrofuran (100 mL) was stirred at room temperature during the dropwise addition of 1.0M borane-tetrahydrofuran complex (30 mL, 30 mmol). The mixture was allowed to reflux for 16 hours. The solution was cooled and methanol was added dropwise until gas evolution ceased. Ethyl acetate (100 mL) was added and the solution washed with 1N hydrochloric acid, brine, sat. aq. sodium bicarbonate solution, dried over magnesium sulfate, filtered and concentrated. The resultant material was recrystallized from ethanol:water to yield 4-[5-(4-chlorophenyl)-3-hydroxymethyl-1H-pyrazol-1-yl]benzenesulfonamide (2.6 g, 71%) as a white solid: mp 192°–194° C.; $^1$H NMR (DMSO-d$_6$/300 MHz) δ (d, J=8.7 Hz, 2H), 7.46 (d, J=8.4 Hz, 2H), 7.42 (brs, 2H), 7.40 (d, J=8.7 Hz, 2H), 7.26 (d, J=8.4 Hz, 2H), 6.63 (s, 1H), 5.35 (t, J=8.0 Hz, 1H), 4.50 (d, J=8.0 Hz, 2H) . Anal. Calc'd for C$_{16}$H$_{14}$N$_3$SO$_2$Cl: C, 52.82; H, 3.88; N, 11.55. Found: C, 52.91; H, 3.88; N, 11.50.

Step 5. Preparation of 4-[5-(4-chlorophenyl)-3-[[3-fluoro-5-(3,4,5,6-tetrahydro-4-methoxy-2H-pyran-4-yl)phenoxy]methyl]-1H-pyrazol-1-yl]benzenesulfonamide.

A solution of (569 mg, 1.56 mmol) of 4-[5-(4-chlorophenyl)-3-hydroxymethyl-1H-pyrazol-1-yl]benzenesulfonamide in 50 mL of dichloromethane was stirred at 25° C. as triethylamine (315 mg, 3.12 mmol) was added dropwise, followed by the addition of methanesulfonyl chloride (215 mg, 1.88 mmol). The reaction was stirred for 5 minutes, after which the organic solution was washed with 1N HCl, dried over sodium sulfate and concentrated in vacuo to give a yellow oil (500 mg), which was characterized as the expected mesylate by its NMR spectrum. This material was used without further purification. 4-(5-Fluoro-3-hydroxyphenyl)-4-methoxytetrahydropyran (373 mg, 1.649 mmol) and anhydrous potassium carbonate (228 mg, 1,649 mmol) were dissolved in 25 mL of anhydrous DMF. The solution was stirred at room temperature under a blanket of dry nitrogen for 20 minutes, then a solution of mesylate (500 mg, 1.374 mmol) in anhydrous DMF (15 mL) was added in one portion. The resulting solution was stirred at room temperature for 72 hours, then 1N HCl (30 mL) was added. After stirring an additional 0.5 hour, the system was extracted with ethyl acetate (2×40 mL). The combined organic solution was sequentially washed with 1N HCl (40 mL), saturated aqueous NaHCO$_3$ (2×40 mL), 50% saturated NaCl (2×40 mL), and brine (40 mL), dried over MgSO$_4$ and filtered. The solvents were evaporated under reduced pressure to yield an oil. The oil was purified by flash chromatography on silica gel eluting with 40% ethyl acetate in hexane to yield, upon concentration of the appropriate fractions (200 mg, 25%) of 4-[5-( 4-chlorophenyl)-3-[[3-fluoro-5-(3,4,5,6-tetrahydro-4-methoxy-2H-pyran-4-yl) phenoxy]methyl]-1H-pyrazol-1-yl]benzenesulfonamide as a foam: Mass Spectrum: 572 (M+). High resolution mass spectrum Calc'd for C$_{28}$H$_{27}$N$_3$O$_4$ClFS: 572.1422. Found: 572.1361. Anal. Calc'd. for C$_{28}$H$_{27}$N$_3$O$_4$ClFS.1.4 H$_2$O: C, 57.86; H, 5.17; N, 7.23; Cl, 6.10; S, 5.52. Found: C, 57.87; H, 4.92; N, 6.97; Cl, 6.10; S, 5.71.

EXAMPLE 2

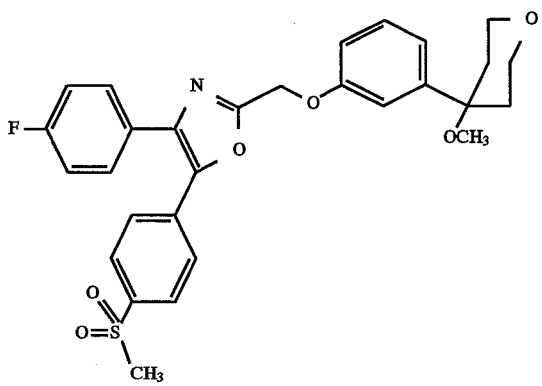

4-(4-Fluorophenyl)-5-(4-(methylsulfonyl)phenyl)-2-[ [3-(3,4,5,6-tetrahydro-4-methoxy-2H-pyran-4-yl) phenoxy)methyl]oxazole Step 1. Esterification of 1-(4-fluorophenyl)-2, hydroxy-2-[4-(methylsulfonylphenyl)ethanone A solution containing (2.07 g, 6.71 mmol) of 1-(4-fluorophenyl)-2-hydroxy-2-[4-(methylsulfonylphenyl) ethanone (U.S. Pat. No. 5,380,738, Jan. 10, 1995) in 100 mL of dichloromethane was stirred at 25 ° C. as (2.71 mL, 33.55 mmol) of pyridine was added, followed by the addition of (1.27 mL, 8.05 mmol) of benzyloxyacetyl chloride. The reaction was stirred at 25° C. for 48 hours, after which the resulting yellow solution was washed with 1N HCl, dried over Na$_2$SO$_4$ and concentrated in vacuo. The oily yellow solid was purified via flash chromatography on a silica gel column using 20% ethyl acetate/hexane as the eluent. This provided 2.22 g (73%) of a white foam, which was characterized as the benzoin ester on the basis of its NMR spectra: $^1$H-NMR (CDCl$_3$, 300 MHz) δ 3.03 (s, 3H), 4.23 (d, 1H, J=17.0 Hz), 4.33 (d, 1H, J=17.0 Hz), 4.67 (s, 2H), 6.95 (s, 1H), 7.13 (t, 2H, J=8.5 Hz), 7.35 (m, 5H), 7.66 (d, 2H, J=8.1 Hz) and 7.98 (m, 4H). $^{19}$F-NMR (CDCl$_2$, 280 MHz ) δ −102.5.

Step 2. Preparation of 2-benzyloxymethyl-4-(4-fluorophenyl)-5-[4-(methylsulfonyl)phenyl]oxazole.

A solution containing (2.22 g, 4.86 mmol) of the benzoin ester from Step 1 and (3.74 g, 48.6 mmol) of ammonium acetate in 100 mL of acetic acid was heated to 80° C. for 2 hours. The reaction was cooled to 25° C. and poured into water. The product was extracted into ethyl acetate and the combined organic extracts were washed with an aqueous solution of sodium bicarbonate. The solution was dried over sodium sulfate and concentrated in vacuo to give a yellow oil. This crude material was purified by flash chromatography on a silica gel column using 25% ethyl acetate/hexane as the eluent to give 2-benxyloxymethyl-4-(4-fluorophenyl) -5-[4-(methylsulfonyl)phenyl]oxazole (1.92 g, 90%) as a clear oil: $^1$H-NMR (CDCl$_3$, 300 MHz) δ 3.07 (s, 3H), 4.70 (s, 2H), 4.72 (s, 2H), 7.11 (t, 2H, J=8.8 Hz), 7.22–7.40 (m, 5H), 7.58 (m, 2H), 7.76 (d, 2H, J=8.8 Hz) and 7.91 (d, 2H, J=8.8 Hz). $^{19}$F-NMR (CDCl$_3$, 280 MHz) δ −111.88.

Step 3. Preparation of 4-(4-fluorophenyl)-2-hydroxymethyl-5-[4-(methylsulfonyl)phenyl]oxazole.

To a solution containing 2-benxyloxymethyl-4-(4-fluorophenyl)-5-[4-(methylsulfonyl)phenyl]oxazole from Step 2 (5.0 g, 11.4 mmol) in 20 mL of 50% THF/methanol was added 100 mg of 10% Pd on charcoal in a Fisher-Porter bottle. The reaction vessel was evacuated and charged with hydrogen at 50 psi for 24 hours. The Pd on carbon was removed by filtration through diatomaceous earth and the filtrate was concentrated in vacuo to give 4-(4-fluorophenyl) -2-hydroxymethyl-5-[4-(methylsulfonyl)phenyl]oxazole (3.8 g, 97%) as a white crystalline solid (recrystallized from 50% ethyl acetate-isooctane): mp 156°–157° C.; $^1$H-NMR (CDCl$_3$, 300 MHz) δ 3.07 (s, 3H), 3.21 (bs, 1H), 4.81 (s, 2H), 7.10 (t, 2H, J=8.5 Hz), 7.56 (m, 2H), 7.72 (d, 2H, J=8.8 Hz) and 7.90 (d, 2H, J=8.8 Hz); $^{19}$F-NMR (CDCl$_3$, 280 MHz) δ −111.5. LRMS m/z 348 (M+H)+. HRMS Calc'd. for C$_{17}$H$_{14}$NO$_4$FS: 348.0706. Found: 348.0681. Anal. Calc'd. for C$_{17}$H$_{14}$NO$_4$FS: C, 58.78; H, 4.06; N, 4.03. Found: C, 58.67; H, 4.02; N, 4.01.

Step 4. Preparation of 4-(4-fluorophenyl)-5-(4-(methylsulfonyl)phenyl)-2-[[3-(3,4,5,6-tetrahydro-4-methoxy-2H-pyran-4-yl)phenoxy)methyl]oxazole.

A solution containing 4-(4-fluorophenyl)-2-hydroxymethyl-5-[4-(methylsulfonyl)phenyl]oxazole from Step 3 (169 mg, 0.487 mmol) in 20 mL of dichloromethane was stirred at 25° C. as triethylamine (136 µL, 0.974 mmol) was added dropwise, followed by the addition of methanesulfonyl chloride (56 µL, 0.730 mmol). The reaction was stirred for 5 minutes, after which the organic solution was washed with 1N HCl, dried over sodium sulfate and concentrated in vacuo to give a yellow oil which was characterized as the expected mesylate by its NMR spectrum: $^1$H-NMR (CDCl$_3$, 400 MHz) δ 3.08 (s, 3H), 3.17 (s, 3H), 5.37 (s, 2H), 7.12 (t, 2H, J=8.8 Hz), 7.58 (m, 2H), 7.78 (d, 2H, J=8.8 Hz) and 7.94 (d, 2H, J=8.8 Hz). This material was used without further purification. The mesylate was dissolved in 20 mL of DMF and potassium carbonate (81 mg, 0.584 mmol) was added, followed by the addition of 4-(3-hydroxyphenyl)-4-methoxy-3,4,5,6-tetrahydro-2H-pyran (122 mg, 0.584 mmol). The reaction was stirred at 25 ° C. for 3 days and poured into 100 mL of water. The aqueous solution was extracted with ethyl acetate and the combined extracts were dried over sodium sulfate and concentrated in vacuo to give a beige solid. This material was purified by flash chromatography on a silica gel column using 50% ethyl acetate/hexane as the eluent to give 4-(4-fluorophenyl) -5-(4-(methylsulfonyl)phenyl)-2-[[3-(3,4,5,6-tetrahydro-4-methoxy-2H-pyran-4-yl)phenoxy)methyl]oxazole (185 mg, 71%) as a white crystalline solid: $^1$H-NMR (CDCl$_3$, 300 MHz) δ 1.90–2.05 (m, 4H), 2.97 (s, 3H), 3.08 (s, 3H), 3.81 (m, 4H), 5.25 (s, 2H), 6.98–7.17 (m, 5H), 7.33 (t, 1H, J=7.7 Hz), 7.60 (m, 2H), 7.78 (d, 2H, J=8.5 Hz) and 7.93 (d, 2H, J=8.5 Hz). $^{19}$F-NMR (CDCl$_3$, 280 MHz) δ −111.6. LRMS m/z 544 (M+Li)+. HRMS Calc'd. for C$_{29}$H$_{28}$NO$_6$FS: 544. 1781 (M+Li)+. Found: 544. 1831 (M+Li)+.

EXAMPLE 3

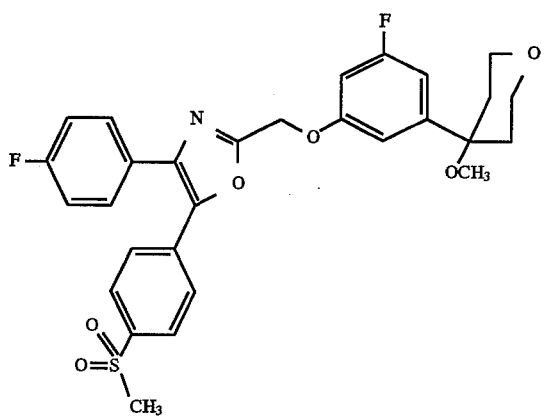

4-(4-Fluorophenyl)-2-[[3-fluoro-5-(3,4,5,6-tetrahydro-4-methoxy-2H-pyran-4-yl)phenoxy) methyl]-5-(4-(methylsulfonyl)phenyl)oxazole 4-(4-Fluorophenyl)-2-[[3-fluoro-5-(3,4,5,6-tetrahydro-4-methoxy-2H-pyran-4-yl)phenoxy)methyl]-5-(4-(methylsulfonyl)phenyl)oxazole was prepared in a similar fashion from the reaction of the mesylate (Example 2, Step 4) and 4-(3-fluoro-5-hydroxyphenyl)-4-methoxy-3,4,5,6-tetrahydro-2H-pyran: $^1$H-NMR (CDCl$_3$, 300 MHz) δ 1.84–2.02 (m, 4H), 2.98 (s, 3H), 3.08 (s, 3H), 3.81 (m, 4H), 5.23 (s, 2H), 6.76 (m, 2H), 6.92 (s, 1H), 7.13 (m, 2H), 7.60 (m, 2H), 7.79 (d, 2H, J=8.5 Hz) and 7.93 (d, 2H, J=8.5 Hz). $^{19}$F-NMR (CDCl$_3$, 280 MHz) δ −110.8 and −111.7. Anal. Calc'd. for C$_{29}$H$_{27}$NO$_6$F$_2$: C, 62.69; H, 4.90; N, 2.52. Found: C, 62.53; H, 4.96; N, 2.51.

EXAMPLE 4

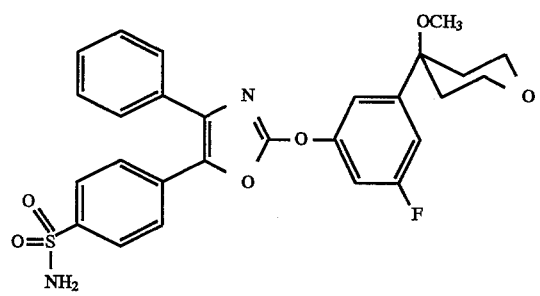

4-[2-[3-Fluoro-5-(4-methoxy-3,4,5,6-tetrahydro-2H-pyran-4-yl)phenoxy]-4-phenyl-5-oxazolyl] benzenesulfonamide Step 1. Preparation of 4,5-diphenyloxazolone.

Benzoin (31.8 g, 0.15 mol) and urethane (42.79 g, 0.45 mol) were heated to reflux for 3.0 hours. The hot mixture was poured into water (150 mL). Acetone (150 mL) was added and heat was applied until the mixture dissolved. The solution was cooled and filtered, producing a white solid which was used in the next step without further purification.
Step 2. Preparation of 2-chloro-4,5-diphenyloxazole.

4,5-Diphenyloxazolone from Step 1 (30 g, 0.126 mol), triethylamine (12.8 g, 0.126 mol), and phosphorous oxychloride (96.6 g, 0.63 mol) were stirred at reflux for 4.0 hours. The mixture was concentrated in vacuo, dissolved in ether (250 mL), washed with 1N HCl, brine, and water, dried over MgSO$_4$ and concentrated to a light yellow oil which was used in the next step without further purification or characterization.

Step 3. Preparation of 4-[2-chloro-4-phenyl-5-oxazolyl] benzenesulfonamide

Chlorosulfonic acid (20 mL) was cooled to 0° C. with stirring. 2-Chloro-4,5-diphenyloxazole from Step 2 (1.53 g, 6 mmol) was added, and the stirred solution was warmed to room temperature over 1.0 hour. The mixture was added dropwise to ice and dichloromethane (50 mL) with stirring. The resultant organic layer was washed once with water and added to a 0° C. stirred solution of ammonium hydroxide (10 mL). The mixture was stirred for 1.0 hour and extracted with dichloromethane (3×50 mL). The combined organic layers were washed with 1N HCl followed by brine and water, dried over MgSO$_4$ and concentrated. Recrystallization from ethyl acetate/hexanes gave a white solid (1.5 g, 75%): mp 158°–159° C. Anal. Calc'd. for C$_{15}$H$_{11}$N$_2$O$_3$SCl: C, 53.82; H, 3.31; N, 8.37. Found: C, 53.92; H, 3.32; N, 8.33.

Step 4. Preparation of 4-[2-[3-fluoro-5-(4-methoxy-3,4,5,6-tetrahydro-2H-pyran-4-yl)phenoxy]-4-phenyl-5-oxazolyl] benzenesulfonamide 4-[2-Chloro-4-phenyl-5-oxazolyl]benzenesulfonamide from Step 3 (0.74 g, 2.2 mmol), N,N'-dimethylformamide (DMF) (20 mL), potassium carbonate (0.61 g, 4.4 mmol), and 4-(3-fluoro-5-hydroxyphenyl)-4-methoxy-3,4,5,6-tetrahydro-2H-pyran [prepared as described by G. C. Crawley, et al, J. Med. Chem., 35, 2600–2609 (1992)] (0.75 g, 7.5 mmol) were stirred at room temperature for 16.0 hours. The solution was diluted with ethyl acetate (100 mL), washed with 1N HCl, brine and water, dried over MgSO$_4$ and concentrated. The residue was dissolved in ethyl acetate/hexanes (1:1) and filtered through silica. The eluant was concentrated and the residue was recrystallized from ethyl acetate/hexanes to afford 4-[2-[3-fluoro-5-(4-methoxy-3,4,5,6-tetrahydro-2H - pyran-4-yl)phenoxy]-4 -phenyl-5-oxazolyl]benzenesulfonamide as a white solid (0.4 g, 35%): mp 159°–161° C. $^1$H NMR (CDCl$_3$) 300 MHz δ 7.9 (d, J=8.7 Hz, 2H) 7.72 (d, J=8.7 Hz, 2H) 7.6 (m, 2H) 7.4 (m, 3H) 7.24–7.30 (m, 2H) 7.0–7.1 (dt, J=9.5 Hz and J=1.8 Hz, 1H) 4.85 (bs, 2H) 3.85 (dd, J=9.9 Hz and J=1.8 Hz, 4H) 3.05 (s, 3H) 2.0 (m, 4H). Anal. Calc'd. for C$_{27}$H$_{25}$N$_2$O$_6$SF: C, 61.82; H, 4.80; N, 5.34. Found: C, 61.77; H, 4.82; N, 4.31.

EXAMPLE 5

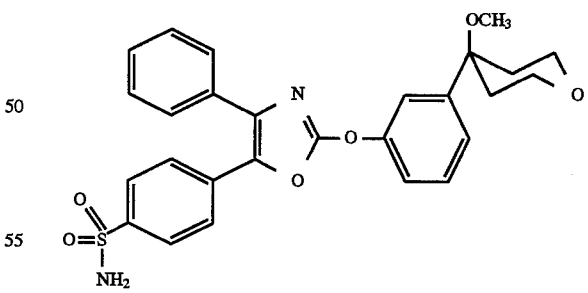

4-[2-[3-(4-Methoxy-3,4,5,6-tetrahydro-2H-pyran-4-yl)phenoxy]-4-phenyl-5-oxazolyl] benzenesulfonamide 4-[2-Chloro-4-phenyl-5-oxazolyl]benzenesulfonamide from Example 4, Step 3, (0.6 g, 1.8 mmol), DMF (20 mL), potassium carbonate (0.5 g, 3.6 mmol), and 4 (3-hydroxyphenyl)-4-methoxy-3,4,5,6-tetrahydro-2H-pyran (0.37 g, 1.8 mmol) [prepared as described by G. C. Crawley, et al, *J. Med. Chem.*, 35, 2600–2609 (1992)]were stirred at room temperature for 16.0 hours. The solution was diluted with ethyl acetate (100 mL), washed with 1N HCl, brine and water, dried over MgSO$_4$ and concentrated. The residue was dissolved in ethyl acetate/hexanes (1:1) and filtered through silica. The eluant was concentrated and the residue recrystallized from ethyl acetate/hexanes to give 4-[2-[3-(4-methoxy-3,4,5,6-tetrahydro-2H-pyran-4-yl)phenoxy]-4-phenyl-5-oxazolyl]benzenesulfonamide as a white solid (0.4 g, 44%): mp 145°–147° C. $^1$H NMR (CDCl$_3$) 300 MHz δ 7.88 (d, J=8.9 Hz, 2H) 7.70 (d, J=8.9 Hz, 2H) 7.6 (m, 2H) 7.36–7.5 (m, 6H) 7.0–7.1 (dt, J=6.4 Hz and J=2.2 Hz, 1H) 4.85 (bs, 2H) 3.7 (m, 4H) 3.05 (s, 3H) 2.0 (m, 4H). Anal. Calc'd. for C$_{27}$H$_{26}$N$_2$O$_6$S: C, 64.02; H, 5.17; N, 5.53. Found: C, 63.94; H, 5.17; N, 5.55.

EXAMPLE 6

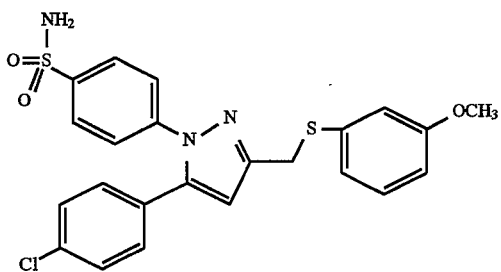

4-[5-(4-Chlorophenyl)-3-(3-methoxyphenyl)thiomethyl-1H pyrazol-1-yl]benzenesulfonamide Step 1. Preparation of methyl 4-(4-chlorophenyl)-2,4-dioxobutanoate.

Dimethyl oxalate (15.27 g, 0,129 mol), and 4'-chloroacetophenone (20.0 g, 0.129 mol) were added to methanol (300 mL). Sodium methoxide (25 wt. % in methanol, 70 mL) was added dropwise over about 0.5 hour. The reaction was stirred at room temperature for 16 hours, whereupon the sodium salt of the butanoate precipitated from solution. The mixture was treated with 70 mL of conc. HCl and the white suspension was stirred vigorously at room temperature for 1 hour. The suspension was cooled to 0° C. and held for 0.5 hour. The solid was filtered, and the filter cake was washed with cold water (100 mL). After drying in vacuo, methyl 4-[4-(chloro)phenyl]-3-ketobutyrate was obtained (16.94 g, 54.4%) as the enol: $^1$H NMR (CDCl$_3$/300 MHz) δ 7.94 (d, J=8.66 Hz, 2H), 7.48 (d, J=8.66 Hz, 2H), 7.04 (s, 1H), 3.95 (s, 3H), 3.48 (s, 1H).

Step 2. Preparation of 4-[4-(aminosulfonyl)phenyl-5-(4 chlorophenyl)-1H-pyrazole-3-carboxylic acid.

4-Sulfonamidophenylhydrazine hydrochloride (1.45 g, 6.5 mmol) and methyl-4-(4-chlorophenyl)-2,4-dioxobutanoate from Step 1 (1.2 g, 5.0 mmol) were dissolved in 50 mL of methanol and heated to reflux for 20 hours. After cooling to room temperature, the reaction mixture was concentrated in vacuo and the residue dissolved in ethyl acetate, washed with water and brine, dried over anhydrous MgSO$_4$, filtered and re-concentrated to give a light brown solid. The crude solid was crystallized from methanol and water to provide 1.6 g, 85% of pure compound. This material was dissolved in 150 mL of methanol and treated with 75 mL of 3N NaOH. The solution was heated to reflux for 3 hours, and concentrated in vacuo. The residue was acidified with conc. HCl and was extracted into ethyl acetate. After removal of the ethyl acetate, the acid was isolated and dried to afford 1.4 g, (75%, mp 135° C.) that was used directly in the next step.

Step 3. Preparation of 4-[5-(4-chlorophenyl)-3-hydroxymethyl-1H pyrazol-1-yl]benzenesulfonamide.

4-[4-(Aminosulfonyl)phenyl-5-(4 chlorophenyl)-1H-pyrazole-3-carboxylic acid from Step 2 (3.8 g, 10 mmol) and tetrahydrofuran (100 mL) were stirred at room temperature during dropwise addition of 1.0M borane-tetrahydrofuran complex (30 mL, 30 mmol). The mixture was held at reflux for 16 hours. The mixture was cooled and methanol was added dropwise until gas evolution ceased. Ethyl acetate (100 mL) was added and the mixture was washed with 1N hydrochloric acid, brine, sat. aq. sodium bicarbonate solution, and water, dried over magnesium sulfate, filtered and concentrated. The resultant alcohol was recrystallized from ethanol:water to yield a white solid (2.6 g, 71%): mp 192°–194° C. $^1$H NMR (DMSO-d$_6$/300 MHz) δ 7.81 (d, J=8, 7 Hz, 2H), 7.46 (d, J=8.4 Hz, 2H), 7.42 (brs, 2H), 7.40 (d, J=8.7 Hz, 2H), 7.26 (d, J=8.4 Hz, 2H), 6.63 (s, 1H), 5.35 (t, J=8.0 Hz, 1H), 4.50 (d, J=8.0 Hz, 2H). Anal. Calc'd for C$_{16}$H$_{14}$N$_3$SO$_2$Cl: C, 52.82; C, 52.91; H, 3.88; H, 3.88; N, 11.55; N, 11.50.

Step 4. Preparation of 4-[5-14-chlorophenyl)-3-(3-methoxyphenyl)thiomethyl-1H-pyrazol-1-yl]benzenesulfonamide.

4-[5-(4-Chlorophenyl)-3-hydroxymethyl-1H-pyrazol-1-yl]benzenesulfonamide from Step 3 (500 mg, 1.374 mmol) was dissolved in anhydrous THF (30 mL). Triethylamine (0.385 mL, 2.749 mmol) and methanesulfonyl chloride (0.16 mL, 2.062 mmol) were added sequentially, and the cloudy suspension was stirred at room temperature for 0.5 hour. The reaction was diluted with ethyl acetate (35 mL) and washed with aqueous HCl (1N, 50 mL). The organic solution was dried over anhydrous MgSO$_4$ and filtered, then the solvent was evaporated under reduced pressure to yield a crude oil. The oil was dissolved in anhydrous THF (10 mL). 3-Methoxythiophenol (0.205 mL, 1.649 mmol) was dissolved in anhydrous THF. Sodium hydride (95%, 42 mg, 1.649 mmol) was added, and the resulting frothy suspension was stirred at room temperature for 20 minutes, forming a clear, colorless solution. The solution of the mesylate prepared above was added, then the reaction was warmed to 40° C. and held for 16 hours. The reaction was cooled to room temperature then 1N HCl (30 mL) was added. After stirring an additional 0.5 hour, the system was extracted with ethyl acetate (2×40 mL). The combined organic solution was sequentially washed with 1N HCl (40 mL), saturated aqueous NaHCO$_3$ (2×40 mL), 50% saturated NaCl (2×40 mL), and brine (40 mL), then dried over anhydrous MgSO$_4$ and filtered. The solvents were evaporated under reduced pressure to yield an oil. The oil was purified by flash chromatography over silica gel eluting with 40% ethyl acetate in hexane to yield 4-[5-(4-chlorophenyl)-3-(3-methoxyphenyl)thiomethyl-1H-pyrazol-1-yl]benzenesulfonamide (273 mg, 41%) as a foam: Mass Spectrum: 486 (MH+). High resolution mass spectrum Calc'd. for C$_{23}$H$_{20}$N$_3$O$_3$ClS$_2$: 486.0713. Found: 486.0757. Anal. Calc'd. for C$_{23}$H$_{20}$N$_3$O$_3$ClS$_2$: C, 56.84; H, 4.15; N, 8.65; Cl, 7.29; S, 13.19. Found: C, 56.56; H, 4.22; N, 8.61; Cl, 7.41; S, 13.00.

EXAMPLE 7

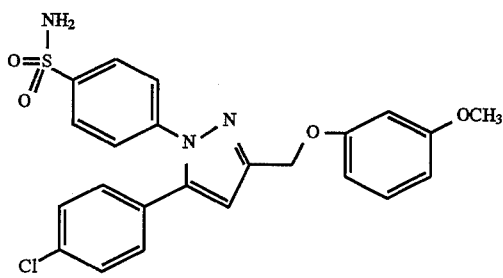

4-[5-(4-Chlorophenyl)-3-(3-methoxyphenyl)oxymethyl-1H-pyrazol-1-yl]benzenesulfonamide 4-[5-(4-Chlorophenyl)-3-(3-methoxyphenyl)oxymethyl-1H-pyrazol-1-yl]benzenesulfonamide was prepared from 4-[5-(4-chlorophenyl)-3-hydroxymethyl-1H-pyrazol-1-yl]benzenesulfonamide (prepared in Example 6, step 3) in 39% yield by the method outlined in Example 1, Step 4: Mass Spectrum: 470 (MH+). High resolution mass spectrum Calc'd. for $C_{23}H_{20}N_3O_4ClS$: 470.0979. Found: 470.0983. Anal. Calc'd. for $C_{23}H_{20}N_3O_4ClS$: C, 58.78; H, 4.29; N, 8.94; Cl, 7.54; S, 6.82. Found: 58.85; H, 4.29; N, 8.90; Cl, 7.63; S, 6.93.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterhess and Bliven, *Laboratory Models for Testing NSAIDs, in Non-steroidal Anti-Inflammatory Drugs*, (J. Lombardino, ed. 1985)). The % inhibition shows the % decrease from control paw volume determined in this procedure and the data for selected compounds in this invention are summarized in Table I.

TABLE I

RAT PAW EDEMA

| | % Inhibition @ 10 mg/kg body weight |
|---|---|
| Example 3 | 15 |

Evaluation of COX-1 and COX-2 activity in vitro

The compounds of this invention exhibited inhibition in vitro of COX-2. The COX-2 inhibition activity of the compounds of this invention illustrated in the Examples was determined by the following methods.

a. Preparation of recombinant COX beculoviruses

Recombinant COX-1 and COX-2 were prepared as described by Gierse et al, [*J. Biochem.*, 305, 479–84 (1995)]. A 2.0 kb fragment containing the coding region of either human or murine COX-1 or human or murine COX-2 was cloned into a BamH1 site of the baculovirus transfer vector pVL1393 (Invitrogen) to generate the baculovirus transfer vectors for COX-1 and COX-2 in a manner similar to the method of D. R. O'Reilly et al (*Baculovirus Expression Vectors: A Laboratory Manual* (1992)). Recombinant baculoviruses were isolated by transfecting 4 μg of baculovirus transfer vector DNA into SF9 insect cells ($2 \times 10^8$) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer ($10^7$–$10^8$ pfu/ml) stocks of virus were prepared. For large scale production, SF9 insect cells were infected in 10 liter fermentors ($0.5 \times 10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000 xG for 30 minutes, and the resultant supernatant was stored at –80° C. before being assayed for COX activity.

b. Assay for COX-1 ond COx-2 activity

COX activity was assayed as $PGE_2$ formed/μg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 μM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 μl of reaction mix into 160 μl ELISA buffer and 25 μM indomethacin. The $PGE_2$ formed was measured by standard ELISA technology (Cayman Chemical). Results are shown in Table II.

Assay for 5-Lipoxygenase activity

The 5-lipoxygenase (5-LO) activity of the compounds were determined by the calcium ionophore-induced Leukotriene B4 (LTB4) production in human whole blood. Venous blood was collected from healthy human donors using heparin as an anti-coagulant. Human blood samples (0.2 ml of a 1:4 dilution in RPMI 1640 medium) were incubated in 96-well culture plates for 15 minutes at 37° C. with test compounds dissolved in ethanol (EtOH; final concentration <1%), or vehicle. Typically 7 concentrations of test compounds were examined in duplicate. A-23187 [Sigma] was added to the blood to a final concentration of 20 μg/ml, and the mixtures were incubated for 10 minutes at 37° C. The reaction was stopped by placing the samples on ice. The samples were then centrifuged at 800×g at 4° C. for 10 minutes to pellet the cells, and the supernatants were recovered for quantitation of LTB4 by ELISA (Cayman Chemical Co.; sensitivity 3 pg/ml). $IC_{50}$'s were estimated from a four parameter logistic model with two parameters fixed, the minimum (0% inhibition) and maximum (100% inhibition). The $IC_{50}$ value is the concentration that produces 50% inhibition between the fixed values of the minimum and maximum. Data is reported as the mean $IC_{50}$ for each compound. Results are shown in Table II.

TABLE II

| Example | COX-2 IC$_{50}$ (µM) | COX-1 IC$_{50}$ (µM) | 5-LO IC$_{50}$ (µM) |
| --- | --- | --- | --- |
| 1 | <0.1 | 38 | 0.15 |
| 2 | 0.2 | <10 | 0.05 |
| 3 | <0.1 | <100 | 0.02 |
| 4 | <0.1 | <0.1 | 14 |
| 5 | <0.1 | <0.1 | 17 |
| 6 | <0.1 | 2.2 | 0.44 |
| 7 | <0.1 | 3.8 | 0.65 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

In the case of psoriasis and other skin conditions, it may be preferable to apply a topical preparation of a compound of this invention to the affected area two to four times a day.

For inflammations of the eye or other external tissues, e.g., mouth and skin, the formulations are preferably applied as a topical ointment or cream containing the active ingredient(s) in a total amount of, for example, 0.075 to 30% w/w, preferably 0.2 to 20% w/w and most preferably 0.4 to 15% w/w. When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. The compounds of this invention can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmirate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The antiinflammatory active ingredients are preferably present in such formulations in a concentration of 0.5 to 20%, advantageously 0.5 to 10% and particularly about 1.5% w/w.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

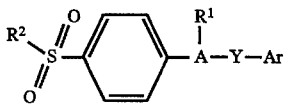

wherein A is oxazolyl or isoxazolyl, wherein A is optionally substituted with a radical selected from acyl, halo, alkyl, haloalkyl, cyano, nitro, carboxyl, alkoxy, oxo, aminocarbonyl, alkoxycarbonyl, carboxyalkyl, cyanoalkyl, and hydroxyalkyl;

wherein Y is a radical selected from oxy, thio, sulfinyl, sulfonyl, alkyl, alkenyl, alkynyl, alkyloxy, alkylthio, alkylcarbonyl, cycloalkyl, aryl, haloalkyl, hydroxyalkyl, hydroxyalkyloxy, hydroxyalkyloxyalkyl, hydroxyalkylthio, hydroxyalkylthioalkyl, oximinoalkoxy, oximinoalkoxyalkyl, (alkyl) oximinoalkoxy, (alkyl) oximinoalkoxyalkyl, oximinoalkylthio, oximinoalkylthioalkyl, (alkyl)oximinoalkylthio, (alkyl)oximinoalkylthioalkyl, carbonylalkyloxy, carbonylalkyloxyalkyl, carbonylalkylthio, carbonylalkylthioalkyl, heterocyclo, cycloalkenyl, aralkyl, heterocycloalkyl, acyl, alkylthioalkyl, alkyloxyalkyl, alkenylthio, alkynylthio, alkenyloxy, alkynyloxy, alkenylthioalkyl, alkynylthioalkyl, alkenyloxyalkyl, alkynyloxyalkyl, arylcarbonyl, aralkylcarbonyl, aralkenyl, haloalkylcarbonyl, alkoxyalkyl, alkylaminocarbonylalkyl, heteroaralkoxyalkyl, heteroaryloxyalkyl, heteroarylthioalkyl, heteroaralkylthioalkyl, heteroaralkoxy, heteroaralkylthio, heteroaryloxy, heteroarylthio, arylthioalkyl, aryloxyaryloxy, haloaryloxyalkyl, aralkylthioalkyl, aralkoxyalkyl, alkoxyaralkoxyalkyl, alkoxycarbonylalkyl, alkoxycarbonylcyanoalkenyl, aminocarbonylalkyl, N-alkylaminocarbonyl, N-arylaminocarbonyl, N, N-dialkylaminocarbonyl, N-alkyl-N-arylaminocarbonyl, cycloalkylaminocarbonyl, heterocycloaminocarbonyl, carboxyalkylaminocarbonyl, alkylcarbonylalkyl, aralkoxycarbonylalkylaminocarbonyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyl-N-aralkylamino, N-alkyl-N-arylamino, aminoalkyl, N-alkylaminoalkyl, N,N-dialkylaminoalkyl, N-arylaminoalkyl, N-aralkylaminoalkyl, N-alkyl-N-aralkylaminoalkyl, N-alkyl-N-arylaminoalkyl, aminoalkoxy, aminoalkoxyalkyl, aminoalkylthio, aminoalkylthioalkyl, cycloalkyloxy, cycloalkylatkyloxy, aryloxy, aralkoxy, arylthio, aralkylthio, alkylsulfinyl, alkylsulfonyl, aminosulfonyl, N-alkylaminosulfonyl, N-arylaminosulfonyl, arylsulfonyl, N, N-dialkylaminosulfonyl, N-alklyl-N-arylaminosulfonyl,

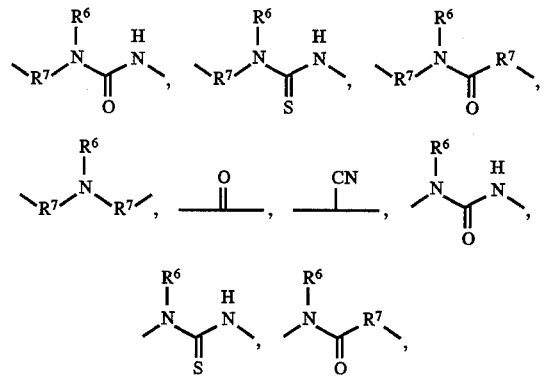

wherein Ar is selected from aryl and heteroaryl, wherein Ar is optionally substituted with one or two substituents selected from halo, hydroxyl, amino, nitro, cyano, carbamoyl, alkyl, alkenyloxlz, alkoxy, alkylthio, alkylsulfinyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, alkoxycarbonylalkoxy and

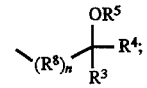

wherein $R^1$ is one or more substituent selected from heterocyclo, cycloalkyl, cycloalkenyl and aryl, wherein $R^1$ is optionally substituted at a substitutable position with one or more radicals selected from alkyl, haloalkyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio;

wherein $R^2$ is selected from alkyl and amino; wherein $R^3$ and $R^4$ together form a group of the formula —B—X—$B^1$ which together with the carbon atom to which B and $B^1$ are attached, defines a ring having 6 ring atoms, wherein B and $B^1$, which may be the same or different, each is alkylene and X is oxy, and which ring may bear one, two or three substituents, which may be the same or different, selected from hydroxyl, alkyl, alkoxy, alkenyloxy and alkynyloxy;

wherein $R^5$ is selected from hydrido, alkyl, alkanoyl, and aroyl, optionally substituted with a substituent selected from halo, alkyl and alkoxy;

wherein $R^6$ is selected from hydrido, alkyl, aryl and aralkyl;

wherein $R^7$ is selected from alkyl, alkenyl and alkynyl;

wherein $R^8$ is oximino optionally substituted with alkyl; and wherein n is 0 or 1;

provided Ar is substituted with

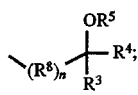

or a pharmaceutically-acceptable salt thereof.

2. Compound of claim 1 wherein A is a radical selected from oxazolyl, and isoxazolyl, wherein A is optionally substituted with a radical selected from acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl) oximinoalkoxyalkl, lower carbonylalkyloxy, lower carbonylalkyloxyalkyl, lower hydroxyalkylthio, lower hydroxyalkylthioalkyl, lower oximinoalkylthio, lower oximinoalkylthioalkyl, lower (alkyl) oximinoalkylthio, lower (alkyl)oximinoalkylthioalkyl, lower carbonylalkylthio, lower carbonylalkylthioalkyl, lower alkylthio, lower alkylcarbonyl, lower cycloatkyl, phenyl, lower haloalkyl, 5- or 6-membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower heteroaralkoxyalkyl, lower heteroaryloxyalkyl, lower heteroarylthioalkyl, lower heteroaralkylthioalkyl, lower heteroaralkoxy, lower heteroaralkylthio, lower heteroaryloxy, lower heteroarylthio, lower arylthioalkyl, lower aryloxyalkyl, lower aralkylthioalkyl, lower aralkoxyalkyl, lower alkoxyaralkoxyalkyl, lower alkoxycarbonylalkyl, lower alkoxycarbonylcyanoalkenyl, lower aminocarbonylalkyl, lower N-alkylaminocarbonyl, N-phenylaminocarbonyl, lower N,N-dialkylaminocarbonyl, lower N-alkyl-N-arylaminocarbonyl, lower cycloalkylaminocarbonyl, lower heterocycloaminocarbonyl, lower carboxyalkylaminocarbonyl, lower alkylcarbonylalkyl, lower aralkoxycarbonylalkylaminocarbonyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-phenylamino, lower N-aralkylamino, lower N-alkyl-N-aralkylamino, lower N-alkyl-N-arylamino, lower aminoalkyl, lower N-alkylaminoalkyl, lower N,N-dialkylaminoalkyl, lower N-arytaminoalkyl, lower N-aralkylaminoalkyl, lower N-alkyl-N-aralkylaminoalkyl, lower N-alkyl-N-arylaminoalkyl, lower aminoalkoxy, lower aminoalkoxyalkyl, lower aminoalkylthio, lower aminoalkylthioalkyl, lower cycloalkyloxy, lower cycloalkylalkyloxy, phenyloxy, lower aralkoxy, phenylthio, lower aralkylthio, lower alkylsulfinyl, lower alkylsulfonyl, aminosulfonyl, lower N-alkylaminosulfonyl, lower N-arylaminosulfonyl, lower arylsulfonyl, lower dialkylaminosulfonyl, lower N-alkyl-N-arylaminosulfonyl,

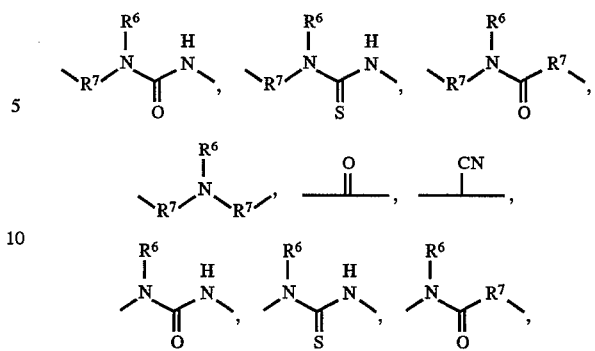

wherein Ar is selected from aryl selected from phenyl, biphenyl and naphthyl, and 5- and 6-membered heteroaryl, wherein Ar is optionally substituted with one or two substituents selected from halo, hydroxyl, amino, nitro, cyano, carbamoyl, lower alkyl, lower alkenyloxy, lower alkoxy, lower alkyithio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower alkoxycarbonylalkoxy and

wherein $R^1$ is at least one substituent selected from 5- and 6-membered heterocyclo, lower cycloalkyl, lower cycloalkenyl and aryl selected from phenyl, biphenyl and naphthyl, where $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; wherein $R^3$ and $R^4$ together form a group of the formula —B—X—$B^1$ which together with the carbon atom to which B and $B^1$ are attached, defines a ring having 6 ring atoms, wherein B and $B^1$, which may be the same or different, each is alkylene and X is oxy, and which ring may bear one, two or three substituents, which may be the same or different, selected from hydroxyl, lower alkyl, lower alkoxy, lower alkenyloxy and lower alkynyloxy; wherein $R^5$ is selected from hydrido, lower alkyl, lower alkenyl, lower alkynyl, lower cyanoalkyl, lower alkanoyl, and benzoyl optionally substituted with a substituent selected from halo, lower alkyl and lower alkoxy; wherein $R^6$ is selected from hydrido, lower alkyl, phenyl and lower aralkyl; wherein $R^7$ is selected from lower alkyl, lower alkenyl and lower alkynyl; wherein $R^8$ is oximino optionally substituted with alkyl; and wherein n is 0 or 1; or a pharmaceutically-acceptable salt thereof.

3. Compound of claim 2 wherein A is a radical selected from oxazolyl, and isoxazolyl, wherein A is optionally substituted with a radical selected from acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxlalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, lower carbonylalkytoxyalkyl, lower hydroxyalkylthio, lower hydroxyalkytthioalkyl, lower oximinoalkalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylthio, lower alkylcarbonyl, lower cycloalkyl, phenyl, lower haloalkyl, 5- or 6-membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkenylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower arylthioalkyl, lower aryloxyalkyl, lower aralkylthioalkyl, lower aralkoxyalkyl, lower alkoxycarbonylalky, lower aminocarbonylalkyl, lower N-alkylaminocarbonyl, N-phenylaminocarbonyl, lower alkylcarbonylalkyl, lower N-alkylamino, N-phenylamino, lower N-aralkylamino, lower aminoalkyl, lower N-alkyaminoalkyl, lower N-arylaminoalkyl, lower N-aralklylaminoalkyl, lower aminoalkoxy, lower aminoalkoxyalkyl, lower aminoalkylthio, lower aminoalkytthioalkyl, lower cycloalkyloxy, lower cycloalkylalkyloxy, phenyloxy, lower aralkoxy, phenylthio, lower aralkylthio, lower alkylsulfinyl, lower alkylsulfonyl, aminosulfonyl, lower N-alkylaminosulfonyl, N-phenylaminosulfonyl, phenylsulfonyl, oximino,

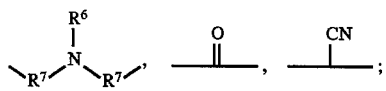

wherein Ar is selected from aryl selected from phenyl, biphenyl, naphthyl, and 5- and 6-membered heteroazyl, wherein Ar is optionally substituted with one or two substituents selected from halo, hydroxyl, amino, nitro, cyano, lower alkyl, lower alkoxy, and

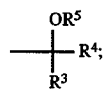

wherein R¹ is at least one substituent selected from 5- and 6-membered heteroaryl, and aryl selected from phenyl, biphenyi and naphthyl, where R¹ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, nitro, lower alkoxyalkl, lower alkylsulfinyl, halo, lower alkoxy and lower alkylthio; wherein R² is selected from lower alkyl and amino; wherein R³ and R⁴ together form a tetrahydropyran ring and which ring may bear one, two or three substituents, which may be the same or different, selected from hydroxyl, lower alkyl, and lower alkoxy; wherein R⁵ is selected from hydrido and lower alkyl; wherein R⁶ is selected from hydrido, lower alkyl, phenyl and lower aralkyl; and wherein R⁷ is selected from lower alkyl, lower alkenyl and lower alkynyl; provided Ar is substituted with

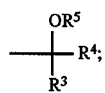

or a pharmaceutically-acceptable salt thereof.

4. Compound of claim 3 wherein A is a radical selected from oxazolyl, and isoxazolyl, wherein A is optionally substituted with a radical selected from acyl, halo, lower alkyl, lower haloalkyl, oxo, cyano, carboxyl, lower alkoxy, arninocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkynyl, lower alkenyl, aryl, lower cycloalkyl, 5- or 6-membered heterocyclo, aralkyl, lower alkyloxy, aryloxy, arylthio, 5- or 6-membered heterocyclooxy, lower aralkylthio, lower aralkyloxy, lower alkythio, lower alktrnyloxy, lower alkynylthio, lower alkynyioxyalky, lower alkenyloxy, lower alkenylthio, lower alkenyloxyalkyl, lower alkyloxyalkyl, lower alkylthioalkyl, lower hydroxyalkyloxy, lower hydroxyaloxyalkyl, lower oximinoalkoxy, lower oximinoalkoxyalkyl, lower (alkyl) oximinoalkoxy, lower (alkyl)oximinoalkoxyalkyl, lower carbonylalkyloxy, and lower carbonylalkyloxyalkyl; wherein Ar is selected from phenyl, thienyl, oxazolyl, furyl, pyrrolyl, thiazolyl, imidazclyl, isothiozolyl, isoxazolyl, pyrazolyl, cyclopentenyl, and pyridyl, wherein Ar is optionally substituted with one or two substituents selected from halo, hydroxyl, lower alkyl, lower alkoxy, and

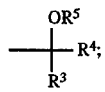

wherein R¹ is at least one substituent selected from thienyl, oxazolyl, furyl, pyrrolyl, thiazolyl, imidazolyl, isothiazolyl, isoxazolyl, pyrazolyl, cyclopentenyl, pyridyl, and phenyl, where R¹ is optionally substituted at a substitutable position with one or more radicals selected from lower alkyl, lower haloalkyl, hydroxyl, lower hydroxyalkyl, lower haloalkoxy, nitro, lower alkoxyalkyl, halo, lower alkoxy and lower alkylthio; wherein R² is selected from lower alkyl and amino; wherein R³ and R⁴ together form a tetrahydropyran ring, and which ring may bear one, two or three substituents, which may be the same or different, selected from hydroxyl, lower alkyl, and lower alkoxy; and wherein R⁵ is selected from hydrido and lower alkyl; or a pharmaceutically-acceptable salt thereof.

5. Compound of claim 4 wherein A is a radical selected from oxazolyl, and isoxazolyl, wherein A is optionally substituted with a radical selected from acyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl; wherein Y is a radical selected from oxy, ethyl, isopropyl, butyl, 1-propynyl, 2-propynyl, methyloxy, ethyloxy, propyloxy, methylthio, (Z)-1-propenyloxy, (E)-2-propenyloxy, (Z)-2-propenyloxy, (E)-1-propenyloxy, Z) -1-propenyloxymethyl, (E)-2-propenyloxymethyl, (Z)-2 -propenyloxymethyl, (E)-1-propenyloxymethyl, 2-propynyloxy, 2-propynyloxy, 1-propynylthio, 2-propynylthio, hydroxymethyloxy, 1-hydroxyethyloxy, 2-hydroxypropyloxy, hydroxymethyloxymethyl, 1-hydroxyethyloxymethyl, 2-hydroxypropyloxymethyl, methyloxymethyl, ethyloxymethyl, propyloxlrmethyl, 1 -propynyloxymethyl, oximinomethyloxy, oximinomethyloxymethyl, (methyl) oximinomethyloxy, (methyl)oximinomethyloxymethyl, triazolylmethyloxy, triazolylmethyloxymethyl, carbonylmethyloxy, carbonylbutyloxy, and carbonylmethyloxymethyl; wherein Ar is selected from phenyl, thienyl, oxazolyl, furyl, pyrrolyl, thiazolyl, irmidazolyl, isothiazolyl, isoxazolyl, pyrazolyl, cyclopentenyl, and pyridyl, wherein Ar is substituted with

wherein $R^1$ is selected from thienyl, oxazolyl, fuzyl, pyrrolyl, thiazolyl, imidazolyl, isothiazolyl, isoxazolyl, pyrazolyl, cyclopentenyl, pyridyl, and phenyl, where $R^1$ is otbionally substituted at a substitutable position with one or more radicals selected from methyl, trifluoromethyl, hydroxyl, hydroxymethyl, trifluoromethoxy, nitro, methoxymethyl, fluoro, chloro, bromo, methoxy and methylthio; wherein $R^2$ is methyl or amino; wherein $R^3$ and $R^4$ together form a tetrahydropyran ring, and which ring may bear one, two or three substituents, which may be the same or different, selected from hydroxyl, methyl, and methoxy; and wherein $R^5$ is selected from hydrido and methyl; or a pharmaceutically-acceptable salt thereof.

6. Compound of claim 5 selected from compounds and their pharmaceutically-acceptable salts, of the group consisting of 4-[3-(phenyl)-5-[[3-(3,4,5,6-tetrahydro-4-methoxy-2H-pyran-4-yl) phenoxy]acetyl]-4-isoxazolyl] benzenesulfonamide;

4-[3-(phenyl)-4-[4-(methylsulfonyl)phenyl]-5-[[3- [3,4,5,6-tetrahydro-4-methoxy-2H-pyran-4-yl)phenoxy]acetyl] isoxazole;

4- [3-(phenyl) -5- [[3-fluoro-5- (3,4,5,6-tetrahydrc-4-methoxy-2H-pyran-4-yl)phenoxy]acetyl]-4-isoxazolyl] benzenesulfonamide;

4-[3-(phenyl)-5-[[3-(3,4,5,6-tetrahydro-4-methoxy-2H-pyran-4-yl)benzyloxy]acetyl ]-4 -isoxazolyl] benzenesulfonamide;

4-[2-[3-(4-methoxy-3,4,5,6-tetrahydro-2H-pyran-4-yl) benzyloxy]acetyl]-4-isoxazolyl]benzenesulfonamide;

4-[2-[3-fluoro-5- (4-methoxy-3,4,5,6-tetrahydro-2H-pyran-4-yl)phenoxy]-4-phenyl - 5-oxazolyl]benzenesulfonamide;

4-(4-fluorophenyl)-2-[[3-fluoro-5-(3,4,5,6-tetrahydro-4-methoxy-2H-pyran-4-yl)phenoxy)methyl]-5-(4-(methylsulfonyl)phenyl)oxazole;

4-(4-fluorophenyl)-5-(4- (methylsulfonyl)phenyl)-2-[[3-(3,4,5,6-tetrahydro-4-methoxy-2H-pyran-4-yl)phenoxy) methyloxazole;

4-[4-(phenyl)-2-[[3-(3,4,5,6-tetrahydro-4-methoky-2H-pyran-4-yl) phenoxy]acetyl]-5-oxazolyl] benzenesulfonamide;

4-[4-(phenyl)-5-[4-(methylsulfonyl)phenyl]-2-[[3-(3,4,5,6-tetrahydro-4-methoxy- 2H-pyran - 4-yl)phenoxy]acetyl] oxazole;

4-[4- (phenyl)-2-[[3-fluoro-5-(3,4,5,6-tetrahydro-4-methoxy-2H-pyran-4-yl)phenoxy]acetyl]-5-oxazolyl] benzenesulfonamide;

4-[4-(phenyl)-[[3-(3,4, 5,6-tetrahydro-4-methoxy-2H-pyran-4-yl)benzyloxy]acetyl]-5 -oxazolyl] benzenesulfonamide;

4-[4-(phenyl)-2-[[3-fluoro-5- (3,4,5,6-tetrahydro-4-methoxy-2H-pyran-4 -yl)-3-pyridinyloxy]acetyl]-5-oxazolyl]denzenesulfonamide;

4-[4-(phenyl)-2-[[3-fluoro-5- (3,4,5,6-tetrahydro-4-methoxy-2H-pyran-4 -yl)-3-pyridylmethoxy]acetyl]-5-oxazolyl]denzenesulfonamide;

4-(phenyl)-2-[[5-(3,4,5,6-tetrahydro-4-methoxy-2H-pyran-4-yl)pyridin-2-ylmethoxy]acetyl]-5-oxazolyl] benzenesulfonamide;

4-(phenyl)-2-[[3-(2,6-dimethyl-3,4,5,6-tetrahydro-4-methoxy-2H-pyran-4-yl)benzyloxy]acetyl]-5-oxazolyl] benzenesulfonamide;

4-(phenyl)-2-[[2-(3,4,5,6-tetrahydro-4-methoxy-2-H-pyran-4-yl)thiazol-4-ylmethoxy]acetyl]-5-oxazolyl] benzenesulfonamide;

4-(phenyl)-2-[[3-fluoro-5-(1S, 5R, 3α-methoxy-6,8-dioxabicyclo[3.2.1]octanyl)phenoxy]acetyl]-5-oxazolyl] benzenesulfonamide;

4-(phenyl)-2-[[3-(3,4,5,6-tetrahydro-4-hydroxy-2H-pyran-4-yl)phenoxy]acetyl]-5-oxazolyl]benzenesulfonamide;

4-[4-(phenyl)-2-[2-[3,4,5,6-tetrahydro-4-methoxy-2H-pyran-4-yl)phenoxy](E-oximinomethyl)ethyl]-5-oxazolyl] benzenesulfonamide;

4-[4-(phenyl)-2-[2-[3,4,5,6-tetrahydro-4-methoxy-2H-pyran-4-yl)phenoxy](Z-oximinomethyl)ethyl]-5-oxazolyl] benzenesulfonamide;

4-[4-(phenyl)-2-[2-[3,4,5,6-tetrahydro-4-methoxy-2H-pyran-4-yl)phenoxy](E-oximino)ethyl]-5-oxazolyl] benzenesulfonamide;

4-[4-(phenyl)-2-[2-[3,4,5,6-tetrahydro-4-methoxy-2H-pyran-4-yl)phenoxy](Z-oximino)ethyl]-5-oxazolyl] benzenesulfonamide;

4-[4-(phenyl)-5-[4-[4-methylsulfonyl)phenyl]-2-[2-[3-(3,4,5,6-tetrahydro-4-methoxy-2H-pyran-4yl)phenoxy](E-oximinomethyl)ethyl]oxazole;

4-[4-(phenyl)-5-[4-[4-methylsulfonyl)phenyl]-2-[2-[3-(3,4,5,6-tetrahydro-4-methoxy-2H-pyran-4yl)phenoxy](Z-oximinometyl)ethyl]oxazole;

4-[4-(phenyl)-2-[2-[3-fluoro-5-(3,4,5,6-tetrahydro-4-methoxy-2H-pyran-4-yl)phenoxy](E-oximino)ethyl]-5-oxazolyl]benzenesulfonamide;

4-[4-(phenyl)-2-[2-[3-fluoro-5-(3,4,5,6-tetrahydro-4-methoxy-2H-pyran-4-yl)phenoxy](Z-oximino)ethyl]-5-oxazolyl]benzenesulfonamide;

4-[4-(phenyl)-2-[2-[3-(3,4,5,6-tetrahydro-4-methoxy-2H-pyran-4-yl)benzyloxy](E-oximino)ethyl]-5-oxazolyl] benzenesulfonamide;

4-[4-(phenyl)-2-[2-[3-(3,4,5,6-tetrahydro-4-methoxy-2H-pyran-4-yl)benzyloxy](Z-oximino)ethyl]-5-oxazolyl] benzenesulfonamide;

4-[4-(phenyl)-2-[2-[3-fluoro-5-(3,4,5,6-tetrahydro-4-methoxy-2H-pyran-4-yl) benzyloxy]( E-oximino ) ethyl]-5-oxazolyl]benzenesulfonamide;

4-[4-(phenyl) -2-[2-[3-fluoro-5-(3,4,5,6-tetrahydro-4-methoxy-2H-pyran-4-yl)benzyloxy](Z-oximino)ethyl]-5-oxazolyl]benzenesulfonamide;

4-[4-(phenyl)-2-[2-[3-(3,4,5,6-tetrahydro-4-methoxy-2H-pyran-4-yl)thienyloxy](E-oximino)ethyl]-5-oxazolyl] benzenesulfonamide;

4- [4-(phenyl)-2-[2-[3-(3,4,5,6-tetrahydro-4-methoxy-2H-pyran-4-yl) thienyloxy](Z-oximino) ethyl]-5-oxazolyl] benzenesulfonamide;

4-[4-(phenyl)-2-[2-[5-(3,4,5,6-tetrahydro-4-methoxy-2H-pyran-4yl)pyridin-3-yloxy](E-oximino)ethyl]-5-oxazolyl] benzenesulfonamide;

4-[4-(phenyl)-2-[3-(3,4,5,6-tetrahydro-4-methoxy-2H-pyran-4-yl)phenoxy]propyn-1-yl]-5-oxazolyl] benzenesulfonamide;

4-[(phenyl)-5-[4-[4-(methylsulfonyl)phenyl]-2-[3-[3-(3,4,5,6-tetrahydro-4-methoxy-2H-pyran-4-yl)phenoxy]propyn-1yl]oxazole;

4-[4-(phenyl)-2-[3-[3-fluoro-5-(3,4,5,6-tetrahydro-4-methoxy-2H-pyran-4-yl)phenoxy]propyn-1-yl]-5-oxazolyl] benzenesulfonamide;

4-[4-(phenyl)-2-[3-[3-(3,4,5,6-tetrahydro-4-methoxy-2H-pyran-4yl)benzyloxy]propyn-1-yl]-5-oxazolyl]benzenesulfonamide;

4-[4-(phenyl)-2-[3-[3-fluoro-5-(3,4,5,6-tetrahydro-4-methoxy-2H-pyran-4-yl)benzyloxy]propyn-1-yl]-5-oxazolyl]benzenesulfonamide;

4-[4-(phenyl)-2-[3-[3-(3,4,5,6-tetrahydro-4-methoxy-2H-pyran-4-yl)thienyloxy]propyn-1-yl]-5-oxazolyl]benzenesulfonamide;

4-[4- (phenyl)-2-[3-[5-(3,4, 5,6-tetrahydro-4-methoxy-2H-pyran-4 -yl)pyridin-3-yloxy]propyn-1-yl]-5-oxazolyl]benzenesulfonamide;

4-[4-(phenyl)-2-[3-[5-(3,4,5,6-tetrahydro-4-methoxy-2H-pyran-4-yl)pyridin-3 -ylmethoxy]propyn-1-yl]-5-oxazolyl]benzenesulfonamide;

4-[4-(phenyl)-2-[3-[3-(3,4, 5,6-tetrahydro-4-hydroxy-2H-pyran-4 -yl)phenoxy]propyl]-5-oxazolyl]benzenesulfonamide;

4-[4-(phenyl)-5-[4-[4-(methylsulfonyl)phenyl]-2-[3-[3-(3,4,5,6-tetrahydro-4-hydroxy-2H-pyran-4-yl)phenoxy]propyl]oxazole;

4-[4-(phenyl)-2-[3-[3-fluoro-5- (3,4,5,6-tetrahydro-4-hydroxy-2H-pyran-4-yl]phenoxy]propyl]-5-oxazolyl]benzenesulfonamide;

4-[4-(phenyl)-2-[3-[3-(3,4, 5, 6-tetrahydro-4-hydroxy-2H-pyran-4 -yl)benzyloxy]propyl]-5-oxazolyl]benzenesulfonamide;

4-[4-(phenyl)-2-[3-[3-fluoro-5- (3,4,5,6-tetrahydro-4-hydroxy-2H-pyran-4-yl)benzyloxy]propyl]-5-oxazolyl]benzenesulfonamide;

4-[4-(phenyl)-2-[3-[3-(3,4,5,6-tetrahydro-4-hydroxy-2H-pyran-4-yl)-2-thienyloxy]propyl]-5-oxazolyl]benzenesulfonamide;

4-[4-(phenyl)-2-[3-[5-(3,4,5,6-tetrahydro-4-hydroxy-2H-pyran-4-yl)pyridin-3-yloxy]propyl]-5-oxazolyl]benzenesulfonamide;

4-[4-(phenyl)-2-[3-[5-(3,4, 5,6-tetrahydro-4-hydroxy-2H-pyran-4-yl)pyridin-3-ylrmethoxy]propyl]-5-oxazolyl]benzenesulfonamide;

4-[4-(phenyl)-2-[1-hydroxy-2-[3-(2,6-dimethyl-3,4,5,6-tetrahydro-4-hydroxy-2H-pyran-4-yl)benzyloxy]ethyl]-5-oxazolyl]benzenesulfonamide;

4-[4-(phenyl)-2-[1-hydroxy-2-[2-(3,4,5,6-tetrahydro-4-hydroxy-2H-pyran-4-yl)thiazol-4-ylmethoxy]ethyl]-5-oxazolyl]benzenesulfonamide;

4-[1-(phenyl)-2-[1-hydroxy-2-[3-fluoro-5-(1S, 5R 3α-hydroxy-6,8-dioxabicyclo[3.2.1]octanyl)phenoxy]ethyl] -5-oxazolyl]benzenesulfonamide;

4-[4-(phenyl)-2-[[3-(3,4,5,6-tetrahydro-4-methoxy-2H-[pyran-4-yl)phenoxy]methyl]-5-oxazolyl]benzenesulfonamide;

4-[4-(phenyl)-5-[4-[4-(methylsulfonyl)phenyl]-2-[[3-(3,4,5,6-tetrahydro-4-methoxy-2H-pyran-4-yl)phenoxy]methyl]oxazole;

4-[4-(phenyl)-2-[[3-fluoro-5-(3,4,5,6-tetrahydro-4-methoxy-2H-pyran-4-yl)phenoxy]methyl]-5-oxazolyl]benzenesulfonamide;

4-[4-(phenyl)-2-[[3-(3,4,5,6-tetrahydro-4-methoxy-2H-pyran-4-yl)benzyloxy]methyl]-5-oxazolyl]benzenesulfonamide;

4-[4-(phenyl)-2-[[3-fluoro-5-(3,4,5,6-tetrahydro-4-methoxy-2H-pyran-4-yl)benzyloxy]methyl]-5-oxazolyl]benzenesulfonamide;

4-[4-(phenyl)-2-[[3-(3,4,5,6-tetrahydro-4-methoxy-2H-pyran-4-yl)thiophenyl]methyl]-5-oxazolyl]benzenesulfonamide;

4-[4-(phenyl)-2-[[5-(3,4,5,6-tetrahydro-4-methoxy-2H-pyran-4-yl)pyridin-3-yloxy]methyl]-5-oxazolyl]benzenesulfonamide;

4[-4-(phenyl)-2-[[5-(3,4,5,6-tetrahydro-4-methoxy-2H-pyran-4-yl)pyridin-3-ylmethoxy]methyl]-5-oxazolyl]benzenesulfonamide;

4-[4-(phenyl)-2-[3-[3-fluoro-5- (3,4,5,6-tetrahydro-4-hydroxy-2H-pyran-4-yl)phenoxy](Z-propen)-1-yl]-5-oxazolyl]benzenesulfonamide;

4-[4-(phenyl)-2-[3-[3-(3,4,5,6-tetrahydro-4-hydroxy-2H-pyran-4-yl) benzyloxy](E-propen)-1-yl]-5-oxazolyl]benzenesulfonamide;

4-[4-(phenyl)-2-[3-[3-fluoro-5-(3,4,5,6-tetrahydro-4-hydroxy-2H-pyran-4-yl) benzyloxyl(Z-propen)-1-yl]-5-oxazolyl]benzenesulfonamide;

4-[4-(phenyl)-2-[3-[3-(3,4,5,6-tetrahydro-4-hydroxy-2H-pyran-4-yl)thiophenyl](Z-propen)-1-yl]-5-oxazolyl]benzenesulfonamide;

4-[4-(phenyl)-2-[3-[5-(3,4,5,6-tetrahydro-4-hydroxy-2H-pyran-4-yl)pyridin-3-yloxy](Z-propen)-1-yl]-5-oxazolyl]benzenesulfonamide;

4-[4-(phenyl)-2-[3-[5-(3,4,5,6-tetrahydro-4-hydroxy-2H-pyran-4-yl)pyridin-3-ylmethoxy](Z-propen)-1-yl]-5-oxazolyl]benzenesulfonamide;

4-[4-(phenyl)-5-[4-[4-(methylsulfonyl)phenyl]-2-[[3-(3,4,5,6-tetrahydro-4-methoxy-2H-pyran-4-yl)phenoxy]-1,2,3-triazol-4-ylmethyl-5-]-5-oxazolyl]benzenesulfonamide;

4-[4-(phenyl)-2-[[3-fluoro-5-[3,4,5,6-tetrahydro-4-methoxy-2H-pyran-4-yl) phenoxy]-1,2,3-triazol-4-ylmethyl-5-]-5-oxazolyl]benzenesulfonamide;

4-[4-(phenyl)-2-[[3-(3,4,5,6-tetrahydro-4-methoxy-2H-pyran-4-yl) benzyloxy]-1,2,3 -triazol-4-ylmethyl-5-]-5-oxazolyl]benzenesulfonamide;

4-[4-(phenyl)-2-[[3-fluoro-5-(3,4, 5,6-tetrahydro-4-methoxy-2E-pyran-4-yl)benzyloxy]-1,2,3 -triazol-4-ylmethyl-5-]-5-oxazolyl]benzenesulfonamide;

4-[4-(phenyl)-2-[[3-(3,4,5,6-tetrahydro-4-methoxy-2H-pyran-4-yl)thiophenyl]-1,2,3-triazol-4-ylmethyl-5-]-5-oxazolyl]benzenesulfonamide;

4-[4-(phenyl)-2-[[5-(3,4,5,6-tetrahydro-4-methoxy-2H-pyran-4-yl)pyridin-3-yloxy]-1,2,3-triazol-4-ylmethyl-5-]-5-oxazolyl]benzenesulfonamide;

4-[4-(phenyl)-2-[[5-(3,4,5,6-tetrahydro -4-methoxy-2H-pyran-4-yl)pyridin-3-ylmethoxy]-1,2,3 -triazol-4-ylmethyl-5-]-5-oxazolyl]benzenesulfonamide;

4-[4-(phenyl)-2-[3-[[3-(3,4,5,6-tetrahydro-2H-pyran-4-yl)]Z-oximinomethyl]phenoxy]propyn-1-yl]-5-oxazolyl]benzenesulfonamide;

4-[4-(phenyl)-2-[3-[[3-(3,4,5,6-tetrahydro-2H-pyran-4-yl)]E-oximinomethyl]phenoxy]propyn-1-yl]-5-oxazolyl]benzenesulfonamide;

4-[4-(phenyl)-2-[3-[E-O-methyl-[3-(3,4,5,6-tetrahydro-2H-pyran-4-yl)]oximinomethyl]phenoxy]propyn-1-yl]-5-oxazolyl]benzenesulfonamide;

4-[4-(phenyl)-2-[3-[Z-O-methyl-[3-(3,4,5,6-tetrahydro-2H-pyran-4-yl)]oximinomethyl]phenoxy]propyn-1-yl]-5-oxazolyl]benzenesulfonamide;

4-[4-(phenyl)-2-[3-[3-(3,4,5,6-tetrahydro-4-methoxy-2H-pyran-4-yl)phenyl]propyn-1-yl]- 5-oxazolyl]benzenesulfonamide;

4-[4-(phenyl)-5-[4-[4-(methylsulfonyl)phenyl]2-[3-[3-(3,4, 5,6-tetrahydro-4-methoxy-2H-pyran-4-yl)phenyl]propyn-1-yl]oxazole;

4-[4-(phenyl)-Z-[3-[3-fluoro-5-(3,4,5,6-tetrahydro-4-methoxy-2H-pyran-4-yl)phenyl]propyn-1-yl]-5-oxazolyl]benzenesulfonamide;

4- [4-(phenyl)-2-[3-[5-(3,4,5,6-tetrahydro-4-methoxy-2H-pyran-4-yl)pyridin-3-yl ]propyn-1-yl]-5-oxazolyl]benzenesulfonamide;

4-[4-(phenyl)-2-[3-[3-(2,6-dimethyl-3,4,5,6-tetrahydro-4-methoxy-2H-pyran-4-yl)phenyl]propyn-1-yl]-5-oxazolyl]benzenesulfonamide;

4-[4-(phenyl)-2-[3-[2-(3,4,5,6-tetrahydro-4-methoxy-2H-pyran-4-yl)thiazol-4-yl]propyn-1-yl]-5-oxazolyl]benzenesulfonamide;

4-[4-(phenyl)-2-[3-[3-fluoro-5-(1S, 5R 3α-methoxy-6,8-dioxabicyclo[3.2.1]octanyl)phenyl]propyn-1-yl]-5-oxazolyl]benzenesulfonamide;

4-[4-(phenyl)-2-[3-[3-(3,4,5,6-tetrahydro-4-hydroxy-2H-pyran-4-yl)phenyl]propyn-1-yl ]-5-oxazolyl]benzenesulfonamide;

4-[4-(phenyl)-5-[4-[4-(methylsulfonyl)phenyl]-2-[3-[3-(3,4,5,6-tetrahydro-4-hydroxy-2H-pyran-4-yl)phenyl]propyn-1-yl]oxazole;

4-[4-(phenyl)-2-[3-[2-(3,6,5,6tetrahydro-4-hydroxy-2H-pyran-4-yl)thiazol-4-yl]propyl]-5-oxazolyl]benzenesulfonamide; and 4-[4-(phenyl)-2-[3-[3-fluoro-5-(1S, 5R 3α-hydroxy-6,8-dioxabicyclo [3.2.1]octanyl)phenyl]propyn-1-yl]-5-oxazolyl]benzenesulfonamide.

7. A compound of Formula II

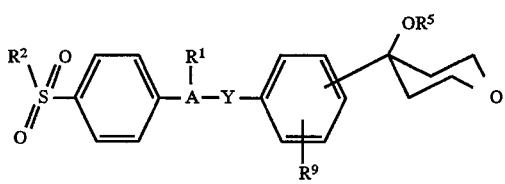

wherein A is a ring substituent selected from oxazolyl and isoxazolyl, wherein A is optionally substituted with a radical selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl;

wherein Y is a radical selected from oxy, thio, sulfinyl, sulfonyl, lower alkyl, lower alkynyl, lower alkenyl, lower hydroxyalkyl, azyl, lower cycloalkyl, 5- or 6-membered heterocyclo, aralkyl, lower alkyloxy, aryloxy, arylthio, lower cycloalkyloxy, 5- or 6-membered heterocyclooxy, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkyloxyalkyl, lower alkylthioalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower carbonylalkylthio, lower carbonylalkylthioaikyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, and lower carbonylalkyloxyalkyi;

wherein R¹ is a substituent selected from 5- and 6-membered heterocyclo, lower cycloalkyl, lower cycloalkenyl and aryl selected from phenyl, biphenyl and naphthyl, wherein R¹ is optionally substituted at a substitutable position with one or more radicalslselected from lower alkyl, lower haloalkyl, cyano, carboxyl, lower alkoxycarbonyl, hydroxyl, lower hydroxyalkyl, lower haloalkoxy, amino, lower alkyiamino, phenylamino, nitro, lower alkoxyalkyl, lower alkylsulfinyl, halo, lower alkoxy and lower alkylthio;

wherein R² is selected from lower alkyl and amino;

wherein R⁵ is selected from hydrido, alkyl, alkenyl, alkynyl, cyanoalkyl, alkanoyl, and benzoyl optionally substituted with a substituent selected from halo, alkyl, and alkoxy; and wherein R⁹ is one or two substituents selected from halo, hydroxyl, amino, nitro, cyano, carbamoyl, alkyl, alkenyloxy, alkoxy, alkylthio, alklysulfinyl, alkylsulfonyl, alkylamino, dialkylamino, haloalkyl, alkoxycarbonyl, N-alkylcarbamoyl, N,N-dialkylcarbamoyl, alkanoylamino, cyanoalkoxy, carbamoylalkoxy, and alkoxycarbonylalkoxy; or a pharmaceutically-accepptable salt thereof.

8. Compound of claim 7 wherein A is a radical selected from oxazolyl, and isoxazolyl, wherein A is optionally substituted with a radical selected from acyl, halo, hydroxyl, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, lower alkyl, lower alkynyl, 5- or 6-membered heterocyclo, lower hydroxyalkyl, lower alkyloxy, lower alkylthio, lower alkloxyalkyl, lower alkenyloxy, lower alkenyloxyalkyl; lower alkynyloxy, lower alkynylthio, lower alkynyloxyalkyl, lower hydroxyalkylthio, lower hydroxyalkylthioalkyl, lower oximinoalkylthio, lower oximinoalkylthioalkyl, lower (alkyl) oximinoaalkylthio, lower (alkyl) oximinoalkylthioalkyl, lower carbonylalkylthio, lower carbonylalkylthioalkyl, lower hydroxyalkyloxy, lower hydroxyalkyloxyalkyl, lower oximinoalkoxy, lower oximinoalkoxyalyl, lower (alkyl) oximinoalkoxy, lower (alkyl)oximinoalkoxyalkyl, lower carbonylalkyloxy, and lower carbonylalkyloxyalkyl; wherein R¹ is phenyl optionally substituted at a substitutable position with one or more radicals selected from lower alkyl, lower haloalkyl, hydroxyl, lower hydroxyalkyl, nitro, halo, and lower alkoxy; wherein R² is selected from lower alkyl and amino; wherein R⁵ is selected from hydrido, and lower alkyl; and wherein R⁹ is one or two substituents selected from halo, hydroxyl, arnino, lower alkyl, lower alkoxy; or a pharmaceutically-acceptable salt thereof.

9. Compound of claim 8 wherein A is a radical selected from oxazolyl, and isoxazolyl, wherein A is optionally substituted with a radical selected from formyl, fluoro, chloro, bromo, hydrorql, methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, oxo, eTano, nitro, carboxyl, methoxy, ethoxy, propoxy, n-butoxy, pentoxy, hexyloxy, methylenedioxy, aminocarbonyl, methoxycarbonyl, carboxypropyl, carborymethyl, carboxyethyl, cyanomethyl, and hydroxymethyl; wherein Y is a radical selected from oxy, ethyl, isopropyl, butyl, 1-propynyl, 2-propynyl, methyloxy, ethyloxy, proDyloxy, methylthio, (Z)-1-propenyloxy, (E)-2-propenyloxy, (Z)-2-propenyloxy, (E)-1-propenyloxy, Z)-1-propenyloxymethyl, (E)-2-propenyloxymethyl, (Z) -2-propenyloxymethyl, (E)-1-propenyloxymethyl, 1-propynyloxy, 2-propynyioxy, 1-propynylthio, 2-propynylthio, hydroxymethyl, hydroxyethyl, hydropropyl, hydroxymethyloxy, 1-hydroxyethyloxy, 2-hydroxypropyloxy, hydroxymethyloxymethyl, 1-hydroxyethyloxymethyl, 2-hydroxypropyloxymethyl, methyloxymethyl, ethyloxymethyl, propyloxymethyl, 1-propynyloxymethyl, hydroxymethylthio, 1 -hydroxyethylthio, 2-hydroxypropylthio, hydroxymethylthiomethyi, 1-hydroxyethylthiomethyl, 2 -hydroxypropylthiomethyl, oximinomethylthio, oximinomethylthiomethyl, (methyl)

oximinomethylthio, (methyl)oximinomethylthiomethyl, triazolylmethyloxy, triazolylmethyloxymethyl, carbonylmethylthio, carbonylbutylthio, carbonylmethylthiomethyl, oximinomethyloxy, oximinomethyloxymethyl, (methyl) oximinomethyloxy, (methyl)oximinomethyloxymethyl, triazolyl, carbonylmethyloxy, carbonylbutyloxy, and carbonylmethyloxymethyl; wherein $R^1$ is phenyl optionally substituted at a substitutable position with one or more radicals selected from methyl, ethyl, isopropyl, butyl, tert-butyl, isobutyl, pentyl, hexyl, fluoromethyl, difluoromethyl, trifluoromethyl, chloromethyl, dichloromethyl, trichloromethyl, pentafluoroethyl, heptafluoropropyl, fluoromethyl, difluoroethyl, difluoropropyl, dichloroethyl, dichloropropyl, hydroxyl, hydroxymethyl, nitro, fluore, chloro, bromo, methoxy, ethoxy, propoxy, n-butoxy, pentoxy, and hexyloxy; wherein $R^2$ is selected from methyl, ethyl, isopropyl, butyl, tert-butyl, isobutyl, pentyl, hexyl, and amino; wherein $R^5$ is selected from hydrido, and methyl, ethyl, isopropyl, butyl, tert-butyl, isobutyl, pentyl, hexyl; and wherein $R^9$ is one or two substituents selected from fluoro, chloro, bromo, hydroxyl, andno, methyl, ethyl, isopropyl, butyl, tert-butyl, isobutyl, pentyl, hexyl, methoxy, ethoxy, propoxy, n-butoxy, pentoxy, and hexyloxy; or a pharmaceutically-acceptable salt thereof.

10. A pharmaceutical composition comprising a therapeutically-effective amount of a compound, said compound selected from a family of compounds of Formula I

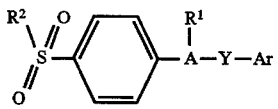

wherein A is oxazolyl or isoxazolyl, wherein A is optionally substituted with a radical selected from acyl, halo, alkyl, haloalkali, cyano, nitro, carboxyl, alkoxy, oxo, aminocarbonyl, alkoxycarbonyl, carboxyalkyl, cyanoalkyl, and hydroxyalkyl;

wherein Y is a radical selected from oxy, thio, sulfinyl, sulfonyl, alkyl, alkenyl, alkynyt, alkyloxy, alkylthio, alkylcarbonyl, cycloalkyl, aryl, haloalkyl, hydroxyalkyl, hydroxyalkyloxy, hydroxyalkyloxyalkyl, hydroxyalkylthio, hydroxyalkylthioalkyl, oximinoalkoxy, oxminoalkoxyalkyl, (alkyl) oximinoalkoxy, (alkyl) oximinoalkoxyalkyl, oximinoalkylthio, oximinoalkylthioalkyl, (alkyl) oximinoalkylthio, (alkyl) oximinoalkyl thioalkyl, carbonylalkloxy, carbonylalkyloxyalkyl, carbonylalkylthio, carbonylalkylthioalkyl, heterocyclo, cycloalkenyl, aralkyl, heterocycloalkyl, acyl, alkylthioalkyl, alkyloxyalkyl, alkenylthio, alkynylthio, alkenyloxy, alkynyloxy, alkenylthioalkyl, alkynylthioalkyl, alkenyloxyalkyl, alkynyloxyalkyl, arylcarbonyl, aralkylcarbonyl, aralkenyl, haloalkylcarbonyl, alkoxyalkyl, alkylaminocarbonylalkyl, heteroaralkoxyalkyl, heteroaryloxyalkyl, heteroarylthioalkyl, heteroaralkylthioalkyl, heteroaralkoxy, heteroaralkylthio, heteroaryloxy, heteroarylthio, arylthioalkyl, aryloxyalkyl, haloaryloxyalkyl, aralkylthioalkyi, aralkoxyalkyl, alkoxyaralkoxyalkyl, alkoxycarbonylalkyl, alkoxycarbonylcyanoalkenyl, arainocarbonylalkyl, N-alkylaminocarbonyl, N-arylaminocarbonyt, N, N-dialkylaminocarbonyl, N-albyl-N-arylaminocarbonyl, cycloalkylaminocarbonyl, heterocycloaminocarbcnyl, carboxyalkylaminocarbonyl, alkylcarbonylalkyl, aralkoxycarbonylalkylaminocarbonyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyl-N-aralkylamino, N-alkyl-N-arylamino, aminoalkylamino, N-alkylaminoalkyl, N,N-dialktflaminoalkyl, N-arylaminoalkyl, N-aralkylaminoalkyl, N-alkyl-N-aralkylaminoalkyl, N-alkyl-N-arylaminoalkyl, aminoalkoxy, aminoalkoxyalkyl, aminoalkylthio, aminoalkylthioalkyl, cycloalkyloxy, cycloalkylalkyloxy, aryloxy, aralkoxy, arylthio, aralkylthio, alkylsulfinyl, alkylsulfonyl, aminosulfonyl, N-alkylarainosulfonyl, N-arylaminosulfonyl, arylsulfonyl, N,N-dialkylaminosulfonyl, N-alkyl-N-arylaminosulfonyl,

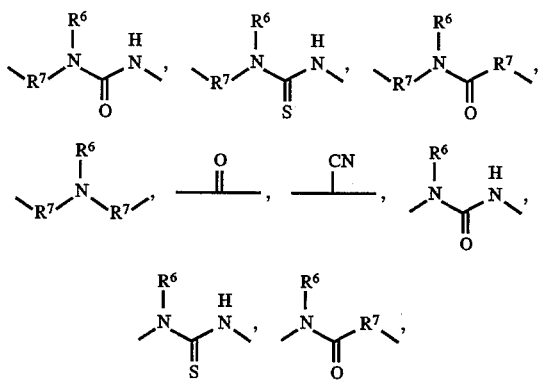

wherein Ar is selected from aryl and heteroaryl, wherein Ar is optionally substituted with one or two substituents selected from halo, hydroxyl, amino, nitro, cyano, carbaraoyi, alkyl, alkenyloxy, alkoxy, alkylthio, alkylsulfinyl, alkylsulfonyl, alkylamino, dialkylamino, haloalkyl, alkoxycarbonyl, N-alklcarbamoyl, N,N-dialkylcarbamoyl, alkanoylamino, cyanoalkoxy, carbamoylalkoxy, alkoxycarbonylalkoxy and

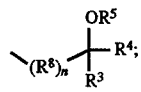

wherein $R^1$ is at least one substituent selected from heterocyclo, cycloalkyl, cycloalkenyl and aryl, wherein $R^1$ is optionally substituted at a substitutable position with one or more radicals selected from alkyl, haloalbyl, cyano, carboxyl, alkoxycarbonyl, hydroxyl, hydroxyalkyl, haloalkoxy, amino, alkylamino, arylamino, nitro, alkoxyalkyl, alkylsulfinyl, halo, alkoxy and alkylthio; wherein $R^2$ is selected from alkyl and amino; wherein $R^3$ and $R^4$ together form a group of the formula —B—X—B' which together with the carbon atom to which B and B1 are attached, defines a ring having 6 ring atoms, wherein B and $B^1$, which may be the same or different, each is alkylene and X is oxy, and which ring may bear one, two or three substituents, which may be the same or different, selected from hydroxyl, alkyl, alkoxy, alkenyloxy and alkynyloxy; wherein $R^5$ is selected from hydrid;oalkyl, alkanoyl, and aroyl optionally substituted with a substituent selected from halo, alkyl and alkoxy;

wherein R⁶ is selected from hydrido, alkyl, aryl and aralkyl;
wherein R⁷ is selected from alkyl, alkenyl and alkynyl;
wherein R⁸ is oximino optionally substituted with alkyl; and
wherein n is 0 or 1;
provided Ar is substituted with

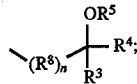

or a pharmaceutically-acceptable salt thereof.

11. The composition of claim 10 wherein A is a radical selected from oxazolyl, and isoxazolyl, wherein A is optionally substituted with a radical selected from acyl, halo, lower alkyl, lower haloalkyl, oxo, cyano, nitro, carboxyl, lower alkoxy, aminocarbonyl, lower aikoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkloxy, lower hydroxyalkyloxyalkyl, lower oximinoalkoxy, lower oximinoalkoxyalkyl, lower (alkyl) oximinoalkoxy, lower (alkyl) oximinoalkoxyalkyl, lower carbonylalkyloxy, lower carbonylalkyloxyalkyyl, lower hydroxyalkylthio, lower hydroxyalkylthioalkyl, lower oximinoalkylthio, lower oximinoalkylthioalkyl, lower (alkyl) oximinoalkylthio, lower (alkyl) oximinoalkylthioalkyl, lower carbonylalkylthio, lower carbonylalkylthioalkyl, lower alkylthio, lower alkylcarbonyl, lower cycloalkyl, phenyl, lower haloalkyl, 5- or 6-membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower heteroaralkoxyalkyl, lower heteroaryloxyalkyl, lower heteroarylthioalkyl, lower heteroaralkylthioalkyl, lower heteroaralkoxy, lower heteroaralkylthio, lower heteroaryloxy, lower heteroarylthio, lower arylthioalkyl, lower aryloxyalkyl, lower aralkylthioalkyl, lower aralkoxyalkyl, lower alkoxyaralkoxyalkyl, lower alkoxycarbonylalkyl, lower alkoxycarbonylcyanoalkenyl, lower aminocarbonylalkyl, lower N-alkylaminocarbonyl, N-phenylaminocarbonyl, lower N,N-dialkylaminocarbonyl, lower N-alkyl-N-arylaminocarbonyl, lower cycloalkylaminocarbonyl, lower heterocycloarainocarbonyl, lower carboxyalkylaminocarbonyl, lower alkylcarbonylalkyl, lower aralkoxycarbonylalkylaminocarbonyl, lower haloaralkyl, lower carboxyhaloalkyl, lower alkylcarbonylhaloalkyl, lower aminocarbonylhaloalkyl, lower alkylaminocarbonylhaloalkyl, lower N-alkylamino, lower N,N-dialkylamino, N-phenylamino, lower N-aralkylamino, lower N-alkyl -N-aralkylamino, lower N-alkyl-N-arylamino, lower aminoalkyl, lower N-alkylaminoalkyl, lower N,N-dialkylaminoalkyl, lower N-arylaminoalkyl, lower N-aralklaminoalkyl, lower N-alkyl-N-aralkylaminoalkyl, lower N-alkyl-N-arylaminoalkyl, lower aminoalkoxy, lower aminoalkoxyalkyl, lower aminoalkylthio, lower aminoalkylthioalyl, lower cycloalkyloxy, lower cycloalkylalkyloxy, phenyloxy, lower aralkoxy, phenylthio, lower aralbylthio, lower alkylsulfinyl, lower alkylsulfonyl, aminosulfonyl, lower N-alkylantinosuifonyl, lower N-arylaminosulfonyl, lower arylsulfonyi, lower dialkylaminosulfonyl, lower N-alkyl-N-arylaminosulfonyl,

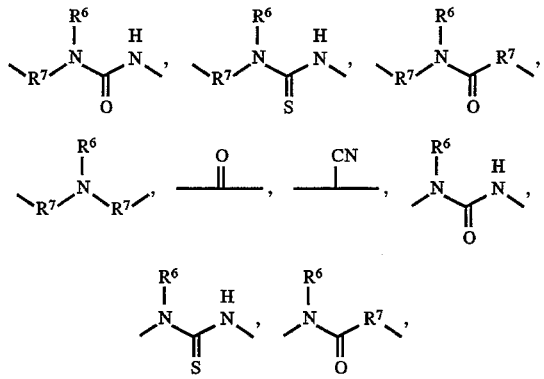

wherein Ar is selected from aryl selected from phenyl, biphenyl and naphthyl, and 5- and 6-membered heteroaryl, wherein Ar is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkytsulfonyl, lower alkylamino, lower dialkylamino, lower haloalkyl, lower alkoxycarbonyi, lower N-alkylcarbamoyl, lower N,N-dialkylcarbamoyl, lower alkanoylamino, lower cyanoalkoxy, lower carbamoylalkoxy, lower alkoxycarbonylalkoxy and

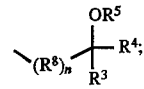

wherein R¹ is at least one substituent selected from 5- and 6-membered heterocyclo, lower cycloalkyl, lower cycloalkenyl and aryl selected from phenyl, biphenyl and naphthyl, wilere R¹ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylarmino, nitro, lower alkoxyalkyl, lower alkylsulfinyl, halo, lower alkoxy and lower alkylthio; wherein R² is selected from lower alkyl and amino; wherein R³ and R⁴ together form a group of the formula —B—X—B¹ which together with the carbon atom to which B and B¹ are attached, defines a ring having 6 ring atoms, wherein B and B¹, which may be the same or different, each is alkylene and X is oxy, and which ring may bear one, two or three substituents, which may be the same or different, selected from hydroxyl, lower alkyl, lower alkoxy, lower alkenyloxy and lower alkynyloxy; wherein R⁵ is selected from hydrido, lower alkyl, lower alkenyl, lower alkynyi, lower cyanoalkyl, lower alkanoyl, and benzoyl optionally substituted with a substituent selected from halo, lower alkyl and lower alkoxy; wherein R⁶ is selected from hydrido, lower alkyl, phenyl and lower aralkyl; wherein R7 is selected from lower alkyl, lower alkenyl and lower alkynyl; wherein R⁸ is oximino optionally substituted with alkyl; and wherein n is 0 or 1; or a pharmaceutically-acceptable salt thereof.

12. The composition of claim 11 wherein A is a radical selected from oxazolyl, and isoxazolyl, wherein A is optionally substituted with a radical selected from acyi, halo, lower alkyl, lower haloalkyl, oxo, cyano, nitro, carboxyl, lower alkoxy, arminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, lower carbonylalkyloxyalkyl, lower hydroxyalkylthio, lower hydroxyalkylthioalkyl, lower oximinoalkalkylthio, lower oximinoalkylthioalkyl, lower (alkyl)oximinoaikylthio, lower (alkyl)oximinoalkylthioalkyl, lower carbonyiatkylthio, lower carbonylalkylthioalkyl, alkylthio, lower alkylcarbonyl, lower cycloalkyl, phenyl, lower haloalkyl, 5- or 6membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylaikyl, lower arylthioalkyl, lower aryloxyalkyl, lower aralkylthioalkyl, lower aralkoxyalkyl, lower alkoxycarbonylalkyl, lower aminocarbonylalkyl, lower N-alkylaminocarbonyl, N-phenylaminocarbonyl, lower alkylcarbonylalkyl, lower alkylamino, N-phenylamino, lower N-aralbylamino, lower aminoalkyl, lower N-alkylaminoalk-yl, lower N-arylaminoalkyl, lower N-aralkylaminoalkyl, lower aminoalkoxy, lower aminoalkoxyalbyl, lower aminoalkylthio, lower aminoalkylthioalkyl, lower cycloalkyloxy, lower cycloalkylalkyloxy, phenyloxy, lower aralkoxy, phenylthio, lower aralkylthio, lower alkylsulfinyl, lower alkylsulfonyl, aminosul fonyl, lower N-alkylaminosulfonyl, N-phenylaminosulfonyl, phenylsui fonyl, oximino,

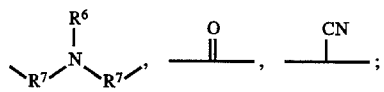

wherein Ar is selected from aryl selected from phenyl, biphenyl, naphthyl, and 5- and 6-merebored heteroaryl, wherein Ar is optionally substituted with one or two substituents selected from halo, hydroxyl, amino, nitro, cyano, lower alkyl, lower alkoxy, and

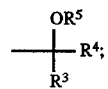

wherein $R^1$ is at least one substituent selected from 5- and 6-membered heteroaryl, and aryl selected from phenyi, biphenyl and naphthyl, where $R^1$ is optionally substituted at a substitutable position with one or more radicals selected from lower alkyl, lower haloalkyt, cyano, carboxyl, lower alkoxycarbonyl, hydroxyl, lower hydroxyalkyl, lower haloalkoxy, amino, nitro, lower alkoxyalkyl, lower alkylsulfinyl, halo, lower alkoxy and lower alkylthio; wherein $R^2$ is selected from lower alkyl and amino; wherein $R^3$ and $R^4$ together form a tetrahydropyran ring and which ring may bear one, two or three substituents, which may be the same or different, selected from hydroxyl, lower alkyl, and lower alkoxy; wherein $R^5$ is selected from hydrido and lower alkyl; wherein $R^6$ is selected from hydrido, lower alkyl, phenyl and lower aralkyl; and wherein $R^7$ is selected from lower alkyl, lower alkenyl and lower alkynyl; provided Ar is substituted with

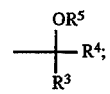

or a pharmaceutically-acceptable salt thereof.

13. The composition of claim 12 wherein A is a radical selected from oxazolyl, and isoxazolyl, wherein A is optionally substituted with a radical selected from acyl, halo, lower alkyl, lower haloalkyl, oxo, cyano, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkynyl, lower alkenyl, aryl, lower cycloalkyl, 5- or 6-membered heterocyclo, aralkyl, lower alkyloxy, aryloxy, arylthio, 5-or 6-membered heterocloxy, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkloxyalkyl, lower alkylthioalkyl, lower hydroxyalkyloxy, lower hydroxyalkyloxyatkyl, lower oximinoalkoxy, lower oximinoalkoxyalkyl, lower (alkyl) oximinoalkoxy, lower(alkyl)oximinoalkoxyalkyl, lower carbonylalkyloxy, and lower carbonylalkyloxyalkyl; wherein Ar is selected from phenyl, thienyl, oxazolyl, furyl, pyrrolyi, thiazolyl, imidazolyl, isothiazolyl, isoxazolyl, pyrazolyl, cyclopentenyl, and pyridyl, wherein Ar is optionally substituted with one or two substituents selected from halo, hydroxyl, lower alkyl, lower alkoxy, and

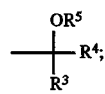

wherein $R^1$ is at least one substituent selected from thienyl, oxazolyl, furyl, pyrrolyl, thiazolyl, imidazolyl, isothiazolyl, isoxazolyl, pyrazolyl, cyclopentenyl, pyridyi, and phenyl, where $R^1$ is optionally substituted at a substitutable position with one or more radicals selected from lower alkyl, lower haloalkyl, hydroxyl, lower hydroxyalkyl, lower haloalkoxy, nitro, lower alkoxyalkyl, halo, lower alkoxy and lower alkylthio; wherein $R^2$ is selected from lower alkyl and amino; wherein $R^3$ and $R^4$ together form a tetrahydropyran ring, and which ring may bear one, two or three substituents, which may be the same or different, selected from hydroxyl, lower alkyl, and lower alkoxy; and wherein $R^5$ is selected from hydrido and lower alkyl; or a pharmaceutically-acceptable salt thereof.

14. The composition of claim 13 wherein A is a radical selected from oxazolyl, and isoxazolyl, wherein A is optionally substituted with a radical selected from acyl, fluoro, chloro, bromo, methyl, trifluoromethyl, oxo, cyano, carboxyl, methoxy, aminocarbonyl, methoxycarbonyl, ethoxycarbonyl, acetyl, carboxypropyl, and hydroxymethyl; wherein Y is a radical selected from oxy, ethyl, isopropyl, butyl, 1-propynyl, 2-propynyl, methyloxy, ethyloxy, propyloxy, methylthio, (Z)-1-propenyloxy, (E)-2-propenyloxy, (Z)-2-propenyloxy, (E)-1-propenyloxy, Z)-1-propenyloxTfmethyl, (E)-2-propenyloxymethyl, (Z) -2-propenyloxymethyl, (E) -1-propenyloxyrnethyl, 1-propynyloxy, 2-propynyloxy, 1-propynylthio, 2-propynylthio, hydroxymethyloxy, 1-hydroxyethyloxy, 2-hydroxypropyloxy, hydroxymethyloxymethyl, 1-hydroxyethyloxymethyl, 2-hydroxypropyloxymethyl, methoxymethyl, ethyloxymethyl, propyloxyraethyl, 1-propynyloxymethyl, oximinomethyloxy, oximinomethyloxymethyl, (methyl)oximinomethyloxy, (methyl)oximinomethyloxymethyl, triazolylmethyloxy, triazolylmethyloxymethyl, carbonylmethyloxy, carbonylbutyloxy, and carbonylmethyloxymethyl; wherein Ar is selected from phenyl, thienyl, oxazolyl, furyl, pyrrolyl, thiazolyl, imidazolyl, isothiazolyl, isoxazolyl, pyrazolyl, cyclopentenyl, and pyridyl, wherein Ar is substituted with

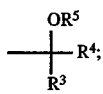

wherein $R^1$ is selected from thienyl, oxazolyl, furyl, pyrrolyl, thiazolyl, imidazolyl, isothiazolyl, isoxazolyl, pyrazolyl, cyclopentenyl, pyridyl, and phenyl, where $R^1$ is optionally substituted at a substitutable position with one or more radicals selected from methyl, trifluoromethyl, hydroxyl, hydroxymethyl, trifluoromethoxy, nitro, methoxymethyl, fluoro, chloro, bromo, methoxy and methylthio; wherein $R^2$ is methyl or amino; wherein $R^3$ and $R^4$ together form a tetrahydropyran ring, and which ring may bear one, two or three substituents, which may be the same or different, selected from hydroxyl, methyl, and methoxy; and wherein $R^5$ is selected from hydrido and methyl; or a pharmaceutically-acceptable salt thereof.

15. A pharmaceutical composition comprising a therapeutically-effective amount of a compound, said compound selected from a fantily of compounds of claim 6, or a pharmaceutically-acceptable salt thereof.

16. A pharmaceutical composition comprising a therapeutically-effective amount of a compound, said compound selected from a family of compounds of claim 7, or a pharmaceutically-acceptable salt thereof.

17. A method of treating a condition benefitedby the inhibition of 5-lipoxygenase, cyclooxygenase-2 or both 5-lipoxygenase and cyclooxygenase-2, said method comorising administering to the subject having or susceptible to such inflammation or inflammation-associated disorder, a therapeutically-effective amount of a compound of Formula I

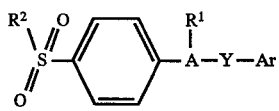

wherein A is oxazolyl or isoxazolyl, wherein A is optionally substituted with a radical selected from acyl, halo, alkyl, haloalkyl, cyano, nitro, carboxyl, alkoxy, oxo, aminocarbonyl, alkoxycarbonyl, carboxyalkyl, cyanoalkyl, and hydroxyalkyl;

wherein Y is a radical selected from oxy, thio, sulfinyl, sulfonyl, alkyi, alkenyl, alkynyl, alkyloxy, alkylthio, alkycarbonyl, cycloalkyl, aryl, haloalkyl, hydroxyalkyl, hydrokyalkyloxy, hydroxyalkyloalkyl, hydroxyalkylthio, hydroxyalkylthioalkyl, oximinoalkoxy, oximinoalkoxyalkyl, (alkyl)oximinoalkoxy, (alkyl)oximinoalkoxyalkyl, oximinoalkylthio, oximinoalkylthioalkyl, (alkyl) oximinoalkylthio, (alkyl)oximinoalkylthioalkyl, carbonylalkyloxy, carbonylalkyloxyalkyl, carbonylalkylthio, carbonylalkylthioalkyl, heterocyclo, cycloalkenyl, aralkyl, heterocycloalkyl, acyl, alkylthioalkyl, alkyloxyalkyl, alkenylthio, alkynylthio, alkenyloxy, alkynyloxy, alkenylthioalkyl, alkynylthioalkyl, alkenyloxyalkyl, alkynyloxyalkyl, azylcarbonyl, aralkylcarbonyl, aralkenyl, haloalkylcarbonyl, alkoxyalkyl, alkylaminocarbonylalkyl, heteroaralkoxyalkyl, heteroaryloxyalkyl, heteroarylthioalkyl, heteroaralkylthioalkyl, heteroaralkoxy, heteroaralkylthio, heteroaryloxy, heteroarylthio, arylthioalkyl, arytoxyalkyl, haloaryloxyalkyl, aralkylthioalkyl, aralkoxyalkyl, alkoxyaralkoxyalkyl, alkoxycarbonylalkyl, alkoxycarbonylcyanoalkenyl, aminocarbonylalkyl, N-alkylaminocarbonyl, N-arylaminocarbonyl, N,N-dialkylaminocarbonyl, N-alkyl-N-arylaminocarbonyl, cycloalkylaminocarbonyl, heterocycloaminocarbonyl, carboxyalkylaminocarbonyi, alkylcarbonylalkyl, aralkoxycarbonylalkylaminocarbonyl, haloaralkyl, carboxyhaloalkyl, alkoxycarbonylhaloalkyl, aminocarbonylhaloalkyl, alkylaminocarbonylhaloalkyl, N-alkylamino, N,N-dialkylamino, N-arylamino, N-aralkylamino, N-alkyi-N-aralkylamino, N-alkyl-N-arylamino, aminoalkyl, N-alkylaminoalkyl, N, N-dialkylaminoalkyl, N-arylaminoalkyl, N-aralkylaminoalkyl, N-alkyl-N-aralkylaminoalkyl, N-alkyl-N-arylaminoalkyl, aminoalkoxy, aminoalkoxyalkyl, aminoalkylthio, aminoalkylthioalkyl, cycloalkyloxy, cycloalkylalkyloxy, aryloxy, aralkoxy, arylthio, aralkylthio, alkylsulfinyl, alkylsulfonyl, aminosulfonyl, N-alkylaminosulfonyl, N-arylaminosulfonyl, arylsulfonyl, N, N-dialkylaminosulfonyl, N-alkyl-N-arylaminosulfonyl,

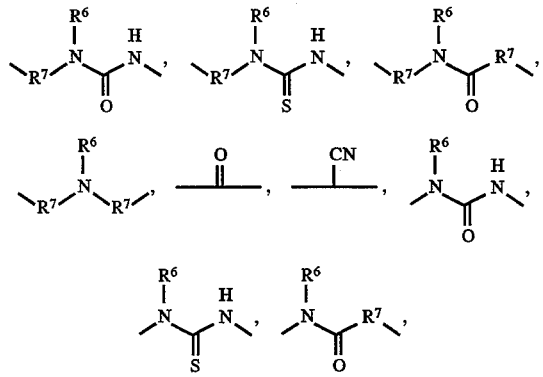

wherein Ar is selected from aryi and heteroaryl, wherein Ar is optionally substituted with one or two substituents selected from halo, hydroxyl, arnino, nitro, cyano, carbamoyl, alkyl, alkenyloxy, alkoxy, alkylthio, alkylsulfinyl, alkylsulfonyl, alkylamino, dialkylamino, haloalkyl, alkoxycarbonyl, N-alkylcarbamoyl, dialkylcarbamoyl, alkanoylamino, cyanoalkoxy, carbamoylalkoxy, alkoxycarbonylalkoxy and

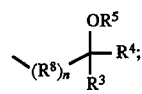

wherein $R^1$ is at least one substituent selected from heterocyclo, cycloalkyl, cycloalkenyl and aryl, wherein $R^1$ is optionaily substituted at a substitutable position with one or more radicals selected from alkyl, haloalkyl, cyano, carboxyl, aikoxycarbonyl, hydroxyl, hydroxyalkyl, haloalkoxy, amino, alkylamino, arylamino, nitro, alkoxyalkyl, alkylsulfinyl, halo, alkoxy amd alkylthio;

wherein $R_2$ is selected from alkoxy and amino; wherein $R^3$ and $R^4$ together form a group of the formula —B—X—$S^1$ which together with the carbon atom to which B and $B^1$ are attached, defines a ring having 6 ring atoms, wherein B and $B^1$, which may be the same or different, each is alkylene and X is oxy, and which ring may bear one, two or three substituents, which may be the same or different, selected from hydroxyl, alkyl, alkoxy, alkenyloxy and alkynyloxy;

wherein $R^5$ is selected from hydrido, alkyl, alkanoyl, and aroyl optionally substituted with a substituent selected from halo, alkyl and alkoxy;

wherein $R^6$ is selected from hydrido, alkyl, aryl and aralkyl;

wherein $R^7$ is selected from alkyl, alkenyl and alkynyl;

wherein $R^8$ is oximino optionally substituted with alkyl; and wherein n is 0 or 1;

provided Ar is substituted with

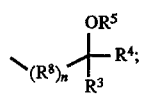

or a pharmaceutically-acceptable salt thereof.

18. The method of claim 17 wherein A is a radical selected from oxazolyl, and isoxazolyl, wherein A is optionally substituted with a radical selected from acyl, halo, lower alkyl, lower haloalkyl, oxo, cyano, nitro, carboxyl, lower alkoxy, aminocarbonyl, lower alkoxycarbonyi, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxyalkyloxyalkyl, lower oximinoalkoxy, lower oximinoalkoxyalkyl, lower (alkyl) oximinoalkoxy, lower (alkyl)oximinoalkoxyalkyl, lower carbonylalkyloxy, lower carbonylalkyloxyalkyl, lower hydroxyalkylthio, lower hydroxyalkylthioalkyl, lower oximinoalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylthio, lower alkylcarbonyl, lower cycloalkyl, phenyl, lower haloalkyl, 5- or 6 -membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxy, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower heteroaralkoxyalkyl, lower heteroaryloxyalkyl, lower heteroarylthioalkyl, lower heteroaralkylthioalbyl, lower heteroaralkoxy, lower heteroaralkylthio, lower heteroaryloxy, lower heteroarylthio, lower arylthioalkyl, lower aryloxyalkyl, lower aralkylthioatkyl, lower aralkoxyalkyl, lower albxyaralkoxyalkyl, lower alkoxycarbonylalkyl, lower alkoxycarbonylcyanoalkenyl, lower aminocarbonylalkyl, lower N-alkylaminocarbonyl, phenylaminocarbonyl, lower N,N-dialkylaminocarbonyl, lower N-alkyl-N-arylaminocarbonyl, lower cycloalklylaminocarbonyl, lower heterocycloaminocarbonyl, lower carboxyalkylaminocarbonyl, lower alkylcarbonylalkyl, lower aralkoxycarbonylalkylaminocarbonyl, lower haloaralkyl, lower carboxyhaloalkyl, lower alkoxycarbonylhaloalkyl, lower aminocarbonylhaloalkyl, lower alkylaminocarbonylhaloalkyl, lower N-alkylamino, lower N,N-dialkylamino, N-phenyleunino, lower N-aralkylamino, lower alkyl-N-aralkylamino, lower N-alkylt-N-arylamino, lower arninoalklyl, lower N-alkylaminoalkyl, lower dialkylaminoalkyl, lower N-arylaminoalkyl, lower N-aralkylaminoalkyl, lower N-albyl-N-aralkylaminoalkyl, lower N-alkyl-N-arylaminoalkyl, lower aminoalkoxy, lower aminoalkoxyalkyl, lower aminoalbylthio, lower aminoalkylthioalkyl, lower cycloalkyloxy, lower cycloalkylalkyloxy, phenyloxy, lower aralkoxy, phenylthio, lower aralkylthio, lower alkylsulfinyl, lower alkylsulfonyl, aminosutfonyl, lower N-alkylaminosulfonyl, lower N-arylaminosulfonyl, lower arylsulfonyl, lower dialkylaminosul fonyl, lower N-alkyl -N-arylaminosulfonyl,

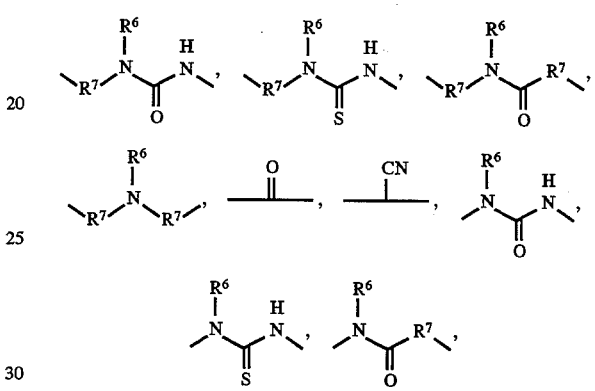

wherein Ar is selected from aryl selected from phenyl, biphenyl and naphthyl, and 5- and 6-membered heteroaryl, wherein Ar is optionally substituted with one or two substituents selected from halo, hydroxyl, amino, nitro, cyano, carbamoyi, lower alkyl, lower atkenyloxy, lower alkoxy, lower alkylehio, lower aikylsulfinyl, lower alkyflsulfonyl, lower alk-yiamino, lower dialklzlamino, lower haloalk71, lower alkoxycarbonyl, lower N-alkyicarbamoyl, lower N,N-dialkylcarbamoyl, lower alkanoylamino, lower cyanoalkoxy, lower carbamoylalkoxy, lower alkoxycarbonylalkoxy and

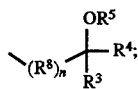

wherein $R^1$ is at least one substituent selected from 5- and 6-membered heterocyclo, lower cycloalkyfl, lower cycloalkenyl and aryl selected from phenyl, biphenyl and naphthyl, where $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, lower alkylamino, phenylamino, nitro, lower alkoxyalkyl, lower alkylsulfinyl, halo, lower alkoxy and lower alkylthio; wherein $R^2$ is selected from lower alkyl and amino; wherein $R^3$ and $R^4$ together form a group of the formula —B—X—$B^1$ which together with the carbon atom to which B and $B^1$ are attached, defines a ring having 6 ring atoms, wherein B and $B^1$, which may be the same or different, each is alkylene and X is oxy, and which ring may bear one, two or three substituents, which may be the same or different, selected from hydroxyl, lower alkyl, lower alkoxy, lower alkenyloxy and lower alkynyloxy; wherein $R^5$ is selected from hydrido, lower alkyl, lower alkenyl, lower alkynyl, lower cyanoalkyl, lower alkanoyl, and benzoyl optionally substituted with a substituent selected from halo, lower alkyl and lower alkoxy; wherein $R^6$ is selected from hydrido, lower alkyl, phenyl and lower aralkyl; wherein $R^7$ is selected from lower alkyl, lower alkenyl and lower alkynyl; wherein $R^8$ is oximino optionally substituted with alkyl; and wherein n is 0 or 1; or a pharmaceutically-acceptable salt thereof.

19. The method of claim 18 wherein A is a radical selected from oxazolyl, and isoxazolyl, wherein A is optionally substituted with a radical selected from acyl, halo, lower alkyl, lower haloalkyl, oxo, cyano, nitro, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkenyl, lower alkynyl, lower alkyloxy, lower hydroxyalkyl, lower hydroxyalkyloxy, lower hydroxyalkyioxyalkyl, lower oximinoalkoxy, lower oximinoalkoxyalkyl, lower (alkyl)oximinoalkoxy, lower (alkyl)oximinoalkoxyalkyl, lower carbonylalkyloxy, lower carbonylalkyloxyalkyi, lower hydroxyalkylthio, lower hydroxyalkylthioalkyl, lower oximinoalkalkylthio, lower oximinoalkylthioalkyl, lower (alkyl)oximinoalkylthio, lower (alkyl)oximinoalkylthioalkyl, lower carbonylalkylthio, lower carbonylalkylthioalkyl, lower alkylthio, lower alkylcarbonyl, lower cycloalkyl, phenyl, lower haloalkyl, 5- or 6-membered heterocyclo, lower cycloalkenyl, lower aralkyl, lower heterocycloalkyl, acyl, lower alkylthioalkyl, lower alkyloxyalkyl, lower alkenylthio, lower alkynylthio, lower alkenyloxl, lower alkynyloxy, lower alkenylthioalkyl, lower alkynylthioalkyl, lower alkenyloxyalkyl, lower alkynyloxyalkyl, phenylcarbonyl, lower aralkylcarbonyl, lower aralkenyl, lower haloalkylcarbonyl, lower alkylaminocarbonylalkyl, lower arylthioalkyl, lower aryloxyalkyl, lower aralkylthioalkyl, lower aralkoxyalkyl, lower alkoxycarbonylalkyl, lower aminocarbonylalkyl, lower N-alkylaminocarbonyl, N-phenylaminocarbonyl, lower alkylcarbonylalkl, lower N-alkylamino, N-phenylamino, lower N-aralkylamino, lower aminoalkyl, lower N-alkylaminoalkyl, lower N-arylaminoalkyl, lower N-aralkylmminoalkyl, lower aminoalkoxy, lower aminoalkoxyalkyl, lower aminoalkylthio, lower aminoalkylthioalkyl, lower cycloalkyloxy, lower cycloalkylalkyloxy, phenyloxy, lower aralkoxy, phenylthio, lower aralkylthio, lower alkylsulfinyl, lower alkylsulfonyl, aminosulfonyl, lower N-alkylaminosulfonyl, N-phenylaminosulfonyl, phenylsulfonyl, oximino,

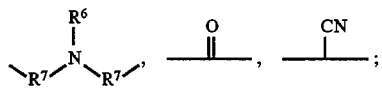

wherein Ar is selected from aryl selected from phenyl, biphenyl, naphthyl, and 5- and 6-membered heteroaryl, wherein Ar is optionally substituted with one or two substituents selected from halo, hydroxl, amino, nitro, cyano, lower alkyl, lower alkoxy, and

wherein $R^1$ is at least one substituent selected from 5- and 6-membered heteroaryl, and aryl selected from phenyi, biphenyl and naphthyl, where $R^1$ is optionally substituted at a substitutable position with one or more radicals selected from lower alkyl, lower haloalkyl, cyano, carboxyl, lower alkoxycarbonyl, hydroxyl, lower hydroxyalkyl, lower haloalkoxy, amino, nitro, lower alkoxyalklyl, lower alkylsulfinyl, halo, lower alkoxy and lower alkylthio; wherein $R^2$ is selected from lower alkyl and amino; wherein $R^3$ and $R^4$ together form a tetrahydropyran ring and which ring may bear one, two or three substituents, which may be the same or different, selected from hydroxyl, lower alkyl, and lower alkoxy; wherein $R^5$ is selected from hydrido and lower alkyl; wherein $R^6$ is selected from hydrido, lower alkyl, phenyl and lower aralkyl; and wherein $R^7$ is selected from lower alkyt, lower alkenyl and lower atkynyl; provided Ar is substituted with

or a pharmaceutically-acceptable salt thereof.

20. The method of claim 19 wherein A is a radical selected from oxazolyl, and isoxazolyl, wherein A is optionally substituted with a radical selected from acyl, halo, lower alklyl, lower haloalkyl, oxo, cyano, carboxyl, lower alkoxy, aminocarbonyl, lower alkoxycarbonyl, lower carboxyalkyl, lower cyanoalkyl, and lower hydroxyalkyl; wherein Y is a radical selected from oxy, thio, sulfinyl, sulfonyl, lower alkyl, lower alkynyl, lower alkenyl, aryl, lower cycloalkyl, 5- or 6-membered heterocyclo, aralkyl, lower alkyloxy, aryloxy, arylthio, 5-or 6-membered heterocyclooxy, lower aralkylthio, lower aralkyloxy, lower alkylthio, lower alkynyloxy, lower alkynylthio, lower alkynyloxyalkyl, lower alkenyloxy, lower alkenylthio, lower alkenyloxyalkyl, lower alkyloxyalkyl, lower alklzlthioalkyl, lower hydroxyalkyloxy, lower hydroxyalkyloxyalkyl, lower oximinoalkoxy, lower oximinoalkoxyalkyl, lower (alkyl)oximinoalkoxy, lower (alkyl)oximinoalkoxyalkyl, lower carbonylalkyloxy, and lower carbonylalkyloxyalkyl; wherein Ar is selected from phonyl, thienyl, oxazolyl, furyl, pyrrolyl, thiazolyl, imidazolyl, isothiazolyl, isoxazolyl, pyrazolyl, cyclopentenyl, and pyridyl, wherein Ar is optionally substituted with one or two substituents selected from halo, hydroxyl, lower alkyl, lower alkoxy, and

wherein $R^1$ is at least one substituent selected from thienyl, oxazolyl, furyl, pyrrolyl, thiazolyl, imidazolyl, isothiazolyl, isoxazolyl, pyrazolyl, cyclopentenyl, pyridyl, and phenyl, where $R^1$ is optionally substituted at a substitutable position with one or more radicals selected from lower alkyl, lower haloalkyl, hydroxyl, lower hydroxyalkyl, lower haloalkoxy, nitre, lower alkoxyalkyl, halo, lower alkoxy and lower alkylthio; wherein $R^2$ is selected from lower alkyl and amine; wherein $R^3$ and $R^4$ together form a tetrahydropyran ring, and which ring may bear one, two or three substituents, which may be the same or different, selected from hydroxyl, lower alkyl, and lower alkoxy; and wherein $R^5$ is selected from hydrido and lower alkyl; or a pharmaceutically-acceptable salt thereof.

21. The method of claim 20 wherein A is a radical selected from oxazolyl, and isoxazolyl, wherein A is optionally substituted with a radical selected from acyl, fluoro, chloro, bromo, methyl, trifluoromethyl, oxo, cyano, carboxyl, methoxy, aminocarbonyl, methoxycarbonyl, ethoxycarbonyl, acetyl, carboxylpropyl, and hydroxymethyl; wherein Y is a radical selected from oxy, ethyl, isopropyl, butyl, 1-propynyl, 2-propynyl, methyloxy, ethyloxy, propyloxy, methylthio, (Z)-1-propenyloxy, (E)-2-propenyloxy, (Z)-2-propenyloxy, (E)-1-propenyloxy, Z)-1-propenyloxymethyl, (E)-2-propenyloxymethyl, (Z)-2-propenyloxymethyl, (E)-1-propenyloxymethyl, 1-propynyloxy, 2-propynyloxy, 1-propynylthio, 2-propynylthio, hydroxymethyloxy, 1-hydroxyethyloxy, 2-hydroxypropyloxy, hydroxymethyloxymethyl, 1-hydroxyethyloxymethyl, 2-hydroxypropyloxymethyl, methyloxymethyl, ethyloxymethyl, propyloxymethyl, 1-propynyloxymethyl, oximinomethyloxy, oximinomethyloxymethyl, (methyl) oximinomethyloxy, (methyl) oximinomethyloxymethyl, triazolylmethyloxy, triazolylmethyloxymethyl, carbonylraethyloxy, carbonylbutyloxy, and carbonylmethyloxymethyl; wherein Ar is selected from phenyl, thienyl, oxazolyl, furyl, pyrrolyl, thiazolyl, imidazolyl, isothiazolyl, isoxazolyl, pyrazotyl, cyclopentenyl, and pyridyl, wherein Ar is substituted with

wherein $R^1$ is selected from thienyl, oxazolyl, furyl, pyrrolyl, thiazolyl, imidazolyl, isothiazolyl, isoxazolyl, pyrazolyl, cyclopentenyl, pyridyl, and phenyl, where $R^1$ is optionally substituted at a substitutable position with one or more radicals selected from methyl, trifluoromethyl, hydroxyl, hydroxymethyl, trifluoromethoxy, nitro, methoxymethyl, fluoro, chloro, bromo, methoxy and methylthio; wherein $R^2$ is methyl or amino; wherein $R^3$ and $R^4$ together form a tetrahydropyran ring, and which ring may bear one, two or three substituents, which may be the same or different, selected from hydroxyl, methyl, and methoxy; and wherein $R^5$ is selected from hydrido and methyl; or a pharmaceutically-acceptable salt thereof.

22. A method of treating a condition benefited by the inhibition of 5-lipoxygenase, cyclooxygenase-2 or both 5-lipoxygenase and cyclooxygenase-2, said method comprising administering to the subject having or susceptible to such inflammation or inflammation associated disorder, a therapeutically-effective aznount of a compound of claim 6, or a pharmaceutically-acceptable salt thereof.

23. A method of treating a condition benefited by the inhibition of 5-1ipoxygenase, cyclooxygenase-2 or both 5-lipoxygenase and cyclooxygenase-2, said method comprising administering to the subject having or susceptible to such inflammation or inflammation-associated disorder, a therapeutically-effective amount of a compound of claim 7, or a pharmaceutically-acceptable salt thereof.

24. The method of claim 17 wherein condition is inflammation or an inflammation-associated disorder.

25. The method of claim 24 wherein the condition is inflammation.

26. The method of claim 24 wherein the condition is an inflammation-associated disorder.

27. The method of claim 26 wherein the inflammation-associated disorder is arthritis.

28. The method of claim 26 wherein the inflammation-associated disorder is pain.

29. The method of claim 26 wherein the inflammation-associated disorder is fever.

* * * * *